(12) United States Patent
Birch et al.

(10) Patent No.: US 7,250,282 B2
(45) Date of Patent: Jul. 31, 2007

(54) ISOMALTULOSE SYNTHASES, POLYNUCLEOTIDES ENCODING THEM AND USES THEREFOR

(75) Inventors: Robert George Birch, Queensland (AU); Luguang Wu, Queensland (AU)

(73) Assignee: The University of Queensland of St. Lucia, Queensland (AU)

( * ) Notice: Subject to any disclaimer, the term of this patent is extended or adjusted under 35 U.S.C. 154(b) by 345 days.

(21) Appl. No.: 10/374,726

(22) Filed: Feb. 27, 2003

(65) Prior Publication Data

US 2004/0005589 A1 Jan. 8, 2004

Related U.S. Application Data

(63) Continuation-in-part of application No. PCT/AU01/01084, filed on Aug. 29, 2001.

(51) Int. Cl.
*C12N 15/61* (2006.01)
*C12N 15/63* (2006.01)
*C12N 15/82* (2006.01)
*C12N 9/90* (2006.01)

(52) U.S. Cl. .................. 435/233; 435/320.1; 435/325; 435/419; 435/252.3; 536/23.2

(58) Field of Classification Search ............... 435/233, 435/230.1, 325, 419, 252.3; 536/23.2, 24.3
See application file for complete search history.

(56) References Cited

U.S. PATENT DOCUMENTS 5,985,622 A  11/1999  Mattes et al. ............... 435/100

FOREIGN PATENT DOCUMENTS

| WO | WO95/20047 | 7/1995 |
| WO | WO01/59135 | 8/2001 |
| WO | WO 01/59136 A1 | 8/2001 |
| WO | WO01/60993 | 8/2001 |
| WO | WO 02/27003 A1 | 4/2002 |

OTHER PUBLICATIONS

Miyata et al., Biosci. Biotech. Biochem. 56(10): 1680-1681 (1992).
Park et al., Biotechnology Letters 14(7): 547-551 (1992).
Tsuyuki et al., J. Gen. Appl. Microbiol. 38: 483-490 (1992).
Börnke et al., Journal of Bacteriology 183(8): 2425-2430 (2001).
Wu et al., Applied and Environmental Microbiology 71(3): 1581-1590 (2005).
Wu et al., Journal of Applied Microbiology 97: 93-103 (2004).
Back et al., Mol Gen Genet 212: 20-26 (1988).
Börnke et al., Planta 214 356-364 (2002).
Cheetham, Biochem J. 220: 213-220 (1984).
Qian et al., Microbiology 143: 855-865 (1997).
Zhang et al., Proc Natl Acad Sci USA 94: 9984-9989 (1997).

*Primary Examiner*—Rebecca Prouty
(74) *Attorney, Agent, or Firm*—Proskauer Rose LLP

(57) ABSTRACT

The invention is directed to novel enzymes that convert sucrose to isomaltulose. More particularly, the present invention discloses novel sucrose isomerases, polynucleotides encoding these sucrose isomerases, methods for isolating such polynucleotides and nucleic acid constructs that express these polynucleotides. Also disclosed are cells, including transformed bacterial or plant cells, and differentiated plants comprising cells, which contain these sucrose isomerase-encoding polynucleotides, as well as extracts thereof. Methods of producing isomaltulose are also disclosed which use the polypeptides, polynucleotides, cells, cell extracts and plants of the invention.

23 Claims, 19 Drawing Sheets

```
   1 ATGTCCTCTC AAGAATTGAA AGCGGCTGTC GCTATTTTTC TTGCAACCAC   50
  51 TTTTTCTGCC ACATCCTATC AGGCCTGCAG TGCCGGGCCA GATACCGCCC  100
 101 CCTCACTCAC CGTTCAGCAA TCAAATGCCC TGCCCACATG GTGGAAGCAG  150
 151 GCTGTTTTTT ATCAGGTATA TCCACGCTCA TTTAAAGATA CGAATGGGGA  200
 201 TGGCATTGGG GATTTAAACG GTATTATTGA GAATTTAGAC TATCTGAAGA  250
 251 AACTGGGTAT TGATGCGATT TGGATCAATC CACATTACGA TTCGCCGAAT  300
 301 ACGGATAATG GTTATGACAT CCGGGATTAC CGTAAGATAA TGAAAGAATA  350
 351 CGGTACGATG GAAGACTTTG ACCGTCTTAT TCAGAAATG AAGAAACGCA   400
 401 ATATGCGTTT GATGATTGAT ATTGTTATCA ACCACACCAG CGATCAGCAT  450
 451 GCGTGGTTTG TTCAGAGCAA ATCGGGTAAG AACAACCCCT ACAGGGACTA  500
 501 TTACTTCTGG CGTGACGGTA AGGATGGCCA TGCCCCCAAT AACTATCCCT  550
 551 CCTTCTTCGG TGGCTCAGCC TGGGAAAAAG ACGATAAATC AGGCCAGTAT  600
 601 TACCTCCATT ACTTTGCCAA ACAGCAACCC GACCTCAACT GGGACAATCC  650
 651 CAAAGTCCGT CAAGACCTGT ATGACATGCT CCGCTTCTGG TTAGATAAAG  700
 701 GCGTTTNTGG TTTACGCTTT GATACCGTTG CCACCTATTC AAAAATCCCG  750
 751 AACTTCCCTG ACCTTAGCCA ACAGCAGTTA AAAATTTCG CCGAGGAATA   800
 801 TACTAAAGGT CCTAAAATTC ACGACTACGT GAATGAAATG AACAGAGAAG  850
 851 TATTATCCCA CTATGATATC GCCACTGCGG GGGAAATATT TGGGGTTCCT  900
 901 CTGGATAAAT CGATTAAGTT TTTCGATCGC CGTAGAAATG AATTAAATAT  950
 951 AGCGTTTACG TTTGATCTGA TCAGACTCGA TCGTGATGCT GATGAAAGAT 1000
1001 GGCGGCGAAA AGACTGGACC CTTTCGCAGT TCCGAAAAAT TGTCGATAAG 1050
1051 GTTGACCAAA CGGCAGGAGA GTATGGGTGG AATGCCTTTT TCTTAGACAA 1100
1101 TCACGACAAT CCCCGCGCGG TTTCTCACTT TGGTGATGAT CGACCACAAT 1150
1151 GGCGCGAGCA TGCGGCGAAA GCACTGGCAA CATTGACGCT GACCCAGCGT 1200
1201 GCAACGCCGT TATCTATCA GGGTTCAGAA CTCGGTATGA CCAATTATCC  1250
1251 CTTTAAAAAA ATCGATGATT TCGATGATGT AGAGGTGAAA GGTTTTTGGC 1300
1301 AAGACTACGT TGAAACAGGC AAAGTGAAAG CTGAGGAATT CCTTCANAAC 1350
1351 GTACGCCAAA CCAGCCGTGA TAACAGCAGA ACCCCCTTCC AGTGGGATGC 1400
1401 AAGCAAAAAT GCGGGCTTTA CCAGCGGAAC CCCTTGGTTA AAAATCAATC 1450
1451 CCAATTATAA AGAAATCAAC AGCGCAGATC AGATTAACAA TCCAAATTCC 1500
1501 GTATTTAACT ATTATAGAAA GCTCATTAAC ATTCGCCACG ACATCCCTGC 1550
1551 CTTAACCTAC GGCAGTTATA TTGATTTAGC TCCTGACAAC AATTCAGTCT 1600
1601 ATGCTTACAC TCGAACGTTT GGCGCTGAAA AATATCTTGT GGTCATTAAT 1650
1651 TTTAAAGAAG AAGTGATGCA CTACACCCTG CCTGGGGATT TATCCATCAA 1700
1701 TAAGGTGATT ACTGAAAACA CAGTCACAC TATTGTGAAT AAAAATGACG   1750
1751 TAGAAGATCC TCGTGGGGCT ACAAGCGTTT GTAGCCCCTT CCAGGCTCAA 1800
1801 AAAAGGCCTG GCGACCCGGG TTACTCTGCT GCCCATTCGA TTCGGTTCTT 1850
1851 GCCCCGGTTT TTCGCTTCAT ACAGGGGCGA CATCCACGCG TTTAAGTAA  1899
```

FIGURE 3

```
   1 ATGTTTCTTA ATGGATTTAA GACAGTTATT GCTCTGACTA TGGCAAGCTC   50
  51 GTTTTATCTT GCCGCCAGCC CGTTAACTAA GCCATCGACC CCTATTGCCG  100
 101 CAACGAATAT ACAAAAGTCC GCTGATTTTC CCATTTGGTG GAAACAGGCA  150
 151 GTATTTTACC AGATTTATCC CCGCTCATTT AAAGATAGCA ATGGTGATGG  200
 201 TATCGGCGAT ATTCCCGGTA TCATTGAGAA ACTGGACTAT TTAAAAATGC  250
 251 TGGGAGTTGA TGCTATCTGG ATAAACCCGC ACTATGAGTC TCCTAACACC  300
 301 GACAATGGTT ACGATATTAG TGATTATCGT AAAATCATGA AGGAGTACGG  350
 351 CAGCATGGCT GACTTTGACC GTCTGGTTGC CGAAATGAAT AAACGTGGTA  400
 401 TGCGCCTGAT GATTGATATT GTTATCAATC ATACCAGCGA TCGTCACCGC  450
 451 TGGTTTGTGC AGAGCCGTTC AGGTAAAGAT AATCCTTACC GCGACTATTA  500
 501 TTTCTGGCGT GATGGTAAAC AGGGACAGGC TCCCAATAAC TATCCCTCTT  550
 551 TCTTTGGCGG TTCAGCCTGG CAACTGGATA AACAGACTGA CCAGTATTAT  600
 601 CTGCACTATT TTGCACCACA GCAGCCGGAT CTGAACTGGG ATAACCCAAA  650
 651 AGTTCGGGCT GAACTCTACG ATATTCTGCG TTTCTGGCTG GATAAAGGCG  700
 701 TATCCGGACT ACGTTTTGAT ACCGTGGCTA CTTTCTCCAA AATTCCTGGC  750
 751 TTCCCGGACC TGTCAAAAGC GCAGCTGAAG AATTTTGCCG AAGCTTATAC  800
 801 TGAGGGGCCG AATATTCATA AATATATCCA TGAAATGAAC CGCCAGGTAC  850
 851 TGTCTAAATA TAATGTTGCC ACCGCTGGTG AAATCTTCGG TGTGCCAGTG  900
 901 AGTGCTATGC CGGATTATTT TGACCGGCGG CGTGAAGAAC TCAATATTGC  950
 951 TTTCACCTTT GATTTGATCA GGCTCGATCG TTATCCCGAT CAGCGCTGGC 1000
1001 GTCGTAAACC ATGGACATTA AGCCAGTTTC GTCAAGTTAT CTCTCAGACT 1050
1051 GACCGTGCCG CCGGTGAATT TGGCTGGAAC GCCTTTTTCC TTGATAACCA 1100
1101 TGATAACCCG CGCCAGGTCT CACACTTTGG TGACGACAGC CCACAATGGC 1150
1151 GCGAACGCTC GGCAAAAGCA CTGGCAACGC TGCTGCTGAC GCAGCGTGCC 1200
1201 ACGCCGTTTA TCTTTCAGGG GGCGGAGTTG GGAATGACTA ATTACCCCTT 1250
1251 TAAAAATATA GAGGAATTTG ATGATATTGA GGTTAAAGGC TTCTGGAACG 1300
1301 ACTATGTAGC CAGCGGAAAA GTAAACGCTG CTGAATTTTT ACAGGAGGTT 1350
1351 CGCATGACCA GCCGCGATAA CAGCCGAACA CCAATGCAGT GGAACGACTC 1400
1401 TGTTAATGCC GGATTCACCC AGGGCAAACC CTGGTTTCAC CTCAATCCCA 1450
1451 ACTATAAGCA ATCAATGCC GCCAGGGNGG TGAATAAACC CGACTCGGTA 1500
1501 TTCAGTTACT ACCGTCAACT GATCAACCTG CGTCACCAGA TCCCGGCACT 1550
1551 GACCAGTGGT GAATACCGTG ATCTCGATCC GCAGAATAAC CAGGTCTATG 1600
1601 CCTATACCCG TATACTGGAT AATGAAAAAT ATCTGGTGGT AGTTAATTTT 1650
1651 AAACCTGAGC AGCTGCATTA CGCTCTGCCA GATAATCTGA CTATTGCCAG 1700
1701 CAGTCTGCTG GAAAATGTCC ACCAACCATC ACTGCAAGAA AATGCCTCCA 1750
1751 CGCTGACTCT TGCTCCGTGG CAAGCCGGGA TCTATAAGCT GAACTGA     1797
```

FIGURE 4

```
  1 MSSQELKAAV AIFLATTFSA TSYQACSAGP DTAPSLTVQQ SNALPTWWKQ  50
 51 AVFYQVYPRS FKDTNGDGIG DLNGIIENLD YLKKLGIDAI WINPHYDSPN 100
101 TDNGYDIRDY RKIMKEYGTM EDFDRLISEM KKRNMRLMID IVINHTSDQH 150
151 AWFVQSKSGK NNPYRDYYFW RDGKDGHAPN NYPSFFGGSA WEKDDKSGQY 200
201 YLHYFAKQQP DLNWDNPKVR QDLYDMLRFW LDKGVXGLRF DTVATYSKIP 250
251 NFPDLSQQQL KNFAEEYTKG PKIHDYVNEM NREVLSHYDI ATAGEIFGVP 300
301 LDKSIKFFDR RRNELNIAFT FDLIRLDRDA DERWRRKDWT LSQFRKIVDK 350
351 VDQTAGEYGW NAFFLDNHDN PRAVSHFGDD RPQWREHAAK ALATLTLTQR 400
401 ATPFIYQGSE LGMTNYPFKK IDDFDDVEVK GFWQDYVETG KVKAEEFLXN 450
451 VRQTSRDNSR TPFQWDASKN AGFTSGTPWL KINPNYKEIN SADQINNPNS 500
501 VFNYYRKLIN IRHDIPALTY GSYIDLAPDN NSVYAYTRTF GAEKYLVVIN 550
551 FKEEVMHYTL PGDLSINKVI TENNSHTIVN KNDVEDPRGA TSVCSPFQAQ 600
601 KRPGDPGYSA AHSIRFLPRF FASYRGDIHA FK*                   632
```

FIGURE 5

```
  1 MFLNGFKTVI ALTMASSFYL AASPLTKPST PIAATNIQKS ADFPIWWKQA  50
 51 VFYQIYPRSF KDSNGDGIGD IPGIIEKLDY LKMLGVDAIW INPHYESPNT 100
101 DNGYDISDYR KIMKEYGSMA DFDRLVAEMN KRGMRLMIDI VINHTSDRHR 150
151 WFVQSRSGKD NPYRDYYFWR DGKQGQAPNN YPSFFGGSAW QLDKQTDQYY 200
201 LHYFAPQQPD LNWDNPKVRA ELYDILRFWL DKGVSGLRFD TVATFSKIPG 250
251 FPDLSKAQLK NFAEAYTEGP NIHKYIHEMN RQVLSKYNVA TAGEIFGVPV 300
301 SAMPDYFDRR REELNIAFTF DLIRLDRYPD QRWRRKPWTL SQFRQVISQT 350
351 DRAAGEFGWN AFFLDNHDNP RQVSHFGDDS PQWRERSAKA LATLLLTQRA 400
401 TPFIFQGAEL GMTNYPFKNI EEFDDIEVKG FWNDYVASGK VNAAEFLQEV 450
451 RMTSRDNSRT PMQWNDSVNA GFTQGKPWFH LNPNYKQINA ARXVNKPDSV 500
501 FSYYRQLINL RHQIPALTSG EYRDLDPQNN QVYAYTRILD NEKYLVVVNF 550
551 KPEQLHYALP DNLTIASSLL ENVHQPSLQE NASTLTLAPW QAGIYKLN*  598
```

FIGURE 6

SEQUENCE LISTING

<160> NUMBER OF SEQ ID NOS: 52

<210> SEQ ID NO 1
<211> LENGTH: 1899
<212> TYPE: DNA
<213> ORGANISM: Erwinia rhapontici
<220> FEATURE:
<221> NAME/KEY: CDS
<222> LOCATION: (1)..(1896)
<220> FEATURE:
<221> NAME/KEY: sig_peptide
<222> LOCATION: (1)..(108)
<220> FEATURE:
<221> NAME/KEY: mat_peptide
<222> LOCATION: (109)..(1899)
<220> FEATURE:
<221> NAME/KEY: modified_base
<222> LOCATION: (707)
<223> OTHER INFORMATION: a, t, c, g, other or unknown
<220> FEATURE:
<221> NAME/KEY: modified_base
<222> LOCATION: (1347)
<223> OTHER INFORMATION: a, t, c, g, other or unknown

<400> SEQUENCE: 1

```
atg tcc tct caa gaa ttg aaa gcg gct gtc gct att ttt ctt gca acc        48
Met Ser Ser Gln Glu Leu Lys Ala Ala Val Ala Ile Phe Leu Ala Thr
    -35             -30                 -25 act ttt tct gcc aca tcc tat cag gcc tgc agt gcc ggg cca gat acc        96
Thr Phe Ser Ala Thr Ser Tyr Gln Ala Cys Ser Ala Gly Pro Asp Thr
-20             -15                 -10                  -5 gcc ccc tca ctc acc gtt cag caa tca aat gcc ctg ccc aca tgg tgg       144
Ala Pro Ser Leu Thr Val Gln Gln Ser Asn Ala Leu Pro Thr Trp Trp
             -1   1               5                  10 aag cag gct gtt ttt tat cag gta tat cca cgc tca ttt aaa gat acg       192
Lys Gln Ala Val Phe Tyr Gln Val Tyr Pro Arg Ser Phe Lys Asp Thr
             15                  20                  25 aat ggg gat ggc att ggg gat tta aac ggt att att gag aat tta gac       240
Asn Gly Asp Gly Ile Gly Asp Leu Asn Gly Ile Ile Glu Asn Leu Asp
 30                  35                  40 tat ctg aag aaa ctg ggt att gat gcg att tgg atc aat cca cat tac       288
Tyr Leu Lys Lys Leu Gly Ile Asp Ala Ile Trp Ile Asn Pro His Tyr
 45                  50                  55                  60 gat tcg ccg aat acg gat aat ggt tat gac atc cgg gat tac cgt aag       336
Asp Ser Pro Asn Thr Asp Asn Gly Tyr Asp Ile Arg Asp Tyr Arg Lys
             65                  70                  75 ata atg aaa gaa tac ggt acg atg gaa gac ttt gac cgt ctt att tca       384
Ile Met Lys Glu Tyr Gly Thr Met Glu Asp Phe Asp Arg Leu Ile Ser
             80                  85                  90 gaa atg aag aaa cgc aat atg cgt ttg atg att gat att gtt atc aac       432
Glu Met Lys Lys Arg Asn Met Arg Leu Met Ile Asp Ile Val Ile Asn
             95                 100                 105 cac acc agc gat cag cat gcg tgg ttt gtt cag agc aaa tcg ggt aag       480
His Thr Ser Asp Gln His Ala Trp Phe Val Gln Ser Lys Ser Gly Lys
        110                 115                 120 aac aac ccc tac agg gac tat tac ttc tgg cgt gac ggt aag gat ggc       528
Asn Asn Pro Tyr Arg Asp Tyr Tyr Phe Trp Arg Asp Gly Lys Asp Gly
125                 130                 135                 140 cat gcc ccc aat aac tat ccc tcc ttc ttc ggt ggc tca gcc tgg gaa       576
His Ala Pro Asn Asn Tyr Pro Ser Phe Phe Gly Gly Ser Ala Trp Glu
                145                 150                 155 aaa gac gat aaa tca ggc cag tat tac ctc cat tac ttt gcc aaa cag       624
Lys Asp Asp Lys Ser Gly Gln Tyr Tyr Leu His Tyr Phe Ala Lys Gln
```

-continued

|     |     |     |     |     | 160 |     |     |     |     | 165 |     |     |     |     | 170 |     |     |      |
|-----|-----|-----|-----|-----|-----|-----|-----|-----|-----|-----|-----|-----|-----|-----|-----|-----|-----|------|
| caa | ccc | gac | ctc | aac | tgg | gac | aat | ccc | aaa | gtc | cgt | caa | gac | ctg | tat |     |     | 672  |
| Gln | Pro | Asp | Leu | Asn | Trp | Asp | Asn | Pro | Lys | Val | Arg | Gln | Asp | Leu | Tyr |     |     |      |
|     |     | 175 |     |     |     |     | 180 |     |     |     |     | 185 |     |     |     |     |     |      |

```
gac atg ctc cgc ttc tgg tta gat aaa ggc gtt tnt ggt tta cgc ttt       720
Asp Met Leu Arg Phe Trp Leu Asp Lys Gly Val Xaa Gly Leu Arg Phe
    190             195             200 gat acc gtt gcc acc tat tca aaa atc ccg aac ttc cct gac ctt agc       768
Asp Thr Val Ala Thr Tyr Ser Lys Ile Pro Asn Phe Pro Asp Leu Ser
205             210             215             220 caa cag cag tta aaa aat ttc gcc gag gaa tat act aaa ggt cct aaa       816
Gln Gln Gln Leu Lys Asn Phe Ala Glu Glu Tyr Thr Lys Gly Pro Lys
                225             230             235 att cac gac tac gtg aat gaa atg aac aga gaa gta tta tcc cac tat       864
Ile His Asp Tyr Val Asn Glu Met Asn Arg Glu Val Leu Ser His Tyr
        240             245             250 gat atc gcc act gcg ggg gaa ata ttt ggg gtt cct ctg gat aaa tcg       912
Asp Ile Ala Thr Ala Gly Glu Ile Phe Gly Val Pro Leu Asp Lys Ser
            255             260             265 att aag ttt ttc gat cgc cgt aga aat gaa tta aat ata gcg ttt acg       960
Ile Lys Phe Phe Asp Arg Arg Arg Asn Glu Leu Asn Ile Ala Phe Thr
    270             275             280 ttt gat ctg atc aga ctc gat cgt gat gct gat gaa aga tgg cgg cga      1008
Phe Asp Leu Ile Arg Leu Asp Arg Asp Ala Asp Glu Arg Trp Arg Arg
285             290             295             300 aaa gac tgg acc ctt tcg cag ttc cga aaa att gtc gat aag gtt gac      1056
Lys Asp Trp Thr Leu Ser Gln Phe Arg Lys Ile Val Asp Lys Val Asp
                305             310             315 caa acg gca gga gag tat ggg tgg aat gcc ttt ttc tta gac aat cac      1104
Gln Thr Ala Gly Glu Tyr Gly Trp Asn Ala Phe Phe Leu Asp Asn His
        320             325             330 gac aat ccc cgc gcg gtt tct cac ttt ggt gat gat cga cca caa tgg      1152
Asp Asn Pro Arg Ala Val Ser His Phe Gly Asp Asp Arg Pro Gln Trp
            335             340             345 cgc gag cat gcg gcg aaa gca ctg gca aca ttg acg ctg acc cag cgt      1200
Arg Glu His Ala Ala Lys Ala Leu Ala Thr Leu Thr Leu Thr Gln Arg
    350             355             360 gca acg ccg ttt atc tat cag ggt tca gaa ctc ggt atg acc aat tat      1248
Ala Thr Pro Phe Ile Tyr Gln Gly Ser Glu Leu Gly Met Thr Asn Tyr
365             370             375             380 ccc ttt aaa aaa atc gat gat ttc gat gat gta gag gtg aaa ggt ttt      1296
Pro Phe Lys Lys Ile Asp Asp Phe Asp Asp Val Glu Val Lys Gly Phe
                385             390             395 tgg caa gac tac gtt gaa aca ggc aaa gtg aaa gct gag gaa ttc ctt      1344
Trp Gln Asp Tyr Val Glu Thr Gly Lys Val Lys Ala Glu Glu Phe Leu
        400             405             410 can aac gta cgc caa acc agc cgt gat aac agc aga acc ccc ttc cag      1392
Thr Asn Val Arg Gln Thr Ser Arg Asp Asn Ser Arg Thr Pro Phe Gln
            415             420             425 tgg gat gca agc aaa aat gcg ggc ttt acc agc gga acc cct tgg tta      1440
Trp Asp Ala Ser Lys Asn Ala Gly Phe Thr Ser Gly Thr Pro Trp Leu
    430             435             440 aaa atc aat ccc aat tat aaa gaa atc aac agc gca gat cag att aac      1488
Lys Ile Asn Pro Asn Tyr Lys Glu Ile Asn Ser Ala Asp Gln Ile Asn
445             450             455             460 aat cca aat tcc gta ttt aac tat tat aga aag ctc att aac att cgc      1536
Asn Pro Asn Ser Val Phe Asn Tyr Tyr Arg Lys Leu Ile Asn Ile Arg
                465             470             475 cac gac atc cct gcc tta acc tac ggc agt tat att gat tta gct cct      1584
```

-continued

```
                His Asp Ile Pro Ala Leu Thr Tyr Gly Ser Tyr Ile Asp Leu Ala Pro
                            480                 485                 490 gac aac aat tca gtc tat gct tac act cga acg ttt ggc gct gaa aaa      1632
Asp Asn Asn Ser Val Tyr Ala Tyr Thr Arg Thr Phe Gly Ala Glu Lys
            495                 500                 505 tat ctt gtg gtc att aat ttt aaa gaa gaa gtg atg cac tac acc ctg      1680
Tyr Leu Val Val Ile Asn Phe Lys Glu Glu Val Met His Tyr Thr Leu
    510                 515                 520 cct ggg gat tta tcc atc aat aag gtg att act gaa aac aac agt cac      1728
Pro Gly Asp Leu Ser Ile Asn Lys Val Ile Thr Glu Asn Asn Ser His
525                 530                 535                 540 act att gtg aat aaa aat gac gta gaa gat cct cgt ggg gct aca agc      1776
Thr Ile Val Asn Lys Asn Asp Val Glu Asp Pro Arg Gly Ala Thr Ser
                545                 550                 555 gtt tgt agc ccc ttc cag gct caa aaa agg cct ggc gac ccg ggt tac      1824
Val Cys Ser Pro Phe Gln Ala Gln Lys Arg Pro Gly Asp Pro Gly Tyr
            560                 565                 570 tct gct gcc cat tcg att cgg ttc ttg ccc cgg ttt ttc gct tca tac      1872
Ser Ala Ala His Ser Ile Arg Phe Leu Pro Arg Phe Phe Ala Ser Tyr
    575                 580                 585 agg ggc gac atc cac gcg ttt aag taa                                  1899
Arg Gly Asp Ile His Ala Phe Lys
590                 595

<210> SEQ ID NO 2
<211> LENGTH: 632
<212> TYPE: PRT
<213> ORGANISM: Erwinia rhapontici
<220> FEATURE:
<221> NAME/KEY: MOD_RES
<222> LOCATION: (200)
<223> OTHER INFORMATION: Any amino acid

<400> SEQUENCE: 2

Met Ser Ser Gln Glu Leu Lys Ala Ala Val Ala Ile Phe Leu Ala Thr
        -35                 -30                 -25

Thr Phe Ser Ala Thr Ser Tyr Gln Ala Cys Ser Ala Gly Pro Asp Thr
-20                 -15                 -10                  -5

Ala Pro Ser Leu Thr Val Gln Gln Ser Asn Ala Leu Pro Thr Trp Trp
             -1   1                   5                      10

Lys Gln Ala Val Phe Tyr Gln Val Tyr Pro Arg Ser Phe Lys Asp Thr
            15                  20                  25

Asn Gly Asp Gly Ile Gly Asp Leu Asn Gly Ile Ile Glu Asn Leu Asp
        30                  35                  40

Tyr Leu Lys Lys Leu Gly Ile Asp Ala Ile Trp Ile Asn Pro His Tyr
45                  50                  55                  60

Asp Ser Pro Asn Thr Asp Asn Gly Tyr Asp Ile Arg Asp Tyr Arg Lys
                65                  70                  75

Ile Met Lys Glu Tyr Gly Thr Met Glu Asp Phe Asp Arg Leu Ile Ser
            80                  85                  90

Glu Met Lys Lys Arg Asn Met Arg Leu Met Ile Asp Ile Val Ile Asn
        95                 100                 105

His Thr Ser Asp Gln His Ala Trp Phe Val Gln Ser Lys Ser Gly Lys
    110                 115                 120

Asn Asn Pro Tyr Arg Asp Tyr Tyr Phe Trp Arg Asp Gly Lys Asp Gly
125                 130                 135                 140

His Ala Pro Asn Asn Tyr Pro Ser Phe Phe Gly Gly Ser Ala Trp Glu
                145                 150                 155
```

```
Lys Asp Asp Lys Ser Gly Gln Tyr Tyr Leu His Tyr Phe Ala Lys Gln
        160                 165                 170

Gln Pro Asp Leu Asn Trp Asp Asn Pro Lys Val Arg Gln Asp Leu Tyr
        175                 180                 185

Asp Met Leu Arg Phe Trp Leu Asp Lys Gly Val Xaa Gly Leu Arg Phe
        190                 195                 200

Asp Thr Val Ala Thr Tyr Ser Lys Ile Pro Asn Phe Pro Asp Leu Ser
205                 210                 215                 220

Gln Gln Gln Leu Lys Asn Phe Ala Glu Glu Tyr Thr Lys Gly Pro Lys
                225                 230                 235

Ile His Asp Tyr Val Asn Glu Met Asn Arg Glu Val Leu Ser His Tyr
                240                 245                 250

Asp Ile Ala Thr Ala Gly Glu Ile Phe Gly Val Pro Leu Asp Lys Ser
            255                 260                 265

Ile Lys Phe Phe Asp Arg Arg Arg Asn Glu Leu Asn Ile Ala Phe Thr
        270                 275                 280

Phe Asp Leu Ile Arg Leu Asp Arg Asp Ala Asp Glu Arg Trp Arg Arg
285                 290                 295                 300

Lys Asp Trp Thr Leu Ser Gln Phe Arg Lys Ile Val Asp Lys Val Asp
                305                 310                 315

Gln Thr Ala Gly Glu Tyr Gly Trp Asn Ala Phe Phe Leu Asp Asn His
            320                 325                 330

Asp Asn Pro Arg Ala Val Ser His Phe Gly Asp Asp Arg Pro Gln Trp
        335                 340                 345

Arg Glu His Ala Ala Lys Ala Leu Ala Thr Leu Thr Leu Thr Gln Arg
        350                 355                 360

Ala Thr Pro Phe Ile Tyr Gln Gly Ser Glu Leu Gly Met Thr Asn Tyr
365                 370                 375                 380

Pro Phe Lys Lys Ile Asp Asp Phe Asp Asp Val Glu Val Lys Gly Phe
                385                 390                 395

Trp Gln Asp Tyr Val Glu Thr Gly Lys Val Lys Ala Glu Glu Phe Leu
                400                 405                 410

Thr Asn Val Arg Gln Thr Ser Arg Asp Asn Ser Arg Thr Pro Phe Gln
            415                 420                 425

Trp Asp Ala Ser Lys Asn Ala Gly Phe Thr Ser Gly Thr Pro Trp Leu
        430                 435                 440

Lys Ile Asn Pro Asn Tyr Lys Glu Ile Asn Ser Ala Asp Gln Ile Asn
445                 450                 455                 460

Asn Pro Asn Ser Val Phe Asn Tyr Tyr Arg Lys Leu Ile Asn Ile Arg
                465                 470                 475

His Asp Ile Pro Ala Leu Thr Tyr Gly Ser Tyr Ile Asp Leu Ala Pro
            480                 485                 490

Asp Asn Asn Ser Val Tyr Ala Tyr Thr Arg Thr Phe Gly Ala Glu Lys
        495                 500                 505

Tyr Leu Val Val Ile Asn Phe Lys Glu Glu Val Met His Tyr Thr Leu
510                 515                 520

Pro Gly Asp Leu Ser Ile Asn Lys Val Ile Thr Glu Asn Asn Ser His
525                 530                 535                 540

Thr Ile Val Asn Lys Asn Asp Val Glu Asp Pro Arg Gly Ala Thr Ser
                545                 550                 555

Val Cys Ser Pro Phe Gln Ala Gln Lys Arg Pro Gly Asp Pro Gly Tyr
            560                 565                 570

Ser Ala Ala His Ser Ile Arg Phe Leu Pro Arg Phe Phe Ala Ser Tyr
```

```
                        575                 580                 585
Arg Gly Asp Ile His Ala Phe Lys
        590                 595

<210> SEQ ID NO 3
<211> LENGTH: 1791
<212> TYPE: DNA
<213> ORGANISM: Erwinia rhapontici
<220> FEATURE:
<221> NAME/KEY: CDS
<222> LOCATION: (1)..(1788)
<220> FEATURE:
<221> NAME/KEY: mat_peptide
<222> LOCATION: (1)..(1791)
<220> FEATURE:
<221> NAME/KEY: modified_base
<222> LOCATION: (599)
<223> OTHER INFORMATION: a, t, c, g, other or unknown
<220> FEATURE:
<221> NAME/KEY: modified_base
<222> LOCATION: (1239)
<223> OTHER INFORMATION: a, t, c, g, other or unknown

<400> SEQUENCE: 3 acc gtt cag caa tca aat gcc ctg ccc aca tgg tgg aag cag gct gtt      48
Thr Val Gln Gln Ser Asn Ala Leu Pro Thr Trp Trp Lys Gln Ala Val
  1               5                  10                  15 ttt tat cag gta tat cca cgc tca ttt aaa gat acg aat ggg gat ggc      96
Phe Tyr Gln Val Tyr Pro Arg Ser Phe Lys Asp Thr Asn Gly Asp Gly
             20                  25                  30 att ggg gat tta aac ggt att att gag aat tta gac tat ctg aag aaa     144
Ile Gly Asp Leu Asn Gly Ile Ile Glu Asn Leu Asp Tyr Leu Lys Lys
         35                  40                  45 ctg ggt att gat gcg att tgg atc aat cca cat tac gat tcg ccg aat     192
Leu Gly Ile Asp Ala Ile Trp Ile Asn Pro His Tyr Asp Ser Pro Asn
     50                  55                  60 acg gat aat ggt tat gac atc cgg gat tac cgt aag ata atg aaa gaa     240
Thr Asp Asn Gly Tyr Asp Ile Arg Asp Tyr Arg Lys Ile Met Lys Glu
 65                  70                  75                  80 tac ggt acg atg gaa gac ttt gac cgt ctt att tca gaa atg aag aaa     288
Tyr Gly Thr Met Glu Asp Phe Asp Arg Leu Ile Ser Glu Met Lys Lys
                 85                  90                  95 cgc aat atg cgt ttg atg att gat att gtt atc aac cac acc agc gat     336
Arg Asn Met Arg Leu Met Ile Asp Ile Val Ile Asn His Thr Ser Asp
            100                 105                 110 cag cat gcg tgg ttt gtt cag agc aaa tcg ggt aag aac aac ccc tac     384
Gln His Ala Trp Phe Val Gln Ser Lys Ser Gly Lys Asn Asn Pro Tyr
        115                 120                 125 agg gac tat tac ttc tgg cgt gac ggt aag gat ggc cat gcc ccc aat     432
Arg Asp Tyr Tyr Phe Trp Arg Asp Gly Lys Asp Gly His Ala Pro Asn
    130                 135                 140 aac tat ccc tcc ttc ttc ggt ggc tca gcc tgg gaa aaa gac gat aaa     480
Asn Tyr Pro Ser Phe Phe Gly Gly Ser Ala Trp Glu Lys Asp Asp Lys
145                 150                 155                 160 tca ggc cag tat tac ctc cat tac ttt gcc aaa cag caa ccc gac ctc     528
Ser Gly Gln Tyr Tyr Leu His Tyr Phe Ala Lys Gln Gln Pro Asp Leu
                165                 170                 175 aac tgg gac aat ccc aaa gtc cgt caa gac ctg tat gac atg ctc cgc     576
Asn Trp Asp Asn Pro Lys Val Arg Gln Asp Leu Tyr Asp Met Leu Arg
            180                 185                 190 ttc tgg tta gat aaa ggc gtt tnt ggt tta cgc ttt gat acc gtt gcc     624
Phe Trp Leu Asp Lys Gly Val Xaa Gly Leu Arg Phe Asp Thr Val Ala
        195                 200                 205
```

-continued

| | | |
|---|---|---|
| acc tat tca aaa atc ccg aac ttc cct gac ctt agc caa cag cag tta<br>Thr Tyr Ser Lys Ile Pro Asn Phe Pro Asp Leu Ser Gln Gln Gln Leu<br>210                          215                    220 | | 672 |
| aaa aat ttc gcc gag gaa tat act aaa ggt cct aaa att cac gac tac<br>Lys Asn Phe Ala Glu Glu Tyr Thr Lys Gly Pro Lys Ile His Asp Tyr<br>225                        230                               240 | | 720 |
| gtg aat gaa atg aac aga gaa gta tta tcc cac tat gat atc gcc act<br>Val Asn Glu Met Asn Arg Glu Val Leu Ser His Tyr Asp Ile Ala Thr<br>                  245                          250                      255 | | 768 |
| gcg ggg gaa ata ttt ggg gtt cct ctg gat aaa tcg att aag ttt ttc<br>Ala Gly Glu Ile Phe Gly Val Pro Leu Asp Lys Ser Ile Lys Phe Phe<br>              260                            265                      270 | | 816 |
| gat cgc cgt aga aat gaa tta aat ata gcg ttt acg ttt gat ctg atc<br>Asp Arg Arg Arg Asn Glu Leu Asn Ile Ala Phe Thr Phe Asp Leu Ile<br>        275                          280                          285 | | 864 |
| aga ctc gat cgt gat gct gat gaa aga tgg cgg cga aaa gac tgg acc<br>Arg Leu Asp Arg Asp Ala Asp Glu Arg Trp Arg Arg Lys Asp Trp Thr<br>290                          295                    300 | | 912 |
| ctt tcg cag ttc cga aaa att gtc gat aag gtt gac caa acg gca gga<br>Leu Ser Gln Phe Arg Lys Ile Val Asp Lys Val Asp Gln Thr Ala Gly<br>305                        310                          315                    320 | | 960 |
| gag tat ggg tgg aat gcc ttt ttc tta gac aat cac gac aat ccc cgc<br>Glu Tyr Gly Trp Asn Ala Phe Phe Leu Asp Asn His Asp Asn Pro Arg<br>                  325                          330                      335 | | 1008 |
| gcg gtt tct cac ttt ggt gat gat cga cca caa tgg cgc gag cat gcg<br>Ala Val Ser His Phe Gly Asp Asp Arg Pro Gln Trp Arg Glu His Ala<br>              340                            345                      350 | | 1056 |
| gcg aaa gca ctg gca aca ttg acg ctg acc cag cgt gca acg ccg ttt<br>Ala Lys Ala Leu Ala Thr Leu Thr Leu Thr Gln Arg Ala Thr Pro Phe<br>        355                          360                          365 | | 1104 |
| atc tat cag ggt tca gaa ctc ggt atg acc aat tat ccc ttt aaa aaa<br>Ile Tyr Gln Gly Ser Glu Leu Gly Met Thr Asn Tyr Pro Phe Lys Lys<br>370                          375                          380 | | 1152 |
| atc gat gat ttc gat gat gta gag gtg aaa ggt ttt tgg caa gac tac<br>Ile Asp Asp Phe Asp Asp Val Glu Val Lys Gly Phe Trp Gln Asp Tyr<br>385                        390                          395                    400 | | 1200 |
| gtt gaa aca ggc aaa gtg aaa gct gag gaa ttc ctt can aac gta cgc<br>Val Glu Thr Gly Lys Val Lys Ala Glu Glu Phe Leu Thr Asn Val Arg<br>                  405                          410                      415 | | 1248 |
| caa acc agc cgt gat aac agc aga acc ccc ttc cag tgg gat gca agc<br>Gln Thr Ser Arg Asp Asn Ser Arg Thr Pro Phe Gln Trp Asp Ala Ser<br>        420                          425                          430 | | 1296 |
| aaa aat gcg ggc ttt acc agc gga acc cct tgg tta aaa atc aat ccc<br>Lys Asn Ala Gly Phe Thr Ser Gly Thr Pro Trp Leu Lys Ile Asn Pro<br>435                          440                          445 | | 1344 |
| aat tat aaa gaa atc aac agc gca gat cag att aac aat cca aat tcc<br>Asn Tyr Lys Glu Ile Asn Ser Ala Asp Gln Ile Asn Asn Pro Asn Ser<br>450                        455                          460 | | 1392 |
| gta ttt aac tat tat aga aag ctc att aac att cgc cac gac atc cct<br>Val Phe Asn Tyr Tyr Arg Lys Leu Ile Asn Ile Arg His Asp Ile Pro<br>465                        470                          475                    480 | | 1440 |
| gcc tta acc tac ggc agt tat att gat tta gct cct gac aac aat tca<br>Ala Leu Thr Tyr Gly Ser Tyr Ile Asp Leu Ala Pro Asp Asn Asn Ser<br>                  485                          490                      495 | | 1488 |
| gtc tat gct tac act cga acg ttt ggc gct gaa aaa tat ctt gtg gtc<br>Val Tyr Ala Tyr Thr Arg Thr Phe Gly Ala Glu Lys Tyr Leu Val Val<br>              500                            505                      510 | | 1536 |
| att aat ttt aaa gaa gaa gtg atg cac tac acc ctg cct ggg gat tta<br>Ile Asn Phe Lys Glu Glu Val Met His Tyr Thr Leu Pro Gly Asp Leu<br>        515                          520                          525 | | 1584 |

-continued

```
tcc atc aat aag gtg att act gaa aac aac agt cac act att gtg aat    1632
Ser Ile Asn Lys Val Ile Thr Glu Asn Asn Ser His Thr Ile Val Asn
        530                 535                 540 aaa aat gac gta gaa gat cct cgt ggg gct aca agc gtt tgt agc ccc    1680
Lys Asn Asp Val Glu Asp Pro Arg Gly Ala Thr Ser Val Cys Ser Pro
545                 550                 555                 560 ttc cag gct caa aaa agg cct ggc gac ccg ggt tac tct gct gcc cat    1728
Phe Gln Ala Gln Lys Arg Pro Gly Asp Pro Gly Tyr Ser Ala Ala His
                565                 570                 575 tcg att cgg ttc ttg ccc cgg ttt ttc gct tca tac agg ggc gac atc    1776
Ser Ile Arg Phe Leu Pro Arg Phe Phe Ala Ser Tyr Arg Gly Asp Ile
            580                 585                 590 cac gcg ttt aag taa                                                1791
His Ala Phe Lys
        595
```

<210> SEQ ID NO 4
<211> LENGTH: 596
<212> TYPE: PRT
<213> ORGANISM: Erwinia rhapontici
<220> FEATURE:
<221> NAME/KEY: MOD_RES
<222> LOCATION: (200)
<223> OTHER INFORMATION: Any amino acid

<400> SEQUENCE: 4

```
Thr Val Gln Gln Ser Asn Ala Leu Pro Thr Trp Trp Lys Gln Ala Val
 1               5                  10                  15

Phe Tyr Gln Val Tyr Pro Arg Ser Phe Lys Asp Thr Asn Gly Asp Gly
                20                  25                  30

Ile Gly Asp Leu Asn Gly Ile Ile Glu Asn Leu Asp Tyr Leu Lys Lys
            35                  40                  45

Leu Gly Ile Asp Ala Ile Trp Ile Asn Pro His Tyr Asp Ser Pro Asn
        50                  55                  60

Thr Asp Asn Gly Tyr Asp Ile Arg Asp Tyr Arg Lys Ile Met Lys Glu
65                  70                  75                  80

Tyr Gly Thr Met Glu Asp Phe Asp Arg Leu Ile Ser Glu Met Lys Lys
                85                  90                  95

Arg Asn Met Arg Leu Met Ile Asp Ile Val Ile Asn His Thr Ser Asp
            100                 105                 110

Gln His Ala Trp Phe Val Gln Ser Lys Ser Gly Lys Asn Asn Pro Tyr
        115                 120                 125

Arg Asp Tyr Tyr Phe Trp Arg Asp Gly Lys Asp Gly His Ala Pro Asn
    130                 135                 140

Asn Tyr Pro Ser Phe Phe Gly Gly Ser Ala Trp Glu Lys Asp Asp Lys
145                 150                 155                 160

Ser Gly Gln Tyr Tyr Leu His Tyr Phe Ala Lys Gln Gln Pro Asp Leu
                165                 170                 175

Asn Trp Asp Asn Pro Lys Val Arg Gln Asp Leu Tyr Asp Met Leu Arg
            180                 185                 190

Phe Trp Leu Asp Lys Gly Val Xaa Gly Leu Arg Phe Asp Thr Val Ala
        195                 200                 205

Thr Tyr Ser Lys Ile Pro Asn Phe Pro Asp Leu Ser Gln Gln Gln Leu
    210                 215                 220

Lys Asn Phe Ala Glu Glu Tyr Thr Lys Gly Pro Lys Ile His Asp Tyr
225                 230                 235                 240

Val Asn Glu Met Asn Arg Glu Val Leu Ser His Tyr Asp Ile Ala Thr
```

```
                    245                 250                 255
Ala Gly Glu Ile Phe Gly Val Pro Leu Asp Lys Ser Ile Lys Phe Phe
                260                 265                 270

Asp Arg Arg Asn Glu Leu Asn Ile Ala Phe Thr Phe Asp Leu Ile
            275                 280                 285

Arg Leu Asp Arg Asp Ala Asp Glu Arg Trp Arg Lys Asp Trp Thr
        290                 295                 300

Leu Ser Gln Phe Arg Lys Ile Val Asp Lys Val Asp Gln Thr Ala Gly
305                 310                 315                 320

Glu Tyr Gly Trp Asn Ala Phe Phe Leu Asp Asn His Asp Asn Pro Arg
                325                 330                 335

Ala Val Ser His Phe Gly Asp Asp Arg Pro Gln Trp Arg Glu His Ala
                340                 345                 350

Ala Lys Ala Leu Ala Thr Leu Thr Leu Thr Gln Arg Ala Thr Pro Phe
            355                 360                 365

Ile Tyr Gln Gly Ser Glu Leu Gly Met Thr Asn Tyr Pro Phe Lys Lys
        370                 375                 380

Ile Asp Asp Phe Asp Asp Val Glu Val Lys Gly Phe Trp Gln Asp Tyr
385                 390                 395                 400

Val Glu Thr Gly Lys Val Lys Ala Glu Glu Phe Leu Thr Asn Val Arg
                405                 410                 415

Gln Thr Ser Arg Asp Asn Ser Arg Thr Pro Phe Gln Trp Asp Ala Ser
            420                 425                 430

Lys Asn Ala Gly Phe Thr Ser Gly Thr Pro Trp Leu Lys Ile Asn Pro
        435                 440                 445

Asn Tyr Lys Glu Ile Asn Ser Ala Asp Gln Ile Asn Asn Pro Asn Ser
450                 455                 460

Val Phe Asn Tyr Tyr Arg Lys Leu Ile Asn Ile Arg His Asp Ile Pro
465                 470                 475                 480

Ala Leu Thr Tyr Gly Ser Tyr Ile Asp Leu Ala Pro Asp Asn Asn Ser
                485                 490                 495

Val Tyr Ala Tyr Thr Arg Thr Phe Gly Ala Glu Lys Tyr Leu Val Val
            500                 505                 510

Ile Asn Phe Lys Glu Glu Val Met His Tyr Thr Leu Pro Gly Asp Leu
        515                 520                 525

Ser Ile Asn Lys Val Ile Thr Glu Asn Asn Ser His Thr Ile Val Asn
    530                 535                 540

Lys Asn Asp Val Glu Asp Pro Arg Gly Ala Thr Ser Val Cys Ser Pro
545                 550                 555                 560

Phe Gln Ala Gln Lys Arg Pro Gly Asp Pro Gly Tyr Ser Ala Ala His
                565                 570                 575

Ser Ile Arg Phe Leu Pro Arg Phe Phe Ala Ser Tyr Arg Gly Asp Ile
            580                 585                 590

His Ala Phe Lys
        595

<210> SEQ ID NO 5
<211> LENGTH: 108
<212> TYPE: DNA
<213> ORGANISM: Erwinia rhapontici
<220> FEATURE:
<221> NAME/KEY: CDS
<222> LOCATION: (1)..(108)
<220> FEATURE:
<221> NAME/KEY: sig_peptide
<222> LOCATION: (1)..(108)
```

<400> SEQUENCE: 5

```
atg tcc tct caa gaa ttg aaa gcg gct gtc gct att ttt ctt gca acc    48
Met Ser Ser Gln Glu Leu Lys Ala Ala Val Ala Ile Phe Leu Ala Thr
 1               5                  10                  15 act ttt tct gcc aca tcc tat cag gcc tgc agt gcc ggg cca gat acc    96
Thr Phe Ser Ala Thr Ser Tyr Gln Ala Cys Ser Ala Gly Pro Asp Thr
                 20                  25                  30 gcc ccc tca ctc                                                   108
Ala Pro Ser Leu
             35
```

<210> SEQ ID NO 6
<211> LENGTH: 36
<212> TYPE: PRT
<213> ORGANISM: Erwinia rhapontici

<400> SEQUENCE: 6

```
Met Ser Ser Gln Glu Leu Lys Ala Ala Val Ala Ile Phe Leu Ala Thr
 1               5                  10                  15

Thr Phe Ser Ala Thr Ser Tyr Gln Ala Cys Ser Ala Gly Pro Asp Thr
                 20                  25                  30

Ala Pro Ser Leu
             35
```

<210> SEQ ID NO 7
<211> LENGTH: 1797
<212> TYPE: DNA
<213> ORGANISM: Unknown Organism
<220> FEATURE:
<223> OTHER INFORMATION: Description of Unknown Organism: Bacterial
      isolate 68J
<220> FEATURE:
<221> NAME/KEY: CDS
<222> LOCATION: (1)..(1794)
<220> FEATURE:
<221> NAME/KEY: sig_peptide
<222> LOCATION: (1)..(99)
<220> FEATURE:
<221> NAME/KEY: mat_peptide
<222> LOCATION: (100)..(1797)
<220> FEATURE:
<221> NAME/KEY: modified_base
<222> LOCATION: (1478)
<223> OTHER INFORMATION: a, t, c, g, other or unknown

<400> SEQUENCE: 7

```
atg ttt ctt aat gga ttt aag aca gtt att gct ctg act atg gca agc    48
Met Phe Leu Asn Gly Phe Lys Thr Val Ile Ala Leu Thr Met Ala Ser
            -30                 -25                 -20 tcg ttt tat ctt gcc gcc agc ccg tta act aag cca tcg acc cct att    96
Ser Phe Tyr Leu Ala Ala Ser Pro Leu Thr Lys Pro Ser Thr Pro Ile
        -15                 -10                  -5 gcc gca acg aat ata caa aag tcc gct gat ttt ccc att tgg tgg aaa   144
Ala Ala Thr Asn Ile Gln Lys Ser Ala Asp Phe Pro Ile Trp Trp Lys
 -1  1               5                  10                  15 cag gca gta ttt tac cag att tat ccc cgc tca ttt aaa gat agc aat   192
Gln Ala Val Phe Tyr Gln Ile Tyr Pro Arg Ser Phe Lys Asp Ser Asn
                 20                  25                  30 ggt gat ggt atc ggc gat att ccc ggt atc att gag aaa ctg gac tat   240
Gly Asp Gly Ile Gly Asp Ile Pro Gly Ile Ile Glu Lys Leu Asp Tyr
             35                  40                  45 tta aaa atg ctg gga gtt gat gct atc tgg ata aac ccg cac tat gag   288
Leu Lys Met Leu Gly Val Asp Ala Ile Trp Ile Asn Pro His Tyr Glu
         50                  55                  60
```

```
                                            -continued tct cct aac acc gac aat ggt tac gat att agt gat tat cgt aaa atc    336
Ser Pro Asn Thr Asp Asn Gly Tyr Asp Ile Ser Asp Tyr Arg Lys Ile
     65                  70                  75 atg aag gag tac ggc agc atg gct gac ttt gac cgt ctg gtt gcc gaa    384
Met Lys Glu Tyr Gly Ser Met Ala Asp Phe Asp Arg Leu Val Ala Glu
 80                  85                  90                  95 atg aat aaa cgt ggt atg cgc ctg atg att gat att gtt atc aat cat    432
Met Asn Lys Arg Gly Met Arg Leu Met Ile Asp Ile Val Ile Asn His
                100                 105                 110 acc agc gat cgt cac cgc tgg ttt gtg cag agc cgt tca ggt aaa gat    480
Thr Ser Asp Arg His Arg Trp Phe Val Gln Ser Arg Ser Gly Lys Asp
            115                 120                 125 aat cct tac cgc gac tat tat ttc tgg cgt gat ggt aaa cag gga cag    528
Asn Pro Tyr Arg Asp Tyr Tyr Phe Trp Arg Asp Gly Lys Gln Gly Gln
        130                 135                 140 gct ccc aat aac tat ccc tct ttc ttt ggc ggt tca gcc tgg caa ctg    576
Ala Pro Asn Asn Tyr Pro Ser Phe Phe Gly Gly Ser Ala Trp Gln Leu
    145                 150                 155 gat aaa cag act gac cag tat tat ctg cac tat ttt gca cca cag cag    624
Asp Lys Gln Thr Asp Gln Tyr Tyr Leu His Tyr Phe Ala Pro Gln Gln
160                 165                 170                 175 ccg gat ctg aac tgg gat aac cca aaa gtt cgg gct gaa ctc tac gat    672
Pro Asp Leu Asn Trp Asp Asn Pro Lys Val Arg Ala Glu Leu Tyr Asp
                180                 185                 190 att ctg cgt ttc tgg ctg gat aaa ggc gta tcc gga cta cgt ttt gat    720
Ile Leu Arg Phe Trp Leu Asp Lys Gly Val Ser Gly Leu Arg Phe Asp
            195                 200                 205 acc gtg gct act ttc tcc aaa att cct ggc ttc ccg gac ctg tca aaa    768
Thr Val Ala Thr Phe Ser Lys Ile Pro Gly Phe Pro Asp Leu Ser Lys
        210                 215                 220 gcg cag ctg aag aat ttt gcc gaa gct tat act gag ggg ccg aat att    816
Ala Gln Leu Lys Asn Phe Ala Glu Ala Tyr Thr Glu Gly Pro Asn Ile
    225                 230                 235 cat aaa tat atc cat gaa atg aac cgc cag gta ctg tct aaa tat aat    864
His Lys Tyr Ile His Glu Met Asn Arg Gln Val Leu Ser Lys Tyr Asn
240                 245                 250                 255 gtt gcc acc gct ggt gaa atc ttc ggt gtg cca gtg agt gct atg ccg    912
Val Ala Thr Ala Gly Glu Ile Phe Gly Val Pro Val Ser Ala Met Pro
                260                 265                 270 gat tat ttt gac cgg cgg cgt gaa gaa ctc aat att gct ttc acc ttt    960
Asp Tyr Phe Asp Arg Arg Arg Glu Glu Leu Asn Ile Ala Phe Thr Phe
            275                 280                 285 gat ttg atc agg ctc gat cgt tat ccc gat cag cgc tgg cgt cgt aaa   1008
Asp Leu Ile Arg Leu Asp Arg Tyr Pro Asp Gln Arg Trp Arg Arg Lys
        290                 295                 300 cca tgg aca tta agc cag ttt cgt caa gtt atc tct cag act gac cgt   1056
Pro Trp Thr Leu Ser Gln Phe Arg Gln Val Ile Ser Gln Thr Asp Arg
    305                 310                 315 gcc gcc ggt gaa ttt ggc tgg aac gcc ttt ttc ctt gat aac cat gat   1104
Ala Ala Gly Glu Phe Gly Trp Asn Ala Phe Phe Leu Asp Asn His Asp
320                 325                 330                 335 aac ccg cgc cag gtc tca cac ttt ggt gac gac agc cca caa tgg cgc   1152
Asn Pro Arg Gln Val Ser His Phe Gly Asp Asp Ser Pro Gln Trp Arg
                340                 345                 350 gaa cgc tcg gca aaa gca ctg gca acg ctg ctg ctg acg cag cgt gcc   1200
Glu Arg Ser Ala Lys Ala Leu Ala Thr Leu Leu Leu Thr Gln Arg Ala
            355                 360                 365 acg ccg ttt atc ttt cag ggg gcg gag ttg gga atg act aat tac ccc   1248
Thr Pro Phe Ile Phe Gln Gly Ala Glu Leu Gly Met Thr Asn Tyr Pro
```

|  |  |  |  |  |  |  |  |  |  |  |  |  |  |  |  |
|---|---|---|---|---|---|---|---|---|---|---|---|---|---|---|---|
|  |  |  |  | 370 |  |  |  |  | 375 |  |  |  |  | 380 |  |
| ttt | aaa | aat | ata | gag | gaa | ttt | gat | gat | att | gag | gtt | aaa | ggc | ttc | tgg |
| Phe | Lys | Asn | Ile | Glu | Glu | Phe | Asp | Asp | Ile | Glu | Val | Lys | Gly | Phe | Trp |
|  | 385 |  |  |  |  | 390 |  |  |  |  | 395 |  |  |  |  |

1296 aac gac tat gta gcc agc gga aaa gta aac gct gct gaa ttt tta cag  1344
Asn Asp Tyr Val Ala Ser Gly Lys Val Asn Ala Ala Glu Phe Leu Gln
400             405                 410                 415 gag gtt cgc atg acc agc cgc gat aac agc cga aca cca atg cag tgg  1392
Glu Val Arg Met Thr Ser Arg Asp Asn Ser Arg Thr Pro Met Gln Trp
                420                 425                 430 aac gac tct gtt aat gcc gga ttc acc cag ggc aaa ccc tgg ttt cac  1440
Asn Asp Ser Val Asn Ala Gly Phe Thr Gln Gly Lys Pro Trp Phe His
            435                 440                 445 ctc aat ccc aac tat aag caa atc aat gcc gcc agg gng gtg aat aaa  1488
Leu Asn Pro Asn Tyr Lys Gln Ile Asn Ala Ala Arg Xaa Val Asn Lys
        450                 455                 460 ccc gac tcg gta ttc agt tac tac cgt caa ctg atc aac ctg cgt cac  1536
Pro Asp Ser Val Phe Ser Tyr Tyr Arg Gln Leu Ile Asn Leu Arg His
465                 470                 475 cag atc ccg gca ctg acc agt ggt gaa tac cgt gat ctc gat ccg cag  1584
Gln Ile Pro Ala Leu Thr Ser Gly Glu Tyr Arg Asp Leu Asp Pro Gln
480                 485                 490                 495 aat aac cag gtc tat gcc tat acc cgt ata ctg gat aat gaa aaa tat  1632
Asn Asn Gln Val Tyr Ala Tyr Thr Arg Ile Leu Asp Asn Glu Lys Tyr
                500                 505                 510 ctg gtg gta gtt aat ttt aaa cct gag cag ctg cat tac gct ctg cca  1680
Leu Val Val Val Asn Phe Lys Pro Glu Gln Leu His Tyr Ala Leu Pro
            515                 520                 525 gat aat ctg act att gcc agc agt ctg ctg gaa aat gtc cac caa cca  1728
Asp Asn Leu Thr Ile Ala Ser Ser Leu Leu Glu Asn Val His Gln Pro
        530                 535                 540 tca ctg caa gaa aat gcc tcc acg ctg act ctt gct ccg tgg caa gcc  1776
Ser Leu Gln Glu Asn Ala Ser Thr Leu Thr Leu Ala Pro Trp Gln Ala
545                 550                 555 ggg atc tat aag ctg aac tga                                      1797
Gly Ile Tyr Lys Leu Asn
560                 565

<210> SEQ ID NO 8
<211> LENGTH: 598
<212> TYPE: PRT
<213> ORGANISM: Unknown Organism
<220> FEATURE:
<223> OTHER INFORMATION: Description of Unknown Organism: Bacterial
      isolate 68J
<220> FEATURE:
<221> NAME/KEY: MOD_RES
<222> LOCATION: (460)
<223> OTHER INFORMATION: Any amino acid

<400> SEQUENCE: 8

Met Phe Leu Asn Gly Phe Lys Thr Val Ile Ala Leu Thr Met Ala Ser
            -30                 -25                 -20

Ser Phe Tyr Leu Ala Ala Ser Pro Leu Thr Lys Pro Ser Thr Pro Ile
        -15                 -10                 -5

Ala Ala Thr Asn Ile Gln Lys Ser Ala Asp Phe Pro Ile Trp Trp Lys
 -1   1               5                  10                  15

Gln Ala Val Phe Tyr Gln Ile Tyr Pro Arg Ser Phe Lys Asp Ser Asn
                20                  25                  30

Gly Asp Gly Ile Gly Asp Ile Pro Gly Ile Ile Glu Lys Leu Asp Tyr
            35                  40                  45

-continued

```
Leu Lys Met Leu Gly Val Asp Ala Ile Trp Ile Asn Pro His Tyr Glu
        50                  55                  60

Ser Pro Asn Thr Asp Asn Gly Tyr Asp Ile Ser Asp Tyr Arg Lys Ile
    65                  70                  75

Met Lys Glu Tyr Gly Ser Met Ala Asp Phe Asp Arg Leu Val Ala Glu
80                  85                  90                  95

Met Asn Lys Arg Gly Met Arg Leu Met Ile Asp Ile Val Ile Asn His
                100                 105                 110

Thr Ser Asp Arg His Arg Trp Phe Val Gln Ser Arg Ser Gly Lys Asp
            115                 120                 125

Asn Pro Tyr Arg Asp Tyr Tyr Phe Trp Arg Asp Gly Lys Gln Gly Gln
        130                 135                 140

Ala Pro Asn Asn Tyr Pro Ser Phe Phe Gly Gly Ser Ala Trp Gln Leu
    145                 150                 155

Asp Lys Gln Thr Asp Gln Tyr Tyr Leu His Tyr Phe Ala Pro Gln Gln
160                 165                 170                 175

Pro Asp Leu Asn Trp Asp Asn Pro Lys Val Arg Ala Glu Leu Tyr Asp
                180                 185                 190

Ile Leu Arg Phe Trp Leu Asp Lys Gly Val Ser Gly Leu Arg Phe Asp
            195                 200                 205

Thr Val Ala Thr Phe Ser Lys Ile Pro Gly Phe Pro Asp Leu Ser Lys
        210                 215                 220

Ala Gln Leu Lys Asn Phe Ala Glu Ala Tyr Thr Glu Gly Pro Asn Ile
    225                 230                 235

His Lys Tyr Ile His Glu Met Asn Arg Gln Val Leu Ser Lys Tyr Asn
240                 245                 250                 255

Val Ala Thr Ala Gly Glu Ile Phe Gly Val Pro Val Ser Ala Met Pro
                260                 265                 270

Asp Tyr Phe Asp Arg Arg Arg Glu Glu Leu Asn Ile Ala Phe Thr Phe
            275                 280                 285

Asp Leu Ile Arg Leu Asp Arg Tyr Pro Asp Gln Arg Trp Arg Arg Lys
        290                 295                 300

Pro Trp Thr Leu Ser Gln Phe Arg Gln Val Ile Ser Gln Thr Asp Arg
    305                 310                 315

Ala Ala Gly Glu Phe Gly Trp Asn Ala Phe Phe Leu Asp Asn His Asp
320                 325                 330                 335

Asn Pro Arg Gln Val Ser His Phe Gly Asp Asp Ser Pro Gln Trp Arg
                340                 345                 350

Glu Arg Ser Ala Lys Ala Leu Ala Thr Leu Leu Leu Thr Gln Arg Ala
            355                 360                 365

Thr Pro Phe Ile Phe Gln Gly Ala Glu Leu Gly Met Thr Asn Tyr Pro
        370                 375                 380

Phe Lys Asn Ile Glu Glu Phe Asp Asp Ile Glu Val Lys Gly Phe Trp
    385                 390                 395

Asn Asp Tyr Val Ala Ser Gly Lys Val Asn Ala Ala Glu Phe Leu Gln
400                 405                 410                 415

Glu Val Arg Met Thr Ser Arg Asp Asn Ser Arg Thr Pro Met Gln Trp
                420                 425                 430

Asn Asp Ser Val Asn Ala Gly Phe Thr Gln Gly Lys Pro Trp Phe His
            435                 440                 445

Leu Asn Pro Asn Tyr Lys Gln Ile Asn Ala Ala Arg Xaa Val Asn Lys
        450                 455                 460
```

```
Pro Asp Ser Val Phe Ser Tyr Tyr Arg Gln Leu Ile Asn Leu Arg His
    465                 470                 475

Gln Ile Pro Ala Leu Thr Ser Gly Glu Tyr Arg Asp Leu Asp Pro Gln
480                 485                 490                 495

Asn Asn Gln Val Tyr Ala Tyr Thr Arg Ile Leu Asp Asn Glu Lys Tyr
                500                 505                 510

Leu Val Val Asn Phe Lys Pro Glu Gln Leu His Tyr Ala Leu Pro
            515                 520                 525

Asp Asn Leu Thr Ile Ala Ser Ser Leu Leu Glu Asn Val His Gln Pro
            530                 535                 540

Ser Leu Gln Glu Asn Ala Ser Thr Leu Thr Leu Ala Pro Trp Gln Ala
    545                 550                 555

Gly Ile Tyr Lys Leu Asn
560             565

<210> SEQ ID NO 9
<211> LENGTH: 1698
<212> TYPE: DNA
<213> ORGANISM: Unknown Organism
<220> FEATURE:
<223> OTHER INFORMATION: Description of Unknown Organism: Bacterial
      isolate 68J
<220> FEATURE:
<221> NAME/KEY: CDS
<222> LOCATION: (1)..(1695)
<220> FEATURE:
<221> NAME/KEY: mat_peptide
<222> LOCATION: (1)..(1698)
<220> FEATURE:
<221> NAME/KEY: modified_base
<222> LOCATION: (1379)
<223> OTHER INFORMATION: a, t, c, g, other or unknown

<400> SEQUENCE: 9 gca acg aat ata caa aag tcc gct gat ttt ccc att tgg tgg aaa cag      48
Ala Thr Asn Ile Gln Lys Ser Ala Asp Phe Pro Ile Trp Trp Lys Gln
  1               5                  10                  15 gca gta ttt tac cag att tat ccc cgc tca ttt aaa gat agc aat ggt      96
Ala Val Phe Tyr Gln Ile Tyr Pro Arg Ser Phe Lys Asp Ser Asn Gly
             20                  25                  30 gat ggt atc ggc gat att ccc ggt atc att gag aaa ctg gac tat tta     144
Asp Gly Ile Gly Asp Ile Pro Gly Ile Ile Glu Lys Leu Asp Tyr Leu
         35                  40                  45 aaa atg ctg gga gtt gat gct atc tgg ata aac ccg cac tat gag tct     192
Lys Met Leu Gly Val Asp Ala Ile Trp Ile Asn Pro His Tyr Glu Ser
 50                  55                  60 cct aac acc gac aat ggt tac gat att agt gat tat cgt aaa atc atg     240
Pro Asn Thr Asp Asn Gly Tyr Asp Ile Ser Asp Tyr Arg Lys Ile Met
 65                  70                  75                  80 aag gag tac ggc agc atg gct gac ttt gac cgt ctg gtt gcc gaa atg     288
Lys Glu Tyr Gly Ser Met Ala Asp Phe Asp Arg Leu Val Ala Glu Met
                 85                  90                  95 aat aaa cgt ggt atg cgc ctg atg att gat att gtt atc aat cat acc     336
Asn Lys Arg Gly Met Arg Leu Met Ile Asp Ile Val Ile Asn His Thr
            100                 105                 110 agc gat cgt cac cgc tgg ttt gtg cag agc cgt tca ggt aaa gat aat     384
Ser Asp Arg His Arg Trp Phe Val Gln Ser Arg Ser Gly Lys Asp Asn
        115                 120                 125 cct tac cgc gac tat tat ttc tgg cgt gat ggt aaa cag gga cag gct     432
Pro Tyr Arg Asp Tyr Tyr Phe Trp Arg Asp Gly Lys Gln Gly Gln Ala
    130                 135                 140 ccc aat aac tat ccc tct ttc ttt ggc ggt tca gcc tgg caa ctg gat     480
```

```
Pro Asn Asn Tyr Pro Ser Phe Gly Gly Ser Ala Trp Gln Leu Asp
145                 150                 155                 160 aaa cag act gac cag tat tat ctg cac tat ttt gca cca cag cag ccg       528
Lys Gln Thr Asp Gln Tyr Tyr Leu His Tyr Phe Ala Pro Gln Gln Pro
                165                 170                 175 gat ctg aac tgg gat aac cca aaa gtt cgg gct gaa ctc tac gat att       576
Asp Leu Asn Trp Asp Asn Pro Lys Val Arg Ala Glu Leu Tyr Asp Ile
            180                 185                 190 ctg cgt ttc tgg ctg gat aaa ggc gta tcc gga cta cgt ttt gat acc       624
Leu Arg Phe Trp Leu Asp Lys Gly Val Ser Gly Leu Arg Phe Asp Thr
        195                 200                 205 gtg gct act ttc tcc aaa att cct ggc ttc ccg gac ctg tca aaa gcg       672
Val Ala Thr Phe Ser Lys Ile Pro Gly Phe Pro Asp Leu Ser Lys Ala
    210                 215                 220 cag ctg aag aat ttt gcc gaa gct tat act gag ggg ccg aat att cat       720
Gln Leu Lys Asn Phe Ala Glu Ala Tyr Thr Glu Gly Pro Asn Ile His
225                 230                 235                 240 aaa tat atc cat gaa atg aac cgc cag gta ctg tct aaa tat aat gtt       768
Lys Tyr Ile His Glu Met Asn Arg Gln Val Leu Ser Lys Tyr Asn Val
                245                 250                 255 gcc acc gct ggt gaa atc ttc ggt gtg cca gtg agt gct atg ccg gat       816
Ala Thr Ala Gly Glu Ile Phe Gly Val Pro Val Ser Ala Met Pro Asp
            260                 265                 270 tat ttt gac cgg cgg cgt gaa gaa ctc aat att gct ttc acc ttt gat       864
Tyr Phe Asp Arg Arg Arg Glu Glu Leu Asn Ile Ala Phe Thr Phe Asp
        275                 280                 285 ttg atc agg ctc gat cgt tat ccc gat cag cgc tgg cgt cgt aaa cca       912
Leu Ile Arg Leu Asp Arg Tyr Pro Asp Gln Arg Trp Arg Arg Lys Pro
    290                 295                 300 tgg aca tta agc cag ttt cgt caa gtt atc tct cag act gac cgt gcc       960
Trp Thr Leu Ser Gln Phe Arg Gln Val Ile Ser Gln Thr Asp Arg Ala
305                 310                 315                 320 gcc ggt gaa ttt ggc tgg aac gcc ttt ttc ctt gat aac cat gat aac      1008
Ala Gly Glu Phe Gly Trp Asn Ala Phe Phe Leu Asp Asn His Asp Asn
                325                 330                 335 ccg cgc cag gtc tca cac ttt ggt gac gac agc cca caa tgg cgc gaa      1056
Pro Arg Gln Val Ser His Phe Gly Asp Asp Ser Pro Gln Trp Arg Glu
            340                 345                 350 cgc tcg gca aaa gca ctg gca acg ctg ctg ctg acg cag cgt gcc acg      1104
Arg Ser Ala Lys Ala Leu Ala Thr Leu Leu Leu Thr Gln Arg Ala Thr
        355                 360                 365 ccg ttt atc ttt cag ggg gcg gag ttg gga atg act aat tac ccc ttt      1152
Pro Phe Ile Phe Gln Gly Ala Glu Leu Gly Met Thr Asn Tyr Pro Phe
    370                 375                 380 aaa aat ata gag gaa ttt gat gat att gag gtt aaa ggc ttc tgg aac      1200
Lys Asn Ile Glu Glu Phe Asp Asp Ile Glu Val Lys Gly Phe Trp Asn
385                 390                 395                 400 gac tat gta gcc agc gga aaa gta aac gct gct gaa ttt tta cag gag      1248
Asp Tyr Val Ala Ser Gly Lys Val Asn Ala Ala Glu Phe Leu Gln Glu
                405                 410                 415 gtt cgc atg acc agc cgc gat aac agc cga aca cca atg cag tgg aac      1296
Val Arg Met Thr Ser Arg Asp Asn Ser Arg Thr Pro Met Gln Trp Asn
            420                 425                 430 gac tct gtt aat gcc gga ttc acc cag ggc aaa ccc tgg ttt cac ctc      1344
Asp Ser Val Asn Ala Gly Phe Thr Gln Gly Lys Pro Trp Phe His Leu
        435                 440                 445 aat ccc aac tat aag caa atc aat gcc gcc agg nng gtg aat aaa ccc      1392
Asn Pro Asn Tyr Lys Gln Ile Asn Ala Ala Arg Xaa Val Asn Lys Pro
    450                 455                 460
```

-continued

```
gac tcg gta ttc agt tac tac cgt caa ctg atc aac ctg cgt cac cag      1440
Asp Ser Val Phe Ser Tyr Tyr Arg Gln Leu Ile Asn Leu Arg His Gln
465                 470                 475                 480 atc ccg gca ctg acc agt ggt gaa tac cgt gat ctc gat ccg cag aat      1488
Ile Pro Ala Leu Thr Ser Gly Glu Tyr Arg Asp Leu Asp Pro Gln Asn
                485                 490                 495 aac cag gtc tat gcc tat acc cgt ata ctg gat aat gaa aaa tat ctg      1536
Asn Gln Val Tyr Ala Tyr Thr Arg Ile Leu Asp Asn Glu Lys Tyr Leu
            500                 505                 510 gtg gta gtt aat ttt aaa cct gag cag ctg cat tac gct ctg cca gat      1584
Val Val Val Asn Phe Lys Pro Glu Gln Leu His Tyr Ala Leu Pro Asp
        515                 520                 525 aat ctg act att gcc agc agt ctg ctg gaa aat gtc cac caa cca tca      1632
Asn Leu Thr Ile Ala Ser Ser Leu Leu Glu Asn Val His Gln Pro Ser
530                 535                 540 ctg caa gaa aat gcc tcc acg ctg act ctt gct ccg tgg caa gcc ggg      1680
Leu Gln Glu Asn Ala Ser Thr Leu Thr Leu Ala Pro Trp Gln Ala Gly
545                 550                 555                 560 atc tat aag ctg aac tga                                              1698
Ile Tyr Lys Leu Asn
                565
```

<210> SEQ ID NO 10
<211> LENGTH: 565
<212> TYPE: PRT
<213> ORGANISM: Unknown Organism
<220> FEATURE:
<223> OTHER INFORMATION: Description of Unknown Organism: Bacterial
      isolate 68J
<220> FEATURE:
<221> NAME/KEY: MOD_RES
<222> LOCATION: (460)
<223> OTHER INFORMATION: Any amino acid

<400> SEQUENCE: 10

```
Ala Thr Asn Ile Gln Lys Ser Ala Asp Phe Pro Ile Trp Trp Lys Gln
  1               5                  10                  15

Ala Val Phe Tyr Gln Ile Tyr Pro Arg Ser Phe Lys Asp Ser Asn Gly
             20                  25                  30

Asp Gly Ile Gly Asp Ile Pro Gly Ile Ile Glu Lys Leu Asp Tyr Leu
         35                  40                  45

Lys Met Leu Gly Val Asp Ala Ile Trp Ile Asn Pro His Tyr Glu Ser
     50                  55                  60

Pro Asn Thr Asp Asn Gly Tyr Asp Ile Ser Asp Tyr Arg Lys Ile Met
 65                  70                  75                  80

Lys Glu Tyr Gly Ser Met Ala Asp Phe Asp Arg Leu Val Ala Glu Met
                 85                  90                  95

Asn Lys Arg Gly Met Arg Leu Met Ile Asp Ile Val Ile Asn His Thr
            100                 105                 110

Ser Asp Arg His Arg Trp Phe Val Gln Ser Arg Ser Gly Lys Asp Asn
        115                 120                 125

Pro Tyr Arg Asp Tyr Tyr Phe Trp Arg Asp Gly Lys Gln Gly Gln Ala
    130                 135                 140

Pro Asn Asn Tyr Pro Ser Phe Phe Gly Gly Ser Ala Trp Gln Leu Asp
145                 150                 155                 160

Lys Gln Thr Asp Gln Tyr Tyr Leu His Tyr Phe Ala Pro Gln Gln Pro
                165                 170                 175

Asp Leu Asn Trp Asp Asn Pro Lys Val Arg Ala Glu Leu Tyr Asp Ile
            180                 185                 190
```

```
Leu Arg Phe Trp Leu Asp Lys Gly Val Ser Gly Leu Arg Phe Asp Thr
            195                 200                 205

Val Ala Thr Phe Ser Lys Ile Pro Gly Phe Pro Asp Leu Ser Lys Ala
        210                 215                 220

Gln Leu Lys Asn Phe Ala Glu Ala Tyr Thr Glu Gly Pro Asn Ile His
225                 230                 235                 240

Lys Tyr Ile His Glu Met Asn Arg Gln Val Leu Ser Lys Tyr Asn Val
                245                 250                 255

Ala Thr Ala Gly Glu Ile Phe Gly Val Pro Val Ser Ala Met Pro Asp
            260                 265                 270

Tyr Phe Asp Arg Arg Glu Glu Leu Asn Ile Ala Phe Thr Phe Asp
        275                 280                 285

Leu Ile Arg Leu Asp Arg Tyr Pro Asp Gln Arg Trp Arg Arg Lys Pro
        290                 295                 300

Trp Thr Leu Ser Gln Phe Arg Gln Val Ile Ser Gln Thr Asp Arg Ala
305                 310                 315                 320

Ala Gly Glu Phe Gly Trp Asn Ala Phe Phe Leu Asp Asn His Asp Asn
            325                 330                 335

Pro Arg Gln Val Ser His Phe Gly Asp Asp Ser Pro Gln Trp Arg Glu
                340                 345                 350

Arg Ser Ala Lys Ala Leu Ala Thr Leu Leu Leu Thr Gln Arg Ala Thr
            355                 360                 365

Pro Phe Ile Phe Gln Gly Ala Glu Leu Gly Met Thr Asn Tyr Pro Phe
        370                 375                 380

Lys Asn Ile Glu Glu Phe Asp Asp Ile Glu Val Lys Gly Phe Trp Asn
385                 390                 395                 400

Asp Tyr Val Ala Ser Gly Lys Val Asn Ala Ala Glu Phe Leu Gln Glu
                405                 410                 415

Val Arg Met Thr Ser Arg Asp Asn Ser Arg Thr Pro Met Gln Trp Asn
            420                 425                 430

Asp Ser Val Asn Ala Gly Phe Thr Gln Gly Lys Pro Trp Phe His Leu
        435                 440                 445

Asn Pro Asn Tyr Lys Gln Ile Asn Ala Ala Arg Xaa Val Asn Lys Pro
        450                 455                 460

Asp Ser Val Phe Ser Tyr Tyr Arg Gln Leu Ile Asn Leu Arg His Gln
465                 470                 475                 480

Ile Pro Ala Leu Thr Ser Gly Glu Tyr Arg Asp Leu Asp Pro Gln Asn
                485                 490                 495

Asn Gln Val Tyr Ala Tyr Thr Arg Ile Leu Asp Asn Glu Lys Tyr Leu
            500                 505                 510

Val Val Val Asn Phe Lys Pro Glu Gln Leu His Tyr Ala Leu Pro Asp
        515                 520                 525

Asn Leu Thr Ile Ala Ser Ser Leu Leu Glu Asn Val His Gln Pro Ser
530                 535                 540

Leu Gln Glu Asn Ala Ser Thr Leu Thr Leu Ala Pro Trp Gln Ala Gly
545                 550                 555                 560

Ile Tyr Lys Leu Asn
                565

<210> SEQ ID NO 11
<211> LENGTH: 99
<212> TYPE: DNA
<213> ORGANISM: Unknown Organism
<220> FEATURE:
<223> OTHER INFORMATION: Description of Unknown Organism: Bacterial
```

```
                isolate 68J
<220> FEATURE:
<221> NAME/KEY: CDS
<222> LOCATION: (1)..(99)
<220> FEATURE:
<221> NAME/KEY: sig_peptide
<222> LOCATION: (1)..(99)

<400> SEQUENCE: 11 atg ttt ctt aat gga ttt aag aca gtt att gct ctg act atg gca agc        48
Met Phe Leu Asn Gly Phe Lys Thr Val Ile Ala Leu Thr Met Ala Ser
 1               5                  10                  15 tcg ttt tat ctt gcc gcc agc ccg tta act aag cca tcg acc cct att        96
Ser Phe Tyr Leu Ala Ala Ser Pro Leu Thr Lys Pro Ser Thr Pro Ile
                20                  25                  30 gcc                                                                    99
Ala

<210> SEQ ID NO 12
<211> LENGTH: 33
<212> TYPE: PRT
<213> ORGANISM: Unknown Organism
<220> FEATURE:
<223> OTHER INFORMATION: Description of Unknown Organism: Bacterial
      isolate 68J

<400> SEQUENCE: 12

Met Phe Leu Asn Gly Phe Lys Thr Val Ile Ala Leu Thr Met Ala Ser
 1               5                  10                  15

Ser Phe Tyr Leu Ala Ala Ser Pro Leu Thr Lys Pro Ser Thr Pro Ile
                20                  25                  30

Ala

<210> SEQ ID NO 13
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 13
ggatccaaca atggcaacga atatacaaaa gtcc                                  34

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 14
ataggtacct cagttcagct tatagatccc                                       30

<210> SEQ ID NO 15
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 15
ggatccaaca atggcaaccg ttcagcaatc aaatg                                 35

<210> SEQ ID NO 16
<211> LENGTH: 28
```

-continued

```
<212> TYPE: DNA
<213> ORGANISM: Artificial Sequence
<220> FEATURE:
<223> OTHER INFORMATION: Description of Artificial Sequence: Primer

<400> SEQUENCE: 16
ataggtacct tacttaaacg cgtggatg                                          28

<210> SEQ ID NO 17
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 17
ggatccaaca atggcaaccg ttcacaagga aagtg                                  35

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 18
ataggtacct taccgcagct tatacacacc                                        30

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Sucrose
      isomerase consensus sequence

<400> SEQUENCE: 19

Asp Leu Ile Arg Leu Asp Arg
 1               5

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence: Sucrose
      isomerase consensus sequence
<220> FEATURE:
<221> NAME/KEY: MOD_RES
<222> LOCATION: (7)
<223> OTHER INFORMATION: Any amino acid

<400> SEQUENCE: 20

Glu Val Lys Gly Phe Trp Xaa Asp Tyr Val
 1               5                  10

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Sucrose
      isomerase consensus sequence

<400> SEQUENCE: 21

Arg Pro Gln Trp Arg Glu
 1               5
```

```
<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence: Sucrose
      isomerase consensus sequence

<400> SEQUENCE: 22

Ser Pro Gln Trp Arg Glu
 1               5

<210> SEQ ID NO 23
<211> LENGTH: 13
<212> TYPE: PRT
<213> ORGANISM: Artificial Sequence
<220> FEATURE:
<223> OTHER INFORMATION: Description of Artificial Sequence: Sucrose
      isomerase consensus sequence

<400> SEQUENCE: 23

Pro Asn Asn Tyr Pro Ser Phe Phe Gly Gly Ser Ala Trp
 1               5                  10

<210> SEQ ID NO 24
<211> LENGTH: 16
<212> TYPE: PRT
<213> ORGANISM: Artificial Sequence
<220> FEATURE:
<223> OTHER INFORMATION: Description of Artificial Sequence: Sucrose
      isomerase consensus sequence
<220> FEATURE:
<221> NAME/KEY: MOD_RES
<222> LOCATION: (8)..(9)
<223> OTHER INFORMATION: Any amino acid

<400> SEQUENCE: 24

Gln Tyr Tyr Leu His Tyr Phe Xaa Xaa Gln Gln Pro Asp Leu Asn Trp
 1               5                  10                  15

<210> SEQ ID NO 25
<211> LENGTH: 594
<212> TYPE: DNA
<213> ORGANISM: Erwinia rhapontici
<220> FEATURE:
<221> NAME/KEY: CDS
<222> LOCATION: (1)..(594)
<220> FEATURE:
<221> NAME/KEY: modified_base
<222> LOCATION: (42)
<223> OTHER INFORMATION: a, t, c, g, other or unknown

<400> SEQUENCE: 25 tac gtt gaa aca ggc aaa gtg aaa gct gag gaa ttc ctt can aac gta        48
Tyr Val Glu Thr Gly Lys Val Lys Ala Glu Glu Phe Leu Thr Asn Val
 1               5                  10                  15 cgc caa acc agc cgt gat aac agc aga acc ccc ttc cag tgg gat gca        96
Arg Gln Thr Ser Arg Asp Asn Ser Arg Thr Pro Phe Gln Trp Asp Ala
             20                  25                  30 agc aaa aat gcg ggc ttt acc agc gga acc cct tgg tta aaa atc aat       144
Ser Lys Asn Ala Gly Phe Thr Ser Gly Thr Pro Trp Leu Lys Ile Asn
         35                  40                  45 ccc aat tat aaa gaa atc aac agc gca gat cag att aac aat cca aat       192
Pro Asn Tyr Lys Glu Ile Asn Ser Ala Asp Gln Ile Asn Asn Pro Asn
     50                  55                  60 tcc gta ttt aac tat tat aga aag ctc att aac att cgc cac gac atc       240
Ser Val Phe Asn Tyr Tyr Arg Lys Leu Ile Asn Ile Arg His Asp Ile
```

```
                    65                  70                  75                  80
cct gcc tta acc tac ggc agt tat att gat tta gct cct gac aac aat         288
Pro Ala Leu Thr Tyr Gly Ser Tyr Ile Asp Leu Ala Pro Asp Asn Asn
                    85                  90                  95 tca gtc tat gct tac act cga acg ttt ggc gct gaa aaa tat ctt gtg         336
Ser Val Tyr Ala Tyr Thr Arg Thr Phe Gly Ala Glu Lys Tyr Leu Val
                100                 105                 110 gtc att aat ttt aaa gaa gaa gtg atg cac tac acc ctg cct ggg gat         384
Val Ile Asn Phe Lys Glu Glu Val Met His Tyr Thr Leu Pro Gly Asp
            115                 120                 125 tta tcc atc aat aag gtg att act gaa aac aac agt cac act att gtg         432
Leu Ser Ile Asn Lys Val Ile Thr Glu Asn Asn Ser His Thr Ile Val
        130                 135                 140 aat aaa aat gac gta gaa gat cct cgt ggg gct aca agc gtt tgt agc         480
Asn Lys Asn Asp Val Glu Asp Pro Arg Gly Ala Thr Ser Val Cys Ser
145                 150                 155                 160 ccc ttc cag gct caa aaa agg cct ggc gac ccg ggt tac tct gct gcc         528
Pro Phe Gln Ala Gln Lys Arg Pro Gly Asp Pro Gly Tyr Ser Ala Ala
                165                 170                 175 cat tcg att cgg ttc ttg ccc cgg ttt ttc gct tca tac agg ggc gac         576
His Ser Ile Arg Phe Leu Pro Arg Phe Phe Ala Ser Tyr Arg Gly Asp
            180                 185                 190 atc cac gcg ttt aag taa                                                 594
Ile His Ala Phe Lys
        195

<210> SEQ ID NO 26
<211> LENGTH: 197
<212> TYPE: PRT
<213> ORGANISM: Erwinia rhapontici

<400> SEQUENCE: 26

Tyr Val Glu Thr Gly Lys Val Lys Ala Glu Glu Phe Leu Thr Asn Val
  1               5                  10                  15

Arg Gln Thr Ser Arg Asp Asn Ser Arg Thr Pro Phe Gln Trp Asp Ala
             20                  25                  30

Ser Lys Asn Ala Gly Phe Thr Ser Gly Thr Pro Trp Leu Lys Ile Asn
         35                  40                  45

Pro Asn Tyr Lys Glu Ile Asn Ser Ala Asp Gln Ile Asn Asn Pro Asn
     50                  55                  60

Ser Val Phe Asn Tyr Tyr Arg Lys Leu Ile Asn Ile Arg His Asp Ile
 65                  70                  75                  80

Pro Ala Leu Thr Tyr Gly Ser Tyr Ile Asp Leu Ala Pro Asp Asn Asn
                 85                  90                  95

Ser Val Tyr Ala Tyr Thr Arg Thr Phe Gly Ala Glu Lys Tyr Leu Val
            100                 105                 110

Val Ile Asn Phe Lys Glu Glu Val Met His Tyr Thr Leu Pro Gly Asp
        115                 120                 125

Leu Ser Ile Asn Lys Val Ile Thr Glu Asn Asn Ser His Thr Ile Val
    130                 135                 140

Asn Lys Asn Asp Val Glu Asp Pro Arg Gly Ala Thr Ser Val Cys Ser
145                 150                 155                 160

Pro Phe Gln Ala Gln Lys Arg Pro Gly Asp Pro Gly Tyr Ser Ala Ala
                165                 170                 175

His Ser Ile Arg Phe Leu Pro Arg Phe Phe Ala Ser Tyr Arg Gly Asp
            180                 185                 190

Ile His Ala Phe Lys
        195
```

```
<210> SEQ ID NO 27
<211> LENGTH: 21
<212> TYPE: DNA
<213> ORGANISM: Erwinia rhapontici

<400> SEQUENCE: 27
gatctgatca gactcgatcg t                                              21

<210> SEQ ID NO 28
<211> LENGTH: 30
<212> TYPE: DNA
<213> ORGANISM: Erwinia rhapontici

<400> SEQUENCE: 28
gaggtgaaag gttttggca agactacgtt                                      30

<210> SEQ ID NO 29
<211> LENGTH: 18
<212> TYPE: DNA
<213> ORGANISM: Erwinia rhapontici

<400> SEQUENCE: 29
cgaccacaat ggcgcgag                                                  18

<210> SEQ ID NO 30
<211> LENGTH: 39
<212> TYPE: DNA
<213> ORGANISM: Erwinia rhapontici

<400> SEQUENCE: 30
cccaataact atccctcctt cttcggtggc tcagcctgg                           39

<210> SEQ ID NO 31
<211> LENGTH: 48
<212> TYPE: DNA
<213> ORGANISM: Erwinia rhapontici

<400> SEQUENCE: 31
cagtattacc tccattactt tgccaaacag caacccgacc tcaactgg                 48

<210> SEQ ID NO 32
<211> LENGTH: 21
<212> TYPE: DNA
<213> ORGANISM: Unknown Organism
<220> FEATURE:
<223> OTHER INFORMATION: Description of Unknown Organism: Bacterial
      isolate 68J

<400> SEQUENCE: 32
gatctgatca gactcgatcg t                                              21

<210> SEQ ID NO 33
<211> LENGTH: 30
<212> TYPE: DNA
<213> ORGANISM: Unknown Organism
<220> FEATURE:
<223> OTHER INFORMATION: Description of Unknown Organism: Bacterial
      isolate 68J

<400> SEQUENCE: 33
gaggtgaaag gttttggca agactacgtt                                      30
```

```
<210> SEQ ID NO 34
<211> LENGTH: 18
<212> TYPE: DNA
<213> ORGANISM: Unknown Organism
<220> FEATURE:
<223> OTHER INFORMATION: Description of Unknown Organism: Bacterial
      isolate 68J

<400> SEQUENCE: 34
cgaccacaat ggcgcgag                                                     18

<210> SEQ ID NO 35
<211> LENGTH: 39
<212> TYPE: DNA
<213> ORGANISM: Unknown Organism
<220> FEATURE:
<223> OTHER INFORMATION: Description of Unknown Organism: Bacterial
      isolate 68J

<400> SEQUENCE: 35
cccaataact atccctcctt cttcggtggc tcagcctgg                              39

<210> SEQ ID NO 36
<211> LENGTH: 48
<212> TYPE: DNA
<213> ORGANISM: Unknown Organism
<220> FEATURE:
<223> OTHER INFORMATION: Description of Unknown Organism: Bacterial
      isolate 68J

<400> SEQUENCE: 36
cagtattacc tccattactt tgccaaacag caacccgacc tcaactgg                    48

<210> SEQ ID NO 37

<400> SEQUENCE: 37

000

<210> SEQ ID NO 38
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 38
tggtggaarg argctgt                                                      17

<210> SEQ ID NO 39
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 39
tcccagttag rtccggctg                                                    19

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40
```

Asp Leu Ile Arg Leu Asp Arg
 1               5

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
gayytvatym gdywygatcg h                                              21

<210> SEQ ID NO 42
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)
<223> OTHER INFORMATION: Any amino acid

<400> SEQUENCE: 42

Glu Val Lys Gly Phe Trp Xaa Asp Tyr Val
 1               5                  10

<210> SEQ ID NO 43
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)
<223> OTHER INFORMATION: a, t, c, g, other or unknown

<400> SEQUENCE: 43
gaggtbaaag gyttytggma ngaytay                                        27

<210> SEQ ID NO 44
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Arg or Ser

<400> SEQUENCE: 44

Xaa Pro Gln Trp Arg Glu
 1               5

<210> SEQ ID NO 45
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 45
mgvccrcaat ggssbgar                                                18

<210> SEQ ID NO 46
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Pro Asn Asn Tyr Pro Ser Phe Phe Gly Gly Ser Ala Trp
 1               5                  10

<210> SEQ ID NO 47
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
cchaayaayt ayccytchtt yttyggyggy tcrgcvtgg                         39

<210> SEQ ID NO 48
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Ala or Gly
<220> FEATURE:
<221> NAME/KEY: MOD_RES
<222> LOCATION: (9)
<223> OTHER INFORMATION: Any amino acid

<400> SEQUENCE: 48

Gln Tyr Tyr Leu His Tyr Phe Xaa Xaa Gln Gln Pro Asp Leu Asn Trp
 1               5                  10                  15

<210> SEQ ID NO 49
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
cartaytayy trcaytaytt ygsymvwcag                                   30

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 50
agagtttgat cctggctcag                                              20
```

```
<210> SEQ ID NO 51
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 51
ggttaccttg ttacgactt                                                    19

<210> SEQ ID NO 52
<211> LENGTH: 6
<212> TYPE: PRT
<213> ORGANISM: Artificial Sequence
<220> FEATURE:
<223> OTHER INFORMATION: Description of Artificial Sequence: 6X-His tag

<400> SEQUENCE: 52

His His His His His His
  1               5
```

ISOMALTULOSE SYNTHASES, POLYNUCLEOTIDES ENCODING THEM AND USES THEREFOR

This application is a continuation-in-part application of co-pending International Patent Application No. PCT/AU01/01084 filed Aug. 29, 2001, which designates the United States, and which claims priority of Australian Patent Application No. PQ 9768 filed Aug. 29, 2000.

BACKGROUND OF THE INVENTION

This invention relates generally to enzymes that convert sucrose to isomaltulose. More particularly, the present invention relates to novel sucrose isomerases, to polynucleotides encoding these enzymes, to methods for isolating such polynucleotides and to nucleic acid constructs that express these polynucleotides. The invention also relates to cells, particularly transformed bacterial or plant cells, and to differentiated plants comprising cells, which express these polynucleotides. The invention further relates to the use of the polypeptides, polynucleotides, cells and plants of the invention for producing isomaltulose.

Isomaltulose α-D-glucopyranosyl-1,6-D-fructofuranose (also called palatinose) is a naturally occurring structural isomer of sucrose (α-D-glucosyl-1,2-D-fructose). Isomaltulose is a nutritive disaccharide, with sweetness and bulk similar to sucrose. Several characteristics make isomaltulose advantageous over sucrose for some applications in the food industry: 1) noncariogenic (not causing dental decay); 2) low glycemic index (useful for diabetics); 3) selective promotion of growth of beneficial bifidobacteria among human intestinal microflora; 4) greater stability of isomaltulose-containing foods and beverages; 5) less hygroscopic; 6) simple conversion into sugar alcohols with other useful properties as foods. The safety of isomaltulose has been comprehensively verified, resulting in unqualified approval as human food, and it is widely used commercially as a sucrose substitute in foods, soft drinks and medicines (Takazoe, 1989, Palatinose—an isomeric alternative to sucrose. In: Progress in Sweeteners (T H Grengy, ed.) pp 143–167. Elsevier, Barking, UK).

Furthermore, because isomaltulose has an accessible carbonyl group, it has attracted attention as a renewable starting material for the manufacture of bioproducts such as polymers and surfactants with potential advantages over substances manufactured from petroleum (Cartarius et al., 2001, Chemical Engineering and Technology 24: 55A–59A; Kunz, 1993, From sucrose to semisynthetical polymers. In: Carbohydrates as Organic Raw Materials II (G Descotes, ed.) pp 135–161. VCH, Weinheim; Lichtenthaler et al., 2001, Green Chemistry 3: 201–209; Schiweck et al., 1991, New developments in the use of sucrose as an industrial bulk chemical. In: Carbohydrates as Organic Raw Materials (FW Lichtenthaler, ed.) pp 57–94. VCH, Weinheim).

Commercial isomaltulose is produced from food-grade sucrose by enzymatic rearrangement from a (1,2)-fructoside to a (1,6)-fructoside followed by crystallization. Sucrose isomerase (SI) enzymes (also known as isomaltulose synthases), which are able to convert sucrose to isomaltulose, have been demonstrated in *Protaminobacter rubrum, Erwinia rhapontici, E. carotovora* var *atroseptica, Serratia plymuthica, S. marcesens, Pseudomonas mesoacidophila, Leuconostoc mesenteroides, Klebsiella* spp., *Agrobacterium* sp., haploid yeast and *Enterobacter* sp. (Avigad 1959, *Biochemical Journal* 73: 587–593; Bornke et al., 2001, *Journal of Bacteriology* 183: 2425–2430; Cheetham et al., 1982 *Nature* 299: 628–631; Huang et al., 1998, *Journal of Industrial Microbiology & Biotechnology* 21: 22–27; Lund and Waytt, 1973, *Journal of General Microbiology* 78: 331–3; Mattes et al., 1998, U.S. Pat. No. 5,786,140; McAllister et al., 1990, *Biotechnology Letters* 12: 667–672; Miyata et al., 1992, *Bioscience Biotechnology and Biochemistry* 56: 1680–1681; Munir et al., 1987, *Carbohydrate Research* 164: 477–485; Nagai et al., 1994, *Bioscience Biotechnology and Biochemistry* 58: 1789–1793; Nagai-Miyata et al., 1993, *Bioscience Biotechnology and Biochemistry* 57: 2049–2053; Park et al., 1996, *Revista De Microbiology* 27: 131–136; Schmidt-Berg-Lorenz and Maunch, 1964, *Zeitung fur die Zuckerindustrie* 14: 625–627; Stotola et al., 1956, *Journal of the American Chemical Society* 78: 2514–2518; Tsuyuki et al., 1992, *Journal of General and Applied Microbiology* 38: 483–490; Zhang et al., 2002, *Applied and Environmental Microbiology* 68: 2676–2682). Isomaltulose is currently produced in industrial scale column reactors containing immobilized bacterial cells. Initially, natural isolates have been used for this purpose but it is anticipated that higher yields of isomaltulose may be achieved using recombinant techniques. Mattes et al. (1998, supra) disclose isolated polynucleotides from *Protaminobacter rubrum* (CBS 547, 77), *Erwinia rhapontici* (NCPPB 1578), the microorganism SZ 62 (*Enterobacter* species) and the microorganism MX-45 (*Pseudomonas mesoacidophila* FERM 11808 or FERM BP 3619) for producing recombinant partial or full-length sucrose isomerase enzymes in host cells such as *Escherichia coli*. Mattes et al. also disclose conserved amino acid sequences for designing degenerate oligonucleotides for cloning sucrose isomerase-encoding polynucleotides by the polymerase chain reaction (PCR).

In addition to isomaltulose, reported SIs produce varying proportions of the isomer trehalulose (1-O-α-D-glucopyranosyl-D-fructose) along with glucose and fructose as by-products. Some purified SIs produce predominantly isomaltulose (75–85%), others predominantly trehalulose (90%). The ratio of these products varies with reaction conditions, particularly temperature and pH, and under some conditions small quantities of other products such as isomaltose and isomelezitose may be formed (Véronèse and Perlot, 1999, *Enzyme and Microbial Technology* 24: 263–269). The formation of multiple products lowers the yield and complicates the recovery of the desired isomer. Slow conversion of sucrose into isomaltulose, and a narrow range of optimal reaction conditions also limit the industrial efficiency of isomaltulose production (Cheetham, 1984, *Biochemical Journal* 220: 213–220; Schiweck et al., 1990, *Zuckerindustrie* 115: 555–565.). An ideal SI would show high speed, complete conversion, high specificity and a wide window of reaction conditions for isomaltulose production.

SUMMARY OF THE INVENTION

In work leading up to the present invention, degenerate oligonucleotides, based on the conserved amino acid sequences disclosed by Mattes et al., were used to amplify sucrose isomerase-encoding polynucleotides by PCR from *Erwinia rhapontici* (Accession Number WAC2928), and from 30 independent sucrose-isomerase negative bacterial isolates. The PCR amplification yielded multiple DNA products from most tested bacteria. However, these products were found not to encode sucrose isomerase. Nucleic acid sequence analysis of 12 separate PCR products, including 6 products amplified from *Erwinia rhapontici*, revealed that none of the DNA products displayed significant sequence similarity to sucrose isomerase genes. Instead, most of these products showed high sequence similarity to known glucosidase genes. It was concluded, therefore, that the conserved sequences of Mattes et al. were not specific to sucrose isomerases, but were common to other classes of enzymes including glucosidases.

Notwithstanding the above, the present inventors developed a novel functional screening assay for the isolation and characterisation of novel polynucleotides encoding isomaltulose-producing sucrose isomerase enzymes. Several such novel polynucleotides were cloned using this assay and some of these were found to encode polypeptides with superior sucrose isomerase activity relative to those disclosed by Mattes et al. Comparison of the deduced polypeptide sequences with known sucrose isomerase or glucosidase polypeptide sequences revealed a number of conserved motifs, which are unique to sucrose isomerases, and which could therefore be used inter alia for designing sucrose isomerase-specific oligonucleotides. Such oligonucleotides are advantageous in that they provide for the first time facile isolation of sucrose isomerase-encoding polynucleotides using nucleic acid amplification techniques.

The inventors have reduced the above discoveries to practice in new isolated molecules, as well as cells and plants, for producing isomaltulose, as described hereinafter.

Accordingly, in one aspect of the invention, there is provided a method for isolating a polynucleotide that encodes an isomaltulose-producing sucrose isomerase enzyme, the method comprising:
(a) obtaining an environmental sample from a location in which organisms, capable of converting sucrose to isomaltulose, have a selective advantage;
(b) screening for organisms that produce isomaltulose from sucrose; and
(c) isolating a polynucleotide that encodes an isomaltulose-producing sucrose isomerase enzyme from an isomaltulose-producing organism using a probe specific for sucrose isomerase-encoding polynucleotides or an antigen-binding molecule specific for sucrose isomerase enzymes, wherein the probe hybridises under at least low stringency conditions to sucrose isomerase-encoding polynucleotides but does not hybridise under the same conditions to glucosidase-encoding polynucleotides, and wherein the antigen-binding molecule is immuno-interactive with sucrose isomerase enzymes but is not immuno-interactive with glucosidases.

Suitably, the polynucleotide is isolated using a probe that consists essentially of a nucleic acid sequence which corresponds or is complementary to a nucleotide sequence encoding a sucrose isomerase consensus sequence set forth in any one of SEQ ID NO: 19, 20, 21, 22, 23 and 24, or variant thereof which preferably has at least 80% sequence identity thereto.

The nucleotide sequence suitably comprises the sequence set forth in any one of SEQ ID NO: 27, 28, 29, 30, 31, 32, 33, 34, 35 and 36 or nucleotide sequence variant thereof which preferably has at least 60% sequence identity thereto.

Preferably, the nucleotide sequence variant is capable of hybridising to any one of the sequences identified by SEQ ID NO: 27, 28, 29, 30, 31, 32, 33, 34, 35 and 36 under at least low stringency conditions.

Suitably, the polynucleotide is isolated using an antigen-binding molecule that is immuno-interactive specifically with an amino acid sequence selected from SEQ ID NO: 19, 20, 21, 22, 23 or 24 or a variant of said sequence having at least 80% sequence identity thereto.

Preferably, the method further comprises selecting or otherwise enriching for dual sucrose- and isomaltulose-metabolising organisms which are capable of using both sucrose and isomaltulose as carbon sources for growth.

Suitably, the screening utilises an assay that quantifies isomaltulose production by an organism.

In another aspect of the invention, there is provided an isolated polypeptide comprising:
(a) the amino acid sequence set forth in SEQ ID NO: 8 or 10; or
(b) a biologically active fragment of (a) which is at least 20 amino acids in length; or
(c) a variant of (a) having at least 75% sequence identity thereto; or
(d) a derivative of any one of (a) to (c).

Preferably, the variant has at least at least 80%, more preferably at least 85%, more preferably at least 90% and still more preferably at least 95%, 96%, 97%, 98% or 99% sequence identity to any one of the amino acid sequences set forth in SEQ ID NO: 8 and 10.

Preferably, the variant comprises the consensus sequence set forth in any one or more of SEQ ID NO: 19, 20, 21, 22, 23 and 24 or variant thereof.

Suitably, said consensus sequence variant has at least 80%, preferably at least 85%, more preferably at least 90%, and still more preferably at least 95%, 96%, 97%, 98% or 99% sequence identity to any one of the amino acid sequences set forth in SEQ ID NO: 19, 20, 21, 22, 23 and 24.

In one embodiment, the polypeptide, fragment variant or derivative converts at least about 86% of sucrose to isomaltulose. In another embodiment, the polypeptide, fragment variant or derivative converts sucrose to trehalulose at a rate of less than about 5% of the yield of isomaltulose produced by the same polypeptide, fragment variant or derivative. In yet another embodiment, the polypeptide, fragment variant or derivative converts sucrose to isomaltulose with a $K_m$ of less than about 50 mM. In still another embodiment, the polypeptide, fragment variant or derivative converts sucrose to isomaltulose with a $V_{max}$ of more than about 400 µmoles isomaltulose/mg protein/min.

In another aspect, the invention provides an isolated polynucleotide encoding a polypeptide as broadly described above. Preferably, the polynucleotide comprises:
(i) the nucleotide sequence set forth in SEQ ID NO: 7 and 9; or
(ii) a biologically active fragment of (a) which is at least 60 nucleotides in length; or
(iii) a polynucleotide variant of (a) having at least 70% sequence identity thereto.

In one embodiment, the polynucleotide variant has at least 80%, more preferably at least 85%, even more preferably at least 90%, and still even more preferably at least 95%, 96%, 97%, 98% or 99% sequence identity to any one of the polynucleotides set forth in SEQ ID NO: 7 and 9.

In another embodiment, the polynucleotide variant is capable of hybridising to any one of the polynucleotides identified by SEQ ID NO: 7 or 9 under at least low stringency conditions, preferably under at least medium stringency conditions, and more preferably under high stringency conditions.

Preferably, the polynucleotide variant comprises a nucleotide sequence encoding a consensus sequence set forth in any one or more of SEQ ID NO: 19, 20, 21, 22, 23 and 24.

Suitably, the consensus sequence is encoded by a nucleotide sequence set forth in any one of SEQ ID NO: 27, 28, 29, 30, 31, 32, 33, 34, 35 and 36 or nucleotide sequence variant thereof.

In one embodiment, the nucleotide sequence variant has at least 70%, more preferably at least 80%, and still more preferably at least 90% sequence identity to any one of the sequences set forth in SEQ ID NO: 27, 28, 29, 30, 31, 32, 33, 34, 35 and 36.

In another embodiment, the nucleotide sequence variant is capable of hybridising to any one of the sequences identified by SEQ ID NO: 27, 28, 29, 30, 31, 32, 33, 34, 35 and 36 under at least low stringency conditions, preferably under at least medium stringency conditions, and more preferably under high stringency conditions.

In another aspect, the invention features an expression vector comprising a polynucleotide as broadly described above wherein the polynucleotide is operably linked to a regulatory polynucleotide.

In a further aspect, the invention provides a host cell containing a said expression vector.

Suitably, the host cell is a bacterium or other prokaryote, or a plant cell or other eukaryote.

Preferably, the plant is sugarcane (Saccharum sp.) or another species capable of synthesising and/or accumulating sucrose (e.g. sugar beet).

Another aspect of the present invention contemplates an isolated cell, or isolated population of cells, which produce(s) a polypeptide comprising:
 (a) the amino acid sequence set forth in SEQ ID NO: 8 or 10; or
 (b) a biologically active fragment of (a) which is at least 20 amino acids in length; or
 (c) a variant of (a) having at least 75% sequence identity thereto; or
 (d) a derivative of any one of (a) to (c).

Preferably, the cell population is homogeneous.

Suitably, the cell population is in the form of a culture.

The polypeptide produced by the cell or cell population preferably comprises a polynucleotide comprising: (i) the nucleotide sequence set forth in SEQ ID NO: 7 and 9; or (ii) a biologically active fragment of (a) which is at least 60 nucleotides in length; or (iii) a polynucleotide variant of (a) having at least 70% sequence identity thereto.

The invention also features a method of producing a recombinant polypeptide, fragment, variant or derivative as broadly described above, comprising:
 culturing a host cell containing an expression vector as broadly described above such that the recombinant polypeptide, fragment, variant or derivative is expressed from said polynucleotide; and
 isolating the recombinant polypeptide, fragment, variant or derivative.

In another aspect, the invention provides a method of producing a biologically active fragment of a polypeptide as broadly described above, comprising:
 detecting sucrose isomerase activity associated with a fragment of a polypeptide according to any one of SEQ ID NO: 8 or 10, which indicates that said fragment is a biologically active fragment.

In a further aspect, the invention provides a method of producing a biologically active fragment as broadly described above, comprising:
 introducing a polynucleotide, from which a fragment of a polypeptide according to any one of SEQ ID NO: 8 or 10 can be produced, into a cell; and
 detecting sucrose isomerase activity, which indicates that said fragment is a biologically active fragment.

In yet a further aspect, the invention provides a method of producing a polypeptide variant of a parent polypeptide comprising the sequence set forth in any one of SEQ ID NO: 8 or 10, or biologically active fragment thereof, comprising:
 producing a modified polypeptide whose sequence is distinguished from the parent polypeptide by substitution, deletion or addition of at least one amino acid; and
 detecting sucrose isomerase activity associated with the modified polypeptide, which indicates that said modified polypeptide is a polypeptide variant.

In a further aspect, the invention contemplates a method of producing a polypeptide variant of a parent polypeptide comprising the sequence set forth in any one of SEQ ID NO: 8 or 10, or biologically active fragment thereof, comprising:
 producing a polynucleotide from which a modified polypeptide as described above can be produced;
 introducing the polynucleotide into a cell; and
 detecting sucrose isomerase activity, which indicates that the modified polypeptide is a polypeptide variant.

According to another aspect of the invention, there is provided a method for producing isomaltulose from sucrose, said method comprising contacting sucrose or a sucrose-containing substrate with the polypeptide, fragment, variant or derivative as broadly described above, or with an isolated cell or host cell as broadly described above, or an extract thereof, for a time and under conditions sufficient to produce isomaltulose.

In another aspect, the invention resides in an antigen-binding molecule that is specifically immuno-interactive with said polypeptide, fragment, variant or derivative according to the present invention.

In yet another aspect, the invention provides an antigen-binding molecule that is immuno-interactive with a sucrose isomerase but is not immuno-interactive with a glucosidase.

Preferably, said antigen-binding molecule is immuno-interactive with any one of the amino acid sequences set forth in SEQ ID NO: 19, 20, 21, 22, 23 and 24.

Another aspect of the invention provides a method for detecting a specific polypeptide or polynucleotide, comprising detecting the sequence of:
 (a) SEQ ID NO: 8 or 10, or a biologically active fragment thereof at least 20 amino acids in length, or a variant of these having at least 75% sequence identity thereto; or
 (b) a polynucleotide encoding (a).

In a preferred embodiment, the sequence of (b) is selected from SEQ ID NO: 7 or 9, or a biologically active fragment thereof at least 60 nucleotides in length, or a polynucleotide variant of these having at least 70% sequence identity thereto.

According to another aspect of the invention, there is provided a method of detecting a sucrose isomerase in a sample, comprising:
 contacting the sample with an antigen-binding molecule as broadly described above; and
 detecting the presence of a complex comprising the said antigen-binding molecule and the said polypeptide, fragment, variant or derivative in said contacted sample.

In yet another aspect, there is provided a method for detecting a polypeptide, fragment, variant or derivative as broadly described above, comprising:
 detecting expression in a cell of a polynucleotide encoding said polypeptide, fragment, variant or derivative as broadly described above.

In still another aspect, the invention provides a probe for interrogating nucleic acid for the presence of a sucrose isomerase-encoding polynucleotide, comprising a nucleotide sequence which hybridises under at least low stringency conditions to sucrose isomerase-encoding polynucleotides but which does not hybridise under the same conditions to glucosidase-encoding polynucleotides.

Preferably, the probe consists essentially of a nucleic acid sequence which corresponds or is complementary to a nucleotide sequence encoding a sucrose isomerase consensus sequence set forth in any one of SEQ ID NO: 19, 20, 21, 22, 23 and 24.

Still a further aspect of the invention provides a probe comprising a nucleotide sequence which is capable of hybridising to at least a portion of a nucleotide sequence encoding SEQ ID NO: 8 and 10 under at least low stringency conditions, preferably under at least medium stringency conditions, and more preferably under high stringency conditions.

In a preferred embodiment, the probe comprises a nucleotide sequence which is capable of hybridising to at least a portion of SEQ ID NO: 7 and 9 under at least low stringency conditions.

According to another aspect of the invention, there is provided a transformed plant cell containing an expression vector as broadly described above.

In a preferred embodiment, the plant is sugarcane (Saccharum sp.).

In a still further aspect, the invention provides a differentiated plant comprising plant cells containing an expression vector as broadly described above.

In yet another aspect, the invention provides isomaltulose harvested from a differentiated plant as broadly described above.

BRIEF DESCRIPTION OF THE DRAWINGS

FIG. 3 presents the nucleotide sequence (SEQ ID NO: 1) of sucrose isomerase cloned from *Erwinia rhapontici*.

FIG. 4 presents the nucleotide sequence (SEQ ID NO: 7) of sucrose isomerase cloned from 68J.

FIG. 5 presents the predicted amino acid sequence (SEQ ID NO: 2) of sucrose isomerase cloned from *Erwinia rhapontici*.

FIG. 6 presents the predicted amino acid sequence (SEQ ID NO: 8) of sucrose isomerase cloned from 68J.

Figure 1:
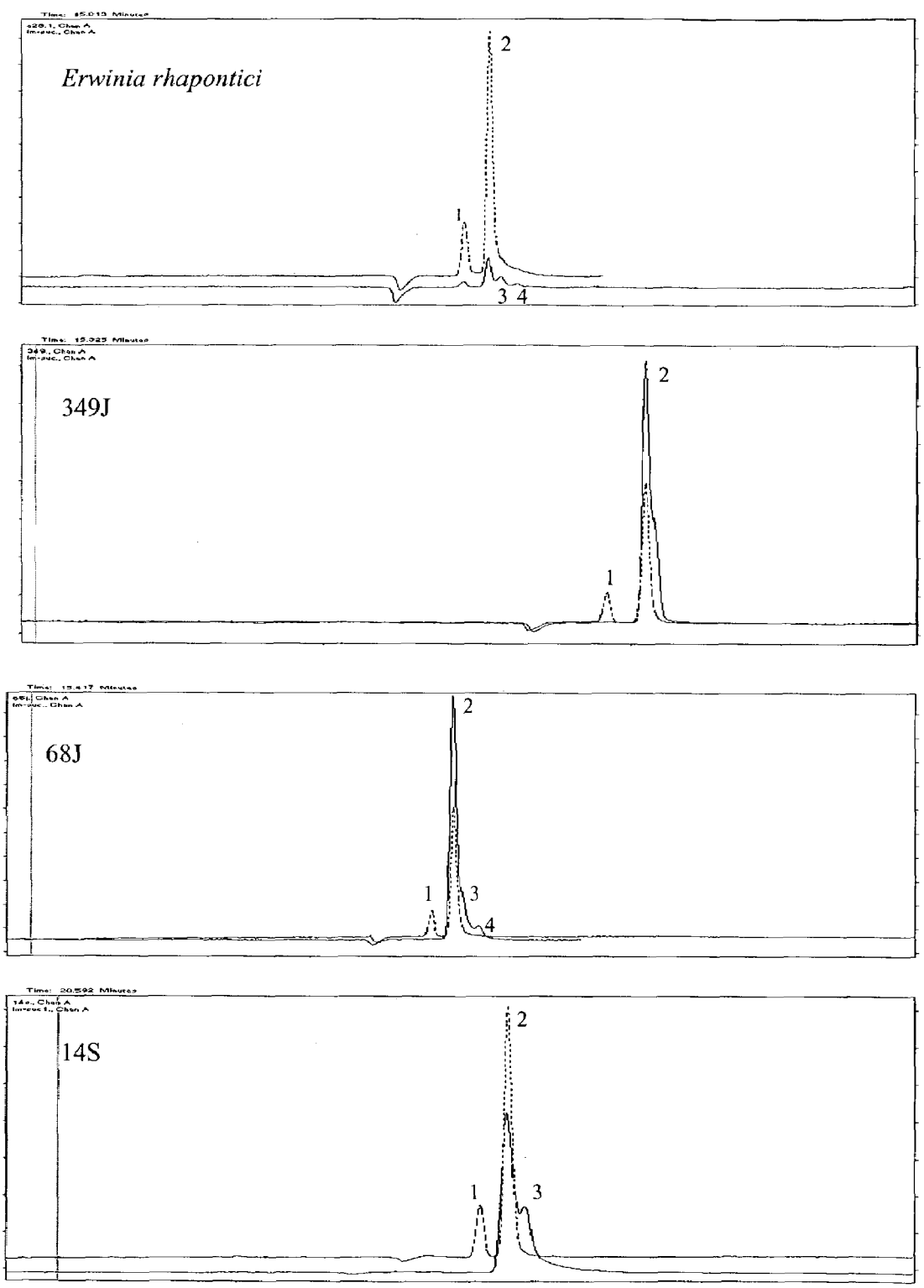
FIG. 1 is a graphical representation showing the conversion of sucrose to isomaltulose in isolated bacteria. Peaks: 1—sucrose, 2—isomaltulose, 3—fructose, 4—glucose. "Dotted" electrophoretogram is sucrose and isomaltulose standards.

BRIEF DESCRIPTION OF THE SEQUENCES:
SUMMARY TABLE

TABLE A

| Sequence ID Number | Sequence | Length |
| --- | --- | --- |
| SEQ ID NO: 1 | Full-length sucrose isomerase coding sequence from *Erwinia rhapontici* (Accession No. WAC2928) | 1899 bases |
| SEQ ID NO: 2 | Full-length sucrose isomerase polypeptide sequence from *Erwinia rhapontici* (Accession No. WAC2928) | 632 residues |
| SEQ ID NO: 3 | Polynucleotide sequence encoding mature sucrose isomerase from *Erwinia rhapontici* (Accession No. WAC2928) | 1791 bases |
| SEQ ID NO: 4 | Mature sucrose isomerase polypeptide sequence from *Erwinia rhapontici* (Accession No. WAC2928) | 596 residues |
| SEQ ID NO: 5 | Signal peptide coding sequence relating to sucrose isomerase from *Erwinia rhapontici* (Accession No. WAC2928) | 108 bases |
| SEQ ID NO: 6 | Signal peptide relating to sucrose isomerase from *Erwinia rhapontici* (Accession No. WAC2928) | 36 residues |
| SEQ ID NO: 7 | Full-length sucrose isomerase coding sequence from bacterial isolate 68J | 1797 bases |
| SEQ ID NO: 8 | Full-length sucrose isomerase polypeptide sequence from bacterial isolate 68J | 598 residues |
| SEQ ID NO: 9 | Polynucleotide sequence encoding mature sucrose isomerase from bacterial isolate 68J | 1698 bases |
| SEQ ID NO: 10 | Mature sucrose isomerase polypeptide sequence from bacterial isolate 68J | 565 residues |
| SEQ ID NO: 11 | Signal peptide coding sequence relating to sucrose isomerase from bacterial isolate 68J | 99 bases |
| SEQ ID NO: 12 | Signal peptide relating to sucrose isomerase from bacterial isolate 68J | 33 residues |
| SEQ ID NO: 13 | 5' oligonucleotide primer for amplification of 68J isolate | 34 bases |
| SEQ ID NO: 14 | 3' oligonucleotide primer for amplification of 68J isolate | 30 bases |
| SEQ ID NO: 15 | 5' oligonucleotide primer for amplification of *Erwinia rhapontici* (Accession No. WAC2928) | 35 bases |
| SEQ ID NO: 16 | 3' oligonucleotide primer for amplification of *Erwinia rhapontici* (Accession No. WAC2928) | 28 bases |
| SEQ ID NO: 17 | 5' oligonucleotide primer for amplification of 14S isolate | 35 bases |
| SEQ ID NO. 18 | 3' oligonucleotide primer for amplification of 14S isolate | 30 bases |
| SEQ ID NO: 19 | Sucrose isomerase consensus sequence | 7 residues |
| SEQ ID NO: 20 | Sucrose isomerase consensus sequence | 10 residues |
| SEQ ID NO: 21 | Sucrose isomerase consensus sequence | 6 residues |
| SEQ ID NO: 22 | Sucrose isomerase consensus sequence | 6 residues |
| SEQ ID NO: 23 | Sucrose isomerase consensus sequence | 13 residues |
| SEQ ID NO: 24 | Sucrose isomerase consensus sequence | 16 residues |
| SEQ ID NO: 25 | Polynucleotide sequence encoding carboxyl terminal portion of sucrose isomerase from *Erwinia rhapontici* (Accession No. WAC2928) | 594 bases |
| SEQ ID NO: 26 | Polypeptide sequence of carboxyl terminal portion of sucrose isomerase from *Erwinia rhapontici* (Accession No. WAC2928) | 197 residues |
| SEQ ID NO: 27 | Sub-sequence of SEQ ID NO: 1 encoding consensus sequence set forth in SEQ ID NO: 19 | 21 bases |
| SEQ ID NO: 28 | Sub-sequence of SEQ ID NO: 1 encoding consensus sequence set forth in SEQ ID NO: 20 | 30 bases |
| SEQ ID NO: 29 | Sub-sequence of SEQ ID NO: 1 encoding consensus sequence set forth in SEQ ID NO: 21 | 18 bases |
| SEQ ID NO: 30 | Sub-sequence of SEQ ID NO: 1 encoding consensus sequence set forth in SEQ ID NO: 23 | 39 bases |
| SEQ ID NO: 31 | Sub-sequence of SEQ ID NO: 1 encoding consensus sequence set forth in SEQ ID NO: 24 | 48 bases |
| SEQ ID NO: 32 | Sub-sequence of SEQ ID NO: 7 encoding consensus sequence set forth in SEQ ID NO: 19 | 21 bases |
| SEQ ID NO: 33 | Sub-sequence of SEQ ID NO: 7 encoding consensus sequence set forth in SEQ ID NO: 20 | 30 bases |
| SEQ ID NO: 34 | Sub-sequence of SEQ ID NO: 7 encoding consensus sequence set forth in SEQ ID NO: 21 | 18 bases |
| SEQ ID NO: 35 | Sub-sequence of SEQ ID NO: 7 encoding consensus sequence set forth in SEQ ID NO: 23 | 39 bases |
| SEQ ID NO: 36 | Sub-sequence of SEQ ID NO: 7 encoding consensus sequence set forth in SEQ ID NO: 24 | 48 bases |
| SEQ ID NO: 37 | Geysen library peptide | 8 residues |
| SEQ ID NO: 38 | Mattes-based forward primer | 17 bases |
| SEQ ID NO: 39 | Mattes-based reverse primer | 19 bases |
| SEQ ID NO: 40 | Conserved sucrose isomerase element aa 321–321 | 7 residues |
| SEQ ID NO: 41 | Oligonucleotide encoding SEQ ID NO: 40 | 21 bases |
| SEQ ID NO: 42 | Conserved sucrose isomerase element aa 427–436 | 10 residues |
| SEQ ID NO: 43 | Oligonucleotide encoding SEQ ID NO: 42 | 30 bases |
| SEQ ID NO: 44 | Conserved sucrose isomerase element aa 380–385 | 6 residues |

TABLE A-continued

| Sequence ID Number | Sequence | Length |
|---|---|---|
| SEQ ID NO: 45 | Oligonucleotide encoding SEQ ID NO: 44 | 18 bases |
| SEQ ID NO: 46 | Conserved sucrose isomerase element aa 178–191 | 13 residues |
| SEQ ID NO: 47 | Oligonucleotide encoding SEQ ID NO: 46 | 39 bases |
| SEQ ID NO: 48 | Conserved sucrose isomerase element 198–213 | 16 residues |
| SEQ ID NO: 49 | Oligonucleotide encoding sequence contained within SEQ ID NO: 48 | 30 bases |

DETAILED DESCRIPTION OF THE INVENTION

1. Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e. to at least one) of the grammatical object of the article. By way of example, "an element" means one element or more than one element.

The term "about" is used herein to refer to sequences that vary by as much as 30%, preferably by as much as 20% and more preferably by as much as 10% to the length of a reference quantity, level, value, dimension, length, position, size, or amount.

"Amplification product" refers to a nucleic acid product generated by nucleic acid amplification techniques.

By "antigen-binding molecule" is meant a molecule that has binding affinity for a target antigen. It will be understood that this term extends to immunoglobulins, immunoglobulin fragments and non-immunoglobulin derived protein frameworks that exhibit antigen-binding activity.

As used herein, the term "binds specifically" and the like refers to antigen-binding molecules that bind the polypeptide or polypeptide fragments of the invention but do not significantly bind to homologous prior art polypeptides.

By "biologically active fragment" is meant a fragment of a full-length parent polypeptide which fragment retains the activity of the parent polypeptide. In one embodiment, a biologically active fragment has sucrose isomerase activity, which converts sucrose to isomaltulose. In another embodiment, a biologically active fragment is an immuno-interactive fragment as defined below. As used herein, the term "biologically active fragment" includes deletion mutants and small peptides, for example of at least 8, preferably at least 10, more preferably at least 20, and still more preferably at least 30 contiguous amino acids, which comprise the above activities. Peptides of this type may be obtained through the application of standard recombinant nucleic acid techniques or synthesised using conventional liquid or solid phase synthesis techniques. For example, reference may be made to solution synthesis or solid phase synthesis as described, for example, in Chapter 9 entitled "Peptide Synthesis" by Atherton and Shephard which is included in a publication entitled "Synthetic Vaccines" edited by Nicholson and published by Blackwell Scientific Publications. Alternatively, peptides can be produced by digestion of a polypeptide of the invention with proteinases such as endoLys-C, endoArg-C, endoGlu-C and staphylococcus V8-protease. The digested fragments can be purified by, for example, high performance liquid chromatographic (HPLC) techniques.

Throughout this specification, unless the context requires otherwise, the words "comprise", "comprises" and "comprising" will be understood to imply the inclusion of a stated step or element or group of steps or elements but not the exclusion of any other step or element or group of steps or elements.

By "corresponds to" or "corresponding to" is meant a polynucleotide (a) having a nucleotide sequence that is substantially identical or complementary to all or a portion of a reference polynucleotide sequence or (b) encoding an amino acid sequence identical to an amino acid sequence in a peptide or protein. This phrase also includes within its scope a peptide or polypeptide having an amino acid sequence that is substantially identical to a sequence of amino acids in a reference peptide or protein.

By "derivative" is meant a polypeptide that has been derived from the basic sequence by modification, for example by conjugation or complexing with other chemical moieties or by post-translational modification techniques as would be understood in the art. The term "derivative" also includes within its scope alterations that have been made to a parent sequence including additions, or deletions that provide for functionally equivalent molecules. Accordingly, the term derivative encompasses molecules that will have sucrose isomerase activity.

"Homology" refers to the inference of an evolutionary relationship based on amino acid sequence similarity. "Hybridisation" is used herein to denote the pairing of complementary nucleotide sequences to produce a DNA-DNA hybrid or a DNA-RNA hybrid. Complementary base sequences are those sequences that are related by the base-pairing rules. In DNA, A pairs with T and C pairs with G. In RNA U pairs with A and C pairs with G. In this regard, the terms "match" and "mismatch" as used herein refer to the hybridisation potential of paired nucleotides in complementary nucleic acid strands. Matched nucleotides hybridise efficiently, such as the classical A-T and G-C base pair mentioned above. Mismatches are other combinations of nucleotides that do not hybridise efficiently.

Reference herein to "immuno-interactive" includes reference to any interaction, reaction, or other form of association between molecules and in particular where one of the molecules is, or mimics, a component of the immune system.

By "immuno-interactive fragment" is meant a fragment of the polypeptide set forth in SEQ ID NO: 8 or 10, which fragment elicits an immune response, including the production of elements that specifically bind to said polypeptide, or variant or derivative thereof. As used herein, the term "immuno-interactivefragment" includes deletion mutants and small peptides, for example of at least six, preferably at least 8 and more preferably at least 20 contiguous amino acids, which comprise antigenic determinants or epitopes. Several such fragments may be joined together.

By "isolated" is meant material that is substantially or essentially free from components that normally accompany it in its native state. For example, an "isolated polynucleotide", as used herein, refers to a polynucleotide, which has been purified from the sequences which flank it in a naturally occurring state, e.g., a DNA fragment which has been removed from the sequences which are normally adjacent to the fragment.

By "marker gene" is meant a gene that imparts a distinct phenotype to cells expressing the marker gene and thus allows such transformed cells to be distinguished from cells that do not have the marker. A selectable marker gene confers a trait for which one can 'select' based on resistance to a selective agent (e.g., a herbicide, antibiotic, radiation, heat, or other treatment damaging to untransformed cells). A screenable marker gene (or reporter gene) confers a trait that one can identify through observation or testing, i.e., by 'screening' (e.g. β-glucuronidase, luciferase, or other enzyme activity not present in untransformed cells).

By "obtained from" is meant that a sample such as, for example, a nucleic acid extract or polypeptide extract is isolated from, or derived from, a particular source. For example, the extract may be isolated directly from any sucrose-metabolising organism, preferably from a sucrose-metabolising microorganism, more preferably from microorganisms of the genera *Agrobacterium, Enterobacter, Erwinia, Klebsiella, Leuconostoc, Protaminobacter, Pseudomonas* and *Serratia* or from a microorganism obtained from a location in which organisms, capable of converting sucrose to isomaltulose, have a selective advantage as for example described herein.

The term "oligonucleotide" as used herein refers to a polymer composed of a multiplicity of nucleotide units (deoxyribonucleotides or ribonucleotides, or related structural variants or synthetic analogues thereof) linked via phosphodiester bonds (or related structural variants or synthetic analogues thereof). Thus, while the term "oligonucleotide" typically refers to a nucleotide polymer in which the nucleotides and linkages between them are naturally occurring, it will be understood that the term also includes within its scope various analogues including, but not restricted to, peptide nucleic acids (PNAs), phosphoramidates, phosphorothioates, methyl phosphonates, 2-O-methyl ribonucleic acids, and the like. The exact size of the molecule may vary depending on the particular application. An oligonucleotide is typically rather short in length, generally from about 10 to 30 nucleotides, but the term can refer to molecules of any length, although the term "polynucleotide" or "nucleic acid" is typically used for large oligonucleotides.

By "operably linked" is meant that transcriptional and translational regulatory nucleic acids are positioned relative to a polypeptide-encoding polynucleotide in such a manner that the polynucleotide is transcribed and optionally the polypeptide is translated.

As used herein, "plant" and "differentiated plant" refer to a whole plant or plant part containing differentiated plant cell types, tissues and/or organ systems. Plantlets and seeds are also included within the meaning of the foregoing terms. Plants included in the invention are any plants amenable to transformation techniques, including angiosperms, gymnosperms, monocotyledons and dicotyledons.

The term "plant cell" as used herein refers to protoplasts or other cells derived from plants, gamete-producing cells, and cells which regenerate into whole plants. Plant cells include cells in plants as well as protoplasts or other cells in culture.

By "plant tissue" is meant differentiated and undifferentiated tissue derived from roots, shoots, pollen, seeds, tumour tissue, such as crown galls, and various forms of aggregations of plant cells in culture, such as embryos and calluses.

"Constitutive promoter" refers to a promoter that directs expression of an operably linked transcribable sequence in many or all tissues of a plant.

By "stem-specific promoter" is meant a promoter that preferentially directs expression of an operably linked transcribable sequence in culm or stem tissue of a plant, as compared to expression in leaf, root or other tissues of the plant.

The term "polynucleotide" or "nucleic acid" as used herein designates mRNA, RNA, cRNA, cDNA or DNA. The term typically refers to oligonucleotides greater than 30 nucleotides in length.

The terms "polynucleotide variant" and "variant" refer to polynucleotides displaying substantial sequence identity with a reference polynucleotide sequence or polynucleotides that hybridise with a reference sequence under stringent conditions that are defined hereinafter. These terms also encompass polynucleotides in which one or more nucleotides have been added or deleted, or replaced with different nucleotides. In this regard, it is well understood in the art that certain alterations inclusive of mutations, additions, deletions and substitutions can be made to a reference polynucleotide whereby the altered polynucleotide retains the biological function or activity of the reference polynucleotide. The terms "polynucleotide variant" and "variant" also include naturally occurring allelic variants.

"Polypeptide", "peptide" and "protein" are used interchangeably herein to refer to a polymer of amino acid residues and to variants and synthetic analogues of the same. Thus, these terms apply to amino acid polymers in which one or more amino acid residues is a synthetic non-naturally occurring amino acid, such as a chemical analogue of a corresponding naturally occurring amino acid, as well as to naturally-occurring amino acid polymers.

The term "polypeptide variant" refers to polypeptides in which one or more amino acids have been replaced by different amino acids. It is well understood in the art that some amino acids may be changed to others with broadly similar properties without changing the nature of the activity of the polypeptide (conservative substitutions) as described hereinafter. These terms also encompass polypeptides in which one or more amino acids have been added or deleted, or replaced with different amino acids. Accordingly, polypeptide variants as used herein encompass polypeptides that have sucrose isomerase activity.

By "primer" is meant an oligonucleotide which, when paired with a strand of DNA, is capable of initiating the synthesis of a primer extension product in the presence of a suitable polymerising agent. The primer is preferably single-stranded for maximum efficiency in amplification but may alternatively be double-stranded. A primer must be sufficiently long to prime the synthesis of extension products in the presence of the polymerisation agent. The length of the primer depends on many factors, including application, temperature to be employed, template reaction conditions, other reagents, and source of primers. For example, depending on the complexity of the target sequence, the oligonucleotide primer typically contains 15 to 35 or more nucleotides, although it may contain fewer nucleotides. Primers can be large polynucleotides, such as from about 200 nucleotides to several kilobases or more. Primers may be selected to be "substantially complementary" to the sequence on the template to which it is designed to hybridise and serve as a site for the initiation of synthesis. By "substantially complementary", it is meant that the primer is sufficiently complementary to hybridise with a target nucleotide sequence. Preferably, the primer contains no mismatches with the template to which it is designed to hybridise but this is not essential. For example, non-complementary nucleotides may be attached to the 5' end of the primer, with the remainder of the primer sequence being complementary to the template. Alternatively, non-complementary nucleotides or a stretch of non-complementary nucleotides can be interspersed into a primer, provided that the primer sequence has sufficient complementarity with the sequence of the template to hybridise therewith and thereby form a template for synthesis of the extension product of the primer.

"Probe" refers to a molecule that binds to a specific sequence or sub-sequence or other moiety of another molecule. Unless otherwise indicated, the term "probe" typically refers to a polynucleotide probe that binds to another nucleic acid, often called the "target nucleic acid", through complementary base pairing. Probes may bind target nucleic acids lacking complete sequence complementarity with the probe, depending on the stringency of the hybridisation conditions. Probes can be labelled directly or indirectly.

The term "recombinant polynucleotide" as used herein refers to a polynucleotide formed in vitro by the manipulation of nucleic acid into a form not normally found in nature. For example, the recombinant polynucleotide may be in the form of an expression vector. Generally, such expression vectors include transcriptional and translational regulatory nucleic acid operably linked to the nucleotide sequence.

By "recombinant polypeptide" is meant a polypeptide made using recombinant techniques, i.e., through the expression of a recombinant polynucleotide.

The term "regeneration" as used herein in relation to plant materials means growing a whole, differentiated plant from a plant cell, a group of plant cells, a plant part (including seeds), or a plant piece (e.g., from a protoplast, callus, or tissue part).

By "reporter molecule" as used in the present specification is meant a molecule that, by its chemical nature, provides an analytically identifiable signal that allows the detection of a complex comprising an antigen-binding molecule and its target antigen. The term "reporter molecule" also extends to use of cell agglutination or inhibition of agglutination such as red blood cells on latex beads, and the like.

Terms used to describe sequence relationships between two or more polynucleotides or polypeptides include "reference sequence", "comparison window", "sequence identity", "percentage of sequence identity" and "sequence similarity". A "reference sequence" is at least 12 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. In this way, sequences of a similar or substantially different length to those cited herein might be compared by insertion of gaps into the alignment. Optimal alignment of sequences for comparison may be conducted by computerised implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage sequence identity or sequence similarity over the comparison window) generated by any of the various methods selected. Reference also may be made to the BLAST family of programs as for example disclosed by Altschul et al., 1997, *Nucl. Acids Res.* 25:3389. A detailed discussion of sequence analysis can be found in Unit 19.3 of Ausubel et al., "Current Protocols in Molecular Biology", John Wiley & Sons Inc, 1994–1998, Chapter 15.

The term "sequence identity" as used herein refers to the extent that sequences are identical on a nucleotide-by-nucleotide basis or an amino acid-by-amino acid basis over a window of comparison. Thus, a "percentage of sequence identity" is calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. For the purposes of the present invention, "sequence identity" will be understood to mean the "match percentage" calculated by the DNASIS computer program (Version 2.5 for windows; available from Hitachi Software engineering Co., Ltd., South San Francisco, Calif., USA) using standard defaults as used in the reference manual accompanying the software.

The term "sequence similarity", in the context of actual or deduced amino acid sequences, refers to the output from comparison between sequences on an amino acid-by-amino acid basis; making an allowance for selected properties that are shared to differing degrees between different pairs of amino acids. Said allowance may be quantified through a matrix of binary or weighted amino acid similarity scores. Various similarity matrices have been proposed to reflect different hypothetical evolutionary, physical, chemical, structural or functional distances between amino acids. For the purposes of the present invention, a "percentage of sequence similarity" is calculated by comparing two optimally aligned sequences over the window of comparison, determined using sequence comparison program GAP (Deveraux et al. 1984, *Nucleic Acids Research* 12, 387–395), with a binary matrix derived from Table B infra of amino acid substitutions considered conservative for some functions within some polypeptides.

"Stringency" as used herein, refers to the temperature and ionic strength conditions, and presence or absence of certain organic solvents, during hybridisation and washing procedures. The higher the stringency, the higher will be the degree of complementarity between immobilised target nucleotide sequences and the labelled probe polynucleotide sequences that remain hybridised to the target after washing.

"Stringent conditions" refers to temperature and ionic conditions under which only nucleotide sequences having a high frequency of complementary bases will hybridise. The stringency required is nucleotide sequence dependent and depends upon the various components present during hybridisation and subsequent washes, and the time allowed for these processes. Generally, in order to maximise the hybridisation rate, non-stringent hybridisation conditions are selected; about 20 to 25° C. lower than the thermal melting point ($T_m$). The $T_m$ is the temperature at which 50% of specific target sequence hybridises to a perfectly complementary probe in solution at a defined ionic strength and pH. Generally, in order to require at least about 85% nucleotide complementarity of hybridised sequences, highly stringent washing conditions are selected to be about 5 to 15° C. lower than the $T_m$. In order to require at least about 70% nucleotide complementarity of hybridised sequences, moderately stringent washing conditions are selected to be about 16 to 30° C. lower than the $T_m$. Highly permissive (low stringency) washing conditions may be as low as 50° C. below the $T_m$, allowing a high level of mismatching between hybridised sequences. Those skilled in the art will recognise that other physical and chemical parameters in the hybridisation and wash stages can also be altered to affect the outcome of a detectable hybridisation signal from a specific level of complementarity between target and probe sequences. Other examples of stringency conditions are described in section 3.3.

The term "transformation" means alteration of the genotype of an organism, for example a bacterium or a plant, by the introduction of a foreign or endogenous nucleic acid.

By "transgenote" is meant an immediate product of a transformation process.

By "vector" is meant a nucleic acid molecule, preferably a DNA molecule derived, for example, from a plasmid, bacteriophage, or plant virus, into which a nucleic acid sequence may be inserted or cloned. A vector preferably contains one or more unique restriction sites and may be capable of autonomous replication in a defined host cell including a target cell or tissue or a progenitor cell or tissue thereof, or be integrable with the genome of the defined host such that the cloned sequence is reproducible. Accordingly, the vector may be an autonomously replicating vector, i.e., a vector that exists as an extrachromosomal entity, the replication of which is independent of chromosomal replication, e.g., a linear or closed circular plasmid, an extrachromosomal element, a minichromosome, or an artificial chromosome. The vector may contain any means for assuring self-replication. Alternatively, the vector may be one which, when introduced into a cell, is integrated into the genome of the recipient cell and replicated together with the chromosome(s) into which it has been integrated. A vector system may comprise a single vector or plasmid, two or more vectors or plasmids, which together contain the total DNA to be introduced into the genome of the host cell, or a transposon. The choice of the vector will typically depend on the compatibility of the vector with the cell into which the vector is to be introduced. The vector may also include a selection marker such as an antibiotic resistance gene that can be used for selection of suitable transformants. Examples of such resistance genes are well known to those of skill in the art.

2. Isolated Polypeptides, Biologically Active Fragments, Polypeptide Variants and Derivatives 2.1 Polypeptides of the Invention The present invention is predicated in part on the determination of the full-length sequence of a sucrose isomerase from *Erwinia rhapontici* (Accession No. WAC2928) and the full-length sequence of a novel sucrose isomerase from a bacterial isolate designated 68J.

The full-length amino acid sequence of the *Erwinia rhapontici* sucrose isomerase extends 632 residues and includes 197 additional residues of carboxyl terminal sequence (set forth in SEQ ID NO: 26) relative to the sequence disclosed by Mattes et al. (supra). The *E. rhapontici* polypeptide includes a leader or signal peptide, set forth in SEQ ID NO: 6, which extends from residues 1 to about 36 of SEQ ID NO: 2. The signal peptide is necessary only for correct localisation of the mature polypeptide in a particular cell compartment (e.g., in the outer membrane, in the inner membrane or in the periplasmic space between the outer membrane and the inner membrane). The mature polypeptide, set forth in SEQ ID NO: 4, extends from about residue 37 to residue 632.

The full-length amino acid sequence of the 68J sucrose isomerase extends 598 residues set forth in SEQ ID NO: 8, and comprises a signal peptide, set forth in SEQ ID NO: 12, extending from residues 1 to about 33 of SEQ ID NO: 8. The mature polypeptide, set forth in SEQ ID NO: 10, extends from about residue 34 to residue 598 of SEQ ID NO: 8. Thus, in one embodiment, the present invention features an isolated precursor polypeptide according to SEQ ID NO: 8, which comprises a leader peptide according to SEQ ID NO: 12 fused in frame with a polypeptide according to SEQ ID NO: 10. In another embodiment, the invention contemplates an isolated mature polypeptide comprising the sequence set forth in SEQ ID NO: 10. Surprisingly, when compared to prior art sucrose isomerases, the 68J sucrose isomerases show remarkable efficiency and product specificity, very rapidly converting sucrose to isomaltulose almost completely, and not significantly catalysing the hydrolysis of isolmaltulose or the formation of trehalulose (see particularly Examples 22–25). In one embodiment, therefore, the 68J sucrose isomerases convert at least about 86%, preferably at least about 87%, more preferably at least about 88%, even more preferably at least about 89% and still even more preferably at least about 91% of sucrose to isomaltulose. In another embodiment, the 68J sucrose isomerases convert sucrose to trehalulose at a rate of less than about 5%, preferably less than about 4%, more preferably less than about 3%, even more preferably less than about 2% and still even more preferably less than about 1% of the yield of isomaltulose produced by the same enzymes. In yet another embodiment, the 68J sucrose isomerases convert sucrose to isomaltulose with a $K_m$ of less than about 50 mM, preferably less than about 49 mM, more preferably less than about 48 mM, even more preferably less than about 47 mM and still even more preferably less than about 46 mM. In still another embodiment, the 68J sucrose isomerases convert sucrose to isomaltulose with a $V_{max}$ of more than about 400, preferably more than about 450, even more preferably more than about 500, even more preferably more than about 550, even more preferably more than about 600, even more preferably more than about 610, even more preferably more than about 620, even more preferably more than about 630, and still even more preferably more than 640 μmoles isomaltulose/mg protein/min.

2.2 Biologically Active and Immuno-Interactive Fragments

Biologically active fragments may be produced according to any suitable procedure known in the art. For example, a suitable method may include first producing a fragment of said polypeptide and then testing the fragment for the appropriate biological activity. In one embodiment, the fragment may be tested for sucrose isomerase activity. Any assay that detects or preferably measures sucrose isomerase activity is contemplated by the present invention. Preferably, sucrose isomerase activity is determined by an aniline/diphenylamine assay and capillary electrophoresis as described herein.

In another embodiment, biological activity of the fragment is tested by introducing a polynucleotide from which a fragment of the polypeptide can be translated into a cell, and detecting sucrose isomerase activity, which is indicative of said fragment being a said biologically active fragment.

The invention also contemplates biologically active fragments of the above polypeptides, including fragments with sucrose isomerase activity and/or with immuno-interactive activity, of at least 6, preferably at least 8, more preferably at least 10, even more preferably at least 12, even more preferably at least 14, even more preferably at least 16, even more preferably at least 18, even more preferably at least 20, even more preferably at least 25, even more preferably at least 30, even more preferably at least 40, even more preferably at least 50, and still even more preferably at least 60, amino acids in length. For example, immuno-interactive fragments contemplated by the present invention are at least 6 and preferably at least 8 amino acids in length, which can elicit an immune response in an animal for the production of antibodies that are immuno-interactive with a sucrose isomerase enzyme of the invention. Exemplary 8-residue immuno-interactive fragments of this type include but are not limited to residues 1–8, 9–16, 17–24, 25–32, 33–40, 41–48, 49–56, 57–64, 73–80, 81–88, 89–96, 97–104, 105–112, 113–120, 121–128, 129–136, 137–144, 145–152, 161–168, 169–176, 177–184, 185–192, 193–200, 201–208, 209–216, 217–224, 225–232, 223–240, 241–248, 249–256, 257–264, 265–272, 273–280, 281–288, 289–296, 297–304, 305–312, 313–320, 321–328, 329–336, 337–344, 345–352, 353–360, 361–368, 369–376, 377–384, 385–392, 393–400, 401–408, 409–416, 417–424, 425–432, 423–440, 441448, 449–456, 457–464, 465–472, 473–480, 481–488, 489–496, 497–504, 505–512, 513–520, 521–528, 529–536, 537–544, 545–552, 553–560, 561–568, 569–576, 577–584, 585–592 and 589–596 of SEQ ID NO: 2, or residues 1–8, 9–1 25–32, 33–40, 41–48, 49–56, 57–64, 65–72, 73–80, 81–88, 89–96, 97–104, 105–112, 113–120, 121–128, 129–136, 137–144, 145–152, 153–160, 161–168, 169–176, 177–184, 185–192, 193–200, 201–208, 209–216, 217–224, 225–232, 223–240, 241–248, 249–256, 257–264, 265–272, 273–280, 281–288, 289–296, 297–304, 305–312, 313–320, 321–328, 329–336, 337–344, 345–352, 353–360, 361–368, 369–376, 377–384, 385–392, 393–400, 401–408, 409–416, 417–424, 425–432, 423–440, 441–448, 449–456, 457–464, 465–472, 473–480, 481–488, 489–496, 497–504, 505–512, 513–520, 521–528, 529–536, 537–544, 545–552, 553–560 and 559–566 of SEQ ID NO: 4.

In a preferred embodiment of this type, the biologically active or immuno-interactive fragment comprises at least one sucrose isomerase consensus sequence selected from SEQ ID NO: 19, 20, 21, 22, 23 or 24.

2.3 Polypeptide Variants

The invention also contemplates polypeptide variants of the polypeptides of the invention wherein said variants have sucrose isomerase activity. Suitable methods of producing polypeptide variants include, for example, producing a modified polypeptide whose sequence is distinguished from a parent polypeptide by substitution, deletion and/or addition of at least one amino acid, wherein the parent polypeptide comprises a sequence set forth in any one of SEQ ID NO: 2, 4, 8 and 10, or a biologically active fragment thereof. The modified polypeptide is then tested for sucrose isomerase activity, wherein the presence of that activity indicates that said modified polypeptide is a said variant.

In another embodiment, a polypeptide variant is produced by introducing into a cell a polynucleotide from which a modified polypeptide can be translated, and detecting sucrose isomerase activity associated with the cell, which is indicative of the modified polypeptide being a said polypeptide variant.

In general, variants will have at least 60%, more suitably at least 70%, preferably at least 80%, and more preferably at least 90% similarity to a polypeptide as for example shown in SEQ ID NO: 2, 4, 8 and 10, or biologically active fragments thereof. It is preferred that variants display at least 60%, more suitably at least 70%, preferably at least 75%, more preferably at least 80%, more preferably at least 85%, more preferably at least 90% and still more preferably at least 95% sequence identity with a polypeptide as for example shown in SEQ ID NO: 2, 4, 8 and 10, or biologically active fragments thereof. In this respect, the window of comparison preferably spans about the full length of the polypeptide or of the biologically active fragment.

Suitable variants can be obtained from any suitable sucrose-metabolising organism. Preferably, the variants are obtained from a sucrose-metabolising bacterium as for example described in Section 3.3 infra.

2.4 Methods of Producing Polypeptide Variants

2.4.1 Mutagenesis

Polypeptide variants according to the invention can be identified either rationally, or via established methods of mutagenesis (see, for example, Watson, J. D. et al., "MOLECULAR BIOLOGY OF THE GENE", Fourth Edition, Benjamin/Cummings, Menlo Park, Calif., 1987). Significantly, a random mutagenesis approach requires no a priori information about the gene sequence that is to be mutated. This approach has the advantage that it assesses the desirability of a particular mutant based on its function, and thus does not require an understanding of how or why the resultant mutant protein has adopted a particular conformation. Indeed, the random mutation of target gene sequences has been one approach used to obtain mutant proteins having desired characteristics (Leatherbarrow, R. 1986, *J. Prot. Eng.* 1: 7–16; Knowles, J. R., 1987, *Science* 236: 1252–1258; Shaw, W. V., 1987, *Biochem. J* 246: 1–17; Gerit, J. A. 1987, *Chem. Rev.* 87: 1079–1105). Alternatively, where a particular sequence alteration is desired, methods of site-directed mutagenesis can be employed. Thus, such methods may be used to selectively alter only those amino acids of the protein that are believed to be important (Craik, C. S., 1985, *Science* 228: 291–297; Cronin, et al., 1988, *Biochem.* 27: 4572–4579; Wilks, et al., 1988, *Science* 242: 1541–1544).

Variant peptides or polypeptides, resulting from rational or established methods of mutagenesis or from combinatorial chemistries as hereinafter described, may comprise conservative amino acid substitutions. Exemplary conservative substitutions in a polypeptide or polypeptide fragment according to the invention may be made according to the following table:

TABLE B

| Original Residue | Exemplary Substitutions |
| --- | --- |
| Ala | Ser |
| Arg | Lys |
| Asn | Gln, His |
| Asp | Glu |
| Cys | Ser |
| Gln | Asn, His, Lys, |
| Glu | Asp, Lys |
| Gly | Pro |
| His | Asn, Gln, |
| Ile | Leu, Val, Met |
| Leu | Ile, Val, Met, Phe |
| Lys | Arg, Gln, Glu |
| Met | Leu, Ile, Phe |
| Phe | Met, Leu, Tyr, Trp |
| Pro | Gly |
| Ser | Ala, Cys, Thr |
| Thr | Ser |
| Trp | Tyr, Phe |
| Tyr | Trp, Phe |
| Val | Ile, Leu |

Substantial changes in function are made by selecting substitutions that are less conservative than those shown in TABLE B. Other replacements would be non-conservative substitutions and relatively fewer of these may be tolerated. Generally, the substitutions which are likely to produce the greatest changes in a polypeptide's properties are those in which (a) a hydrophilic residue (e.g., Ser or Thr) is substituted for, or by, a hydrophobic residue (e.g., Ala, Leu, Ile, Phe or Val); (b) a cysteine or proline is substituted for, or by, any other residue; (c) a residue having an electropositive side chain (e.g., Arg, His or Lys) is substituted for, or by, an electronegative residue (e.g., Glu or Asp) or (d) a residue having a bulky side chain (e.g., Phe or Trp) is substituted for, or by, one having a smaller side chain (e.g., Ala, Ser) or no side chain (e.g., Gly).

What constitutes suitable variants may be determined by conventional techniques. For example, nucleic acids encoding a polypeptide according to SEQ ID NO: 2, 4, 8 and 10 can be mutated using either random mutagenesis for example using transposon mutagenesis, or site-directed mutagenesis as described, for example, in Section 3.3 infra.

2.4.2 Peptide Libraries Produced by Combinatorial Chemistry

A number of facile combinatorial technologies can be utilised to synthesise molecular libraries of immense diversity. In the present case, variants of a polypeptide, or preferably a polypeptide fragment according to the invention, can be synthesised using such technologies. Variants can be screened subsequently using the methods described in Section 2.3.

Preferably, soluble synthetic peptide combinatorial libraries (SPCLs) are produced which offer the advantage of working with free peptides in solution, thus permitting adjustment of peptide concentration to accommodate a particular assay system. SPCLs are suitably prepared as hexamers. In this regard, a majority of binding sites is known to involve four to six residues. Cysteine is preferably excluded from the mixture positions to avoid the formation of disulfides and more difficult-to-define polymers. Exemplary methods of producing SPCLs are disclosed by Houghten et al. (1991, *Nature* 354: 84–86; 1992, *BioTechniques* 13: 412–421), Appel et al. (1992, *Immunomethods* 1: 17–23), and Pinilla et al. (1992, *BioTechniques* 13: 901–905; 1993, *Gene* 128: 71–76).

Preparation of combinatorial synthetic peptide libraries may employ either t-butyloxycarbonyl (t-Boc) or 9-fluorenylmethyloxycarbonyl (Fmoc) chemistries (see Chapter 9.1, of Coligan et al., supra; Stewart and Young, 1984, Solid Phase Peptide Synthesis, 2nd ed. Pierce Chemical Co., Rockford, Ill.; and Atherton and Sheppard, 1989, Solid Phase Peptide Synthesis: A Practical Approach. IRL Press, Oxford) preferably, but not exclusively, using one of two different approaches. The first of these approaches, suitably termed the "split-process-recombine" or "split synthesis" method, was described first by Furka et al. (1988, 14*th Int. Congr. Biochem.*, Prague, Czechoslovakia 5: 47; 1991, *Int. J. Pept. Protein Res.* 37: 487–493) and Lam et al. (1991, *Nature* 354: 82–84), and reviewed later by Eichler et al. (1995, *Medicinal Research Reviews* 15(6): 481-496) and Balkenhohl et al. (1996, *Angew. Chem. Int. Ed. Engl.* 35: 2288–2337). Briefly, the split synthesis method involves dividing a plurality of solid supports such as polymer beads into n equal fractions representative of the number of available amino acids for each step of the synthesis (e.g., 20 L-amino acids), coupling a single respective amino acid to each polymer bead of a corresponding fraction, and then thoroughly mixing the polymer beads of all the fractions together. This process is repeated for a total of x cycles to produce a stochastic collection of up to $N^x$ different compounds. The peptide library so produced may be screened for sucrose isomerase activity. Upon detection, some of the positive beads are selected for sequencing to identify the active peptide. Such a peptide may be subsequently cleaved from the beads, and assayed as above.

The second approach, the chemical ratio method, prepares mixed peptide resins using a specific ratio of amino acids empirically defined to give equimolar incorporation of each amino acid at each coupling step. Each resin bead contains a mixture of peptides. Approximate equimolar representation can be confirmed by amino acid analysis (Dooley and Houghten, 1993, *Proc. Natl. Acad. Sci. U.S.A.* 90: 10811–10815; Eichler and Houghten, 1993, *Biochemistry* 32: 11035–11041). Preferably, the synthetic peptide library is produced on polyethylene rods, or pins, as a solid support, as for example disclosed by Geysen et al. (1986, *Mol. Immunol.* 23: 709–715). An exemplary peptide library of this type may consist of octapeptides in which the third and fourth position represent defined amino acids selected from natural and unnatural amino acids, and in which the remaining six positions represent a randomised mixture of amino acids. This peptide library can be represented by the formula Ac-XXO$_1$O$_2$XXXX-S$_s$, where S$_s$ is the solid support. Peptide mixtures remain on the pins for assaying purposes. For example, a peptide library can be first screened for the ability to convert sucrose to isomaltulose. The most active peptides are then selected for an additional round of testing comprising linking, to the starting peptide, an additional residue (or by internally modifying the components of the original starting peptide) and then screening this set of candidates for sucrose isomerase activity. This process is reiterated until the peptide with the desired sucrose isomerase activity is identified. One identified, the identity of the peptide attached to the solid phase support may be determined by peptide sequencing.

2.4.3 Alanine Scanning Mutagenesis

In one embodiment, the invention herein utilises a systematic analysis of a polypeptide or polypeptide fragment according to the invention to determine the residues in the polypeptide or fragment that are involved in catalysis of sucrose to isomaltulose. Such analysis is conveniently performed using recombinant DNA technology. In general, a DNA sequence encoding the polypeptide or fragment is cloned and manipulated so that it may be expressed in a convenient host. DNA encoding the polypeptide or fragment can be obtained from a genomic library, from cDNA derived from mRNA in cells expressing the said polypeptide or fragment, or by synthetically constructing the DNA sequence (Sambrook et al., supra; Ausubel et al., supra).

The wild-type DNA encoding the polypeptide or fragment is then inserted into an appropriate plasmid or vector as described herein. In particular, prokaryotes are preferred for cloning and expressing DNA sequences to produce variants of the polypeptide or fragment. For example, *E. coli* K12 strain 294 (ATCC No. 31446) may be used, as well as *E. coli* B, *E. coli* X1776 (ATCC No. 31537), and *E. coli* c600 and c600hfl, and *E. coli* W3110 (F⁻, γ⁻, prototrophic, ATCC No. 27325), bacilli such as *Bacillus subtilis*, and other enterobacteriaceae such as *Salmonella typhimurium* or *Serratia marcescens*, and various *Pseudomonas* species. A preferred prokaryote is *E. coli* W3110 (ATCC 27325).

Once the polypeptide or fragment is cloned, site-specific mutagenesis as for example described by Carter et al. (1986, *Nucl. Acids. Res.*, 13: 4331) or by Zoller et al. (1987, *Nucl. Acids Res.*, 10: 6487), cassette mutagenesis as for example described by Wells et al. (1985, *Gene*, 34: 315), restriction selection mutagenesis as for example described by Wells et al. (1986, *Philos. Trans. R. Soc. London SerA*, 317: 415), or other known techniques may be performed on the cloned DNA to produce the variant DNA that codes for the changes in amino acid sequence defined by the residues being substituted. When operably linked to regulatory polynucleotides in an appropriate expression vector, variant polypeptides are obtained. In some cases, recovery of the variant may be facilitated by expressing and secreting such molecules from the expression host by use of an appropriate signal sequence operably linked to the DNA sequence encoding the variant. Such methods are well known to those skilled in the art. Of course, other methods may be employed to produce such polypeptides or fragments such as the in vitro chemical synthesis of the desired polypeptide variant (Barany et al. In *The Peptides*, eds. E. Gross and J. Meienhofer (Academic Press: N.Y. 1979), Vol. 2, pp. 3–254).

Once the different variants are produced, they are contacted with sucrose or a sucrose-containing substrate and the conversion to isomaltulose, if any, is determined for each variant. These sucrose isomerase activities are compared to the activity of the parent polypeptide or fragment to determine which of the amino acid residues in the active site a involved in sucrose isomerisation.

The sucrose isomerase activity of the parent and variant, respectively, can be measured by any convenient assay as for example described herein. While any number of analytical measurements may be used to compare activities, a convenient one for enzymic activity is the Michaelis constant $K_m$ of the variant as compared to the $K_m$ for the parent polypeptide or fragment. Generally, a two-fold increase or decrease in $K_m$ per analogous residue substituted by the substitution indicates that the substituted residue(s) is active in the interaction of the parent polypeptide or fragment with the substrate.

When a suspected or known active amino acid residue is subjected to scanning amino acid analysis, the amino acid residues immediately adjacent thereto should be scanned. The scanning amino acid used in such an analysis may be any different amino acid from that substituted, i.e., any of the 19 other naturally occurring amino acids. Three residue-substituted polypeptides can be made. One contains a scanning amino acid, preferably alanine, at position N that is the suspected or known active amino acid. The two others contain the scanning amino acid at position N+1 and N−1. If each substituted polypeptide or fragment causes a greater than about two-fold effect on $K_m$ for the substrate, the scanning amino acid is substituted at position N+2 and N−2. This is repeated until at least one, and preferably four, residues are identified in each direction which have less than about a two-fold effect on $K_m$ or until either of the ends of the parent polypeptide or fragment are reached. In this manner, along a continuous amino acid sequence one or more amino acids that are involved in the catalysis of sucrose to isomaltulose can be identified.

The active amino acid residue identified by amino acid scan is typically one that contacts sucrose directly. However, active amino acids may also indirectly contact sucrose through salt bridges formed with other residues or small molecules such as $H_2O$ or ionic species such as $Na^+$, $Ca^{+2}$, $Mg^{+2}$, or $Zn^{+2}$.

In some cases, the substitution of a scanning amino acid at one or more residues results in a residue-substituted polypeptide which is not expressed at levels that allow for the isolation of quantities sufficient to carry out analysis of its sucrose isomerase activity. In such cases, a different scanning amino acid, preferably an isosteric amino acid, can be used.

Among the preferred scanning amino acids are relatively small, neutral amino acids. Such amino acids include alanine, glycine, serine, and cysteine. Alanine is the preferred scanning amino acid among this group because it eliminates the side-chain beyond the beta-carbon and is less likely to alter the main-chain conformation of the variant. Alanine is also preferred because it is the most common amino acid. Further, it is frequently found in both buried and exposed positions (Creighton, *The Proteins*, W. H. Freeman & Co., N.Y.; Chothia, 1976, *J. Mol. Biol.*, 150: 1). If alanine substitution does not yield adequate amounts of variant, an isosteric amino acid can be used. Alternatively, the following amino acids in decreasing order of preference may be used: Ser, Asn, and Leu.

Once the active amino acid residues are identified, isosteric amino acids may be substituted. Such isosteric substitutions need not occur in all instances and may be performed before any active amino acid is identified. Such isosteric amino acid substitution is performed to minimise the potential disruptive effects on conformation that some substitutions can cause. Isosteric amino acids are shown in the table below:

TABLE C

| Polypeptide Amino Acid | Isoteric Scanning Amino Acid |
|---|---|
| Ala (A) | Ser, Gly |
| Glu (E) | Gln, Asp |
| Gln (Q) | Asn, Glu |
| Asp (D) | Asn, Glu |
| Asn (N) | Ala, Asp |
| Leu (L) | Met, Ile |
| Gly (G) | Pro, Ala |
| Lys (K) | Met, Arg |
| Ser (S) | Thr, Ala |
| Val (V) | Ile, Thr |
| Arg (R) | Lys, Met, Asn |
| Thr (T) | Ser, Val |
| Pro (P) | Gly |
| Ile (I) | Met, Leu, Val |
| Met (M) | Ile, Leu |
| Phe (F) | Tyr |
| Tyr (Y) | Phe |
| Cys (C) | Ser, Ala |

TABLE C-continued

| Polypeptide Amino Acid | Isoteric Scanning Amino Acid |
|---|---|
| Trp (W) | Phe |
| His (H) | Asn, Gln |

The method herein can be used to detect active amino acid residues within different domains of a polypeptide or fragment according to the invention. Once this identification is made, various modifications to the parent polypeptide or fragment may be made to modify the interaction between the parent polypeptide or fragment and its substrate.

2.4.4 Polypeptide or Peptide Libraries Produced by Phage Display

The identification of variants can also be facilitated through the use of a phage (or phagemid) display protein ligand screening system as for example described by Lowman, et al. (1991, *Biochem.* 30: 10832–10838), Markland, et al. (1991, *Gene* 109: 13–19), Roberts, et al. (1992, *Proc. Natl. Acad. Sci. (U.S.A.)* 89: 2429–2433), Smith, G. P. (1985, *Science* 228: 1315–1317), Smith, et al. (1990, *Science* 248: 1126–1128) and Lardner et al. (U.S. Pat. No. 5,223,409). In general, this method involves expressing a fusion protein in which the desired protein ligand is fused to the N-terminus of a viral coat protein (such as the M13 Gene III coat protein, or a lambda coat protein).

In one embodiment, a library of phage is engineered to display novel peptides within the phage coat protein sequences. Novel peptide sequences are generated by random mutagenesis of gene fragments encoding a polypeptide of the invention or biologically active fragment using error-prone PCR, or by in vivo mutation by *E. coli* mutator cells. The novel peptides displayed on the surface of the phage are placed in contact with sucrose or a sucrose-containing substrate. Phage that display coat protein having peptides that are capable of isomerising sucrose to isomaltulose are then selected. The selected phage can be amplified, and the DNA encoding their coat proteins can be sequenced. In this manner, the amino acid sequence of the embedded peptide or polypeptide can be deduced.

In more detail, the method involves (a) constructing a replicable expression vector comprising a first gene encoding a polypeptide or fragment of the invention, a second gene encoding at least a portion of a natural or wild-type phage coat protein wherein the first and second genes are heterologous, and a transcription regulatory element operably linked to the first and second genes, thereby forming a gene fusion encoding a fusion protein; (b) mutating the vector at one or more selected positions within the first gene thereby forming a family of related plasmids; (c) transforming suitable host cells with the plasmids; (d) infecting the transformed host cells with a helper phage having a gene encoding the phage coat protein; (e) culturing the transformed infected host cells under conditions suitable for forming recombinant phagemid particles containing at least a portion of the plasmid and capable of transforming the host, the conditions adjusted so that no more than a minor amount of phagemid particles displays more than one copy of the fusion protein on the surface of the particle; (f) contacting the phagemid particles with sucrose or a sucrose-containing substrate; and (g) separating the phagemid particles that isomerise sucrose to isomaltulose from those that do not. Preferably, the method further comprises transforming suitable host cells with recombinant phagemid particles that isomerise sucrose to isomaltulose and repeating steps (d) through (g) one or more times.

Preferably, in this method the plasmid is under tight control of the transcription regulatory element, and the culturing conditions are adjusted so that the amount or number of phagemid particles displaying more than one copy of the fusion protein on the surface of the particle is less than about 20%. More, preferably, the number of phagemid particles displaying more than one copy of the fusion protein is less than 10% of the number of phagemid particles displaying a single copy of the fusion protein. Most preferably, the number is less than 1%.

Typically in this method, the expression vector will further contain a secretory signal sequence fused to the DNA encoding each subunit of the polypeptide and the transcription regulatory element will be a promoter system. Preferred promoter systems are selected from lac Z, $\lambda_{PL}$, tac, T7 polymerase, tryptophan, and alkaline phosphatase promoters and combinations thereof. Normally the method will also employ a helper phage selected from M13K07, M13R408, M13-VCS, and Phi X 174. The preferred helper phage is M13K07, and the preferred coat protein is the M13 Phage gene III coat protein. The preferred host is *E. coli*, and protease-deficient strains of *E. coli*.

Repeated cycles of variant selection are used to select for higher and higher affinity binding by the phagemid selection of multiple amino acid changes that are selected by multiple selection cycles. Following a first round of phagemid selection, involving a first region or selection of amino acids in the ligand polypeptide, additional rounds of phagemid selection in other regions or amino acids of the ligand polypeptide are conducted. The cycles of phagemid selection are repeated until the desired affinity properties of the polypeptide are achieved.

It will be appreciated that the amino acid residues that form the active site of the polypeptide or fragment may not be sequentially linked and may reside on different subunits of the polypeptide or fragment. That is, the binding domain tracks with the particular secondary structure at the active site and not the primary structure. Thus, generally, mutations will be introduced into codons encoding amino acids within a particular secondary structure at sites directed away from the interior of the polypeptide so that they will have the potential to interact with sucrose or a sucrose-containing substrate.

The phagemid-display method herein contemplates fusing a polynucleotide encoding the polypeptide or fragment (polynucleotide 1) to a second polynucleotide (polynucleotide 2) such that a fusion protein is generated during transcription. Polynucleotide 2 is typically a coat protein gene of a phage, and preferably it is the phage M13 gene III coat protein, or a fragment thereof. Fusion of polynucleotides 1 and 2 may be accomplished by inserting polynucleotide 2 into a particular site on a plasmid that contains polynucleotide 1, or by inserting polynucleotide 1 into a particular site on a plasmid that contains polynucleotide 2.

Between polynucleotide 1 and polynucleotide 2, DNA encoding a termination codon may be inserted, such termination codons being UAG (amber), UAA (ocher), and UGA (opel) (see for example, Davis et al., *Microbiology* (Harper and Row: New York, 1980), pages 237, 245–247, and 274). The termination codon expressed in a wild-type host cell results in the synthesis of the polynucleotide 1 protein product without the polynucleotide 2 protein attached. However, growth in a suppressor host cell results in the synthesis of detectable quantities of fused protein. Such suppressor host cells contain a tRNA modified to insert an amino acid in the termination codon position of the mRNA, thereby resulting in production of detectable amounts of the fusion protein. Suppressor host cells of this type are well known and described, such as *E. coli* suppressor strain, such as JM101 or XL1-Blue (Bullock et al, 1987, *BioTechniques*, 5: 376–379). Any acceptable method may be used to place such a termination codon into the mRNA encoding the fusion polypeptide.

The suppressible codon may be inserted between the polynucleotide encoding the polypeptide or fragment and a second polynucleotide encoding at least a portion of a phage coat protein. Alternatively, the suppressible termination codon may be inserted adjacent to the fusion site by replacing the last amino acid triplet in the polypeptide/fragment or the first amino acid in the phage coat protein. When the phagemid containing the suppressible codon is grown in a suppressor host cell, it results in the detectable production of a fusion polypeptide containing the polypeptide or fragment and the coat protein. When the phagemid is grown in a non-suppressor host cell, the polypeptide or fragment is synthesised substantially without fusion to the phage coat protein due to termination at the inserted suppressible triplet encoding UAG, UAA, or UGA. In the non-suppressor cell the polypeptide is synthesised and secreted from the host cell due to the absence of the fused phage coat protein which otherwise anchored it to the host cell.

The polypeptide or fragment may be altered at one or more selected codons. An alteration is defined as a substitution, deletion, or insertion of one or more codons in the gene encoding the polypeptide or fragment that results in a change in the amino acid sequence as compared with the unaltered or native sequence of the said polypeptide or fragment. Preferably, the alterations will be by substitution of at least one amino acid with any other amino acid in one or more regions of the molecule. The alterations may be produced by a variety of methods known in the art, as for example described in Section 2.3 and 2.4.1. These methods include, but are not limited to, oligonucleotide-mediated mutagenesis and cassette mutagenesis as described for example herein.

The library of phagemid particles is then contacted with sucrose or a sucrose-containing substrate under suitable conditions. Normally, the conditions, including pH, ionic strength, temperature, and the like will mimic physiological conditions. Phagemid particles having high sucrose isomerase activity are then selected from those having low activity.

Suitable host cells are infected with the selected phagemid particles and helper phage, and the host cells are cultured under conditions suitable for amplification of the phagemid particles. The phagemid particles are then collected and the selection process is repeated one or more times until binders having the desired affinity for the target molecule are selected.

2.4.5 Rational Drug Design

Variants of an isolated polypeptide according to the invention, or a biologically active fragment thereof, may also be obtained using the principles of conventional or of rational drug design as for example described by Andrews, et al. (In: "PROCEEDINGS OF THE ALFRED BENZON SYMPOSIUM", volume 28, pp. 145–165, Munksgaard, Copenhagen, 1990), McPherson, A. (1990, *Eur. J. Biochem.* 189: 1–24), Hol, et al. (In: "MOLECULAR RECOGNITION: CHEMICAL AND BIOCHEMICAL PROBLEMS", Roberts, S. M. (ed.); Royal Society of Chemistry; pp. 84–93, 1989), Hol, W. G. J. (1989, *Arzneim-Forsch.* 39: 1016–1018), Hol, W. G. J. (1986, *Agnew Chem. Int. Ed. Engl.* 25: 767–778).

In accordance with the methods of conventional drug design, the desired variant molecules are obtained by randomly testing molecules whose structures have an attribute in common with the structure of a parent polypeptide or biologically active fragment according to the invention. The quantitative contribution that results from a change in a particular group of a binding molecule can be determined by measuring the capacity of competition or co-operativity between the parent polypeptide or polypeptide fragment and the candidate polypeptide variant.

In one embodiment of rational drug design, the polypeptide variant is designed to share an attribute of the most stable three-dimensional conformation of a polypeptide or polypeptide fragment according to the invention. Thus, the variant may be designed to possess chemical groups that are oriented in a way sufficient to cause ionic, hydrophobic, or van der Waals interactions that are similar to those exhibited by the polypeptide or polypeptide fragment of the invention. In a second method of rational design, the capacity of a particular polypeptide or polypeptide fragment to undergo conformational "breathing" is exploited. Such "breathing"—the transient and reversible assumption of a different molecular conformation—is a well-appreciated phenomenon, and results from temperature, thermodynamic factors, and from the catalytic activity of the molecule. Knowledge of the 3-dimensional structure of the polypeptide or polypeptide fragment facilitates such an evaluation. An evaluation of the natural conformational changes of a polypeptide or polypeptide fragment facilitates the recognition of potential hinge sites, potential sites at which hydrogen bonding, ionic bonds or van der Waals bonds might form or might be eliminated due to the breathing of the molecule, etc. Such recognition permits the identification of the additional conformations that the polypeptide or polypeptide fragment could assume, and enables the rational design and production of mimetic polypeptide variants that share such conformations.

The preferred method for performing rational mimetic design employs a computer system capable of forming a representation of the three-dimensional structure of the polypeptide or polypeptide fragment (such as those obtained using RIBBON (Priestle, J., 1988, *J. Mol. Graphics* 21: 572), QUANTA (Polygen), InSite (Biosyn), or Nanovision (American Chemical Society)). Such analyses are exemplified by Hol, et al. (In: "MOLECULAR RECOGNITION: CHEMICAL AND BIOCHEMICAL PROBLEMS", supra, Hol, W. G. J. (1989, supra) and Hol, W. G. J., (1986, supra).

In lieu of such direct comparative evaluations of candidate polypeptide variants, screening assays may be used to identify such molecules. Such assays will preferably exploit the capacity of the variant to catalyse the conversion of sucrose to isomaltulose.

2.5 Polypeptide Derivatives

With reference to suitable derivatives of the invention, such derivatives include amino acid deletions and/or additions to a polypeptide, fragment or variant of the invention, wherein said derivatives catalyse the conversion of sucrose to isomaltulose. "Additions" of amino acids may include fusion of the polypeptides, fragments and polypeptide variants of the invention with other polypeptides or proteins. For example, it will be appreciated that said polypeptides, fragments or variants may be incorporated into larger polypeptides, and that such larger polypeptides may also be expected to catalyse the conversion of sucrose to isomaltulose as mentioned above.

The polypeptides, fragments or variants of the invention may be fused to a further protein, for example, which is not derived from the original host. The further protein may assist in the purification of the fusion protein. For instance, a polyhistidine tag or a maltose binding protein may be used in this respect as described in more detail below. Other possible fusion proteins are those which produce an immunomodulatory response. Particular examples of such proteins include Protein A or glutathione S-transferase (GST). Other derivatives contemplated by the invention include, but are not limited to, modification to side chains, incorporation of unnatural amino acids and/or their derivatives during peptide, polypeptide or protein synthesis and the use of crosslinkers and other methods which impose conformational constraints on the polypeptides, fragments and variants of the invention.

Examples of side chain modifications contemplated by the present invention include modifications of amino groups such as by acylation with acetic anhydride; acylation of amino groups with succinic anhydride and tetrahydrophthalic anhydride; amidination with methylacetimidate; carbamoylation of amino groups with cyanate; pyridoxylation of lysine with pyridoxal-5-phosphate followed by reduction with $NaBH_4$; reductive alkylation by reaction with an aldehyde followed by reduction with $NaBH_4$; and trinitrobenzylation of amino groups with 2, 4, 6-trinitrobenzene sulphonic acid (TNBS).

The carboxyl group may be modified by carbodiimide activation via O-acylisourea formation followed by subsequent derivatisation, by way of example, to a corresponding amide.

The guanidine group of arginine residues may be modified by formation of heterocyclic condensation products with reagents such as 2,3-butanedione, phenylglyoxal and glyoxal.

Sulphydryl groups may be modified by methods such as performic acid oxidation to cysteic acid; formation of mercurial derivatives using 4-chloromercuriphenylsulphonic acid, 4-chloromercuribenzoate; 2-chloromercuri-4-nitrophenol, phenylmercury chloride, and other mercurials; formation of a mixed disulphides with other thiol compounds; reaction with maleimide, maleic anhydride or other substituted maleimide; carboxymethylation with iodoacetic acid or iodoacetamide; and carbamoylation with cyanate at alkaline pH.

Tryptophan residues may be modified, for example, by alkylation of the indole ring with 2-hydroxy-5-nitrobenzyl bromide or sulphonyl halides or by oxidation with N-bromosuccinimide.

Tyrosine residues may be modified by nitration with tetranitromethane to form a 3-nitrotyrosine derivative.

The imidazole ring of a histidine residue may be modified by N-carbethoxylation with diethylpyrocarbonate or by alkylation with iodoacetic acid derivatives.

Examples of incorporating unnatural amino acids and derivatives during peptide synthesis include but are not limited to, use of 4-amino butyric acid, 6-aminohexanoic acid, 4-amino-3-hydroxy-5-phenylpentanoic acid, 4-amino-3-hydroxy-6-methylheptanoic acid, t-butylglycine, norleucine, norvaline, phenylglycine, ornithine, sarcosine, 2-thienyl alanine and/or D-isomers of amino acids. A list of unnatural amino acids contemplated by the present invention is shown in TABLE D.

TABLE D

| Non-conventional amino acid | Non-conventional amino acid |
| --- | --- |
| α-aminobutyric acid | L-N-methylalanine |
| α-amino-α-methylbutyrate | L-N-methylarginine |
| aminocyclopropane-carboxylate | L-N-methylasparagine |
| aminoisobutyric acid | L-N-methylaspartic acid |
| aminonorbornyl-carboxylate | L-N-methylcysteine |
| cyclohexylalanine | L-N-methylglutamine |
| cyclopentylalanine | L-N-methylglutamic acid |
| L-N-methylisoleucine | L-N-methylhistidine |
| D-alanine | L-N-methylleucine |
| D-arginine | L-N-methyllysine |
| D-aspartic acid | L-N-methylmethionine |
| D-cysteine | L-N-methylnorleucine |
| D-glutamate | L-N-methylnorvaline |
| D-glutamic acid | L-N-methylornithine |
| D-histidine | L-N-methylphenylalanine |
| D-isoleucine | L-N-methylproline |
| D-leucine | L-N-medlylserine |
| D-lysine | L-N-methylthreonine |
| D-methionine | L-N-methyltryptophan |
| D-ornithine | L-N-methyltyrosine |
| D-phenylalanine | L-N-methylvaline |
| D-proline | L-N-methylethylglycine |
| D-serine | L-N-methyl-t-butylglycine |
| D-threonine | L-norleucine |
| D-tryptophan | L-norvaline |
| D-tyrosine | α-methyl-aminoisobutyrate |
| D-valine | α-methyl-γ-aminobutyrate |
| D-α-methylalanine | α-methylcyclohexylalanine |
| D-α-methylarginine | α-methylcylcopentylalanine |
| D-α-methylasparagine | α-methyl-α-napthylalanine |
| D-α-methylaspartate | α-methylpenicillamine |
| D-α-methylcysteine | N-(4-aminobutyl)glycine |
| D-α-methylglutamine | N-(2-aminoethyl)glycine |
| D-α-methylhistidine | N-(3-aminopropyl)glycine |
| D-α-methylisoleucine | N-amino-α-methylbutyrate |
| D-α-methylleucine | α-napthylalanine |
| D-α-methyllysine | N-benzylglycine |
| D-α-methylmethionine | N-(2-carbamylediyl)glycine |
| D-α-methylornithine | N-(carbamylmethyl)glycine |
| D-α-methylphenylalanine | N-(2-carboxyethyl)glycine |
| D-α-methylproline | N-(carboxymethyl)glycine |
| D-α-methylserine | N-cyclobutylglycine |
| D-α-methylthreonine | N-cycloheptylglycine |
| D-α-methyltryptophan | N-cyclohexylglycine |
| D-α-methyltyrosine | N-cyclodecylglycine |
| L-α-methylleucine | L-α-methyllysine |
| L-α-methylmethionine | L-α-methylnorleucine |
| L-α-methylnorvatine | L-α-methylornithine |
| L-α-methylphenylalanine | L-α-methylproline |
| L-α-methylserine | L-α-methylthreonine |
| L-α-methyltryptophan | L-α-methyltyrosine |
| L-α-methylvaline | L-N-methylhomophenylalanine |
| N-(N-(2,2-diphenylethyl carbamylmethyl)glycine 1-carboxy-1-(2,2-diphenyl-ethyl amino)cyclopropane | N-(N-(3,3-diphenylpropyl carbamylmethyl)glycine |

Also contemplated is the use of crosslinkers, for example, to stabilise 3D conformations of the polypeptides, fragments or variants of the invention, using homo-bifunctional crosslinkers such as bifunctional imido esters having $(CH_2)_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety such as maleimido or dithio moiety or carbodiimide. In addition, peptides can be conformationally constrained, for example, by introduction of double bonds between $C_\alpha$ and $C_\beta$ atoms of amino acids, by incorporation of $C_\alpha$ and $N_\alpha$-methylamino acids, and by formation of cyclic peptides or analogues by introducing covalent bonds such as forming an amide bond between the N and C termini between two side chains or between a side chain and the N or C terminus of the peptides or analogues. For example, reference may be made to: Marlowe (1993, *Biorganic & Medicinal Chemistry Letters* 3: 437–44) who describes peptide cyclisation on TFA resin using trimethylsilyl (TMSE) ester as an orthogonal protecting group; Pallin and Tam (1995, *J. Chem. Soc. Chem. Comm.* 2021–2022) who describe the cyclisation of unprotected peptides in aqueous solution by oxime formation; Algin et al (1994, *Tetrahedron Letters* 35: 9633–9636) who disclose solid-phase synthesis of head-to-tail cyclic peptides via lysine side-chain anchoring; Kates et al (1993, *Tetrahedron Letters* 34: 1549–1552) who describe the production of head-to-tail cyclic peptides by three-dimensional solid phase strategy; Tumelty et al (1994, *J. Chem. Soc. Chem. Comm.* 1067–1068) who describe the synthesis of cyclic peptides from an immobilised activated intermediate, wherein activation of the immobilised peptide is carried out with the N-protecting group intact and the N-protecting group is subsequently removed leading to cyclisation; McMurray et al (1994, *Peptide Research* 7: 195–206) who disclose head-to-tail cyclisation of peptides attached to insoluble supports by means of the side chains of aspartic and glutamic acid; Hruby et al (1994, *Reactive Polymers* 22: 231–241) who teach an alternate method for cyclising peptides via solid supports; and Schmidt and Langer (1997, *J. Peptide Res.* 49: 67–73) who disclose a method for synthesising cyclotetrapeptides and cyclopentapeptides. The foregoing methods may be used to produce conformationally constrained polypeptides that catalyse the conversion of sucrose to isomaltulose.

The invention also contemplates polypeptides, fragments or variants of the invention that have been modified using ordinary molecular biological techniques so as to improve their resistance to proteolytic degradation or to optimise solubility properties or to render them more suitable as an immunogenic agent.

2.6 Methods of Preparing the Polypeptides of the Invention

Polypeptides of the invention may be prepared by any suitable procedure known to those of skill in the art. For example, the polypeptides may be prepared by a procedure including the steps of: (a) preparing a recombinant polynucleotide comprising a nucleotide sequence encoding a polypeptide comprising the sequence set forth in any one of SEQ ID NO: 2, 4, 8 and 10, or variant or derivative of these, which nucleotide sequence is operably linked to transcriptional and translational regulatory nucleic acid; (b) introducing the recombinant polynucleotide into a suitable host cell; (c) culturing the host cell to express recombinant polypeptide from said recombinant polynucleotide; and (d) isolating the recombinant polypeptide. Suitably, said nucleotide sequence comprises the sequence set forth in any one of SEQ ID NO: 1, 3, 7 and 9.

The recombinant polynucleotide is preferably in the form of an expression vector that may be a self-replicating extra-chromosomal vector such as a plasmid, or of a vector that integrates into a host genome.

The transcriptional and translational regulatory nucleic acid will generally need to be appropriate for the host cell used for expression. Numerous types of appropriate expression vectors and suitable regulatory sequences are known in the art for a variety of host cells.

Typically, the transcriptional and translational regulatory nucleic acid may include, but is not limited to, promoter sequences, leader or signal sequences, ribosomal binding sites, transcriptional start and stop sequences, translational start and termination sequences, and enhancer or activator sequences.

Constitutive or inducible promoters as known in the art are contemplated by the invention. The promoters may be either naturally occurring promoters, or hybrid promoters that combine elements of more than one promoter.

In a preferred embodiment, the expression vector contains a selectable marker gene to allow the selection of transformed host cells. Selectable marker genes are well known in the art and will vary with the host cell used.

The expression vector may also include a fusion partner (typically provided by the expression vector) so that the recombinant polypeptide of the invention is expressed as a fusion polypeptide with said fusion partner. The main advantage of fusion partners is that they assist identification and/or purification of said fusion polypeptide.

In order to express said fusion polypeptide, it is necessary to ligate a polynucleotide according to the invention into the expression vector so that the translational reading frames of the fusion partner and the polynucleotide coincide.

Well known examples of fusion partners include, but are not limited to, glutathione-S-transferase (GST), Fc potion of human IgG, maltose binding protein (MBP) and hexahistidine ($HIS_6$) (SEQ ID NO: 52), which are particularly useful for isolation of the fusion polypeptide by affinity chromatography. For the purposes of fusion polypeptide purification by affinity chromatography, relevant matrices for affinity chromatography include, but are not restricted to, glutathione-, amylose-, and nickel- or cobalt-conjugated resins. Many such matrices are available in "kit" form, such as the QIAexpress™ system (Qiagen) useful with ($HIS_6$) (SEQ ID NO: 52) fusion partners and the Pharmacia GST purification system. In a preferred embodiment, the recombinant polynucleotide is expressed in the commercial vector pFLAG as described more fully hereinafter.

Another fusion partner well known in the art is green fluorescent protein (GFP). This fusion partner serves as a fluorescent "tag" which allows the fusion polypeptide of the invention to be identified by fluorescence microscopy or by flow cytometry. The GFP tag is useful when assessing subcellular localisation of the fusion polypeptide of the invention, or for isolating cells which express the fusion polypeptide of the invention. Flow cytometric methods such as fluorescence activated cell sorting (FACS) are particularly useful in this latter application.

Preferably, the fusion partners also have protease cleavage sites, such as for Factor $X_a$ or Thrombin, which allow the relevant protease to partially digest the fusion polypeptide of the invention and thereby liberate the recombinant polypeptide of the invention therefrom. The liberated polypeptide can then be isolated from the fusion partner by subsequent chromatographic separation.

Fusion partners according to the invention also include within their scope "epitope tags", which are usually short peptide sequences for which a specific antibody is available. Well known examples of epitope tags for which specific monoclonal antibodies are readily available include c-Myc, influenza virus, haemagglutinin and FLAG tags.

The step of introducing into the host cell the recombinant polynucleotide may be effected by any suitable method including transfection, and transformation, the choice of which will be dependent on the host cell employed. Such methods are well known to those of skill in the art.

Recombinant polypeptides of the invention may be produced by culturing a host cell transformed with an expression vector containing nucleic acid encoding a polypeptide, biologically active fragment, variant or derivative according to the invention. The conditions appropriate for protein expression will vary with the choice of expression vector and the host cell. This is easily ascertained by one skilled in the art through routine experimentation.

Suitable host cells for expression may be prokaryotic or eukaryotic. One preferred host cell for expression of a polypeptide according to the invention is a bacterium. The bacterium used may be *Escherichia coli*. Alternatively, the host cell may be an insect cell such as, for example, SF9 cells that may be utilised with a baculovirus expression system.

The recombinant protein may be conveniently prepared by a person skilled in the art using standard protocols as for example described in Sambrook, et al., MOLECULAR CLONING. A LABORATORY MANUAL (Cold Spring Harbor Press, 1989), in particular Sections 16 and 17; Ausubel et al., CURRENT PROTOCOLS IN MOLECULAR BIOLOGY (John Wiley & Sons, Inc. 1994–1998), in particular Chapters 10 and 16; and Coligan et al., CURRENT PROTOCOLS IN PROTEIN SCIENCE (John Wiley & Sons, Inc. 1995–1997), in particular Chapters 1, 5 and 6.

Alternatively, the polypeptide, fragments, variants or derivatives of the invention may be synthesised using solution synthesis or solid phase synthesis as described, for example, in Chapter 9 of Atherton and Shephard (supra) and in Roberge et al (1995, *Science* 269: 202).

3. Polynucleotides of the Invention 3.1 Method of Isolating Polynucleotides Encoding Isomaltulose-Producing Sucrose Isomerase Enzymes The present invention features a method of isolating novel polynucleotides encoding isomaltulose-producing sucrose isomerase enzymes. The method comprises obtaining an environmental sample from a location in which organisms capable of converting sucrose to isomaltulose have a selective advantage. The environmental sample may comprise, for instance, soil or plant matter including plant surfaces or tissues (e.g., flowers). The environmental sample is preferably obtained from a location that is subject to periodic or constant availability of substantial sucrose concentrations including, but not restricted to, a factory involved in processing or storage sugar-containing plants or plant parts and a field containing remnants of harvested sugar-containing plants. Preferably, but not exclusively, the sugar-containing plant is sugar beet or sugarcane.

The method preferably further comprises selecting or otherwise enriching for dual sucrose- and isomaltulose-metabolising organisms that are capable of using both sucrose and isomaltulose as carbon sources for growth. For example, the organisms may be grown on an isomaltulose-containing medium for a time and under conditions sufficient to select or enrich for isomaltulose-metabolising organisms. Organisms thus selected or enriched may be grown subsequently on a sucrose-containing medium for a time and under conditions sufficient to select or enrich for dual isomaltulose- and sucrose-metabolising organisms. The order in which the organisms are grown on the aforesaid media may be reversed if desired.

Organisms are screened for those that produce isomaltulose from sucrose using at least one assay that quantifies the production of isomaltulose. Preferably, but not exclusively, the assay is an aniline/diphenylamine assay such as, for example, disclosed in Examples 3 and 4 infra. Alternatively, or in addition thereto, an assay is preferably employed which quantifies the conversion of sucrose to isomaltulose. A suitable assay of this type may quantify the isomaltulose product relative to sucrose and/or related metabolites. For example the capillary electrophoresis assay described in Examples 5 and 6 infra may be used in this regard.

Sucrose isomerase-encoding polynucleotides are then isolated from isomaltulose-producing organisms. This isolation preferably comprises screening a nucleic acid library derived from an isomaltulose-producing organism and optionally subclones of this library for polynucleotides encoding isomaltulose-producing sucrose isomerase enzymes. The screening is suitably facilitated using primers or probes that are specific for sucrose isomerase-encoding polynucleotides, as for example disclosed herein. The nucleic acid library is preferably an expression library, which is suitably produced from genomic nucleic acid or cDNA. Desired polynucleotides may be detected using assays that quantify the production of isomaltulose such as, for example, described above. An exemplary protocol for functional screening of polynucleotides is described in Examples 7 to 12.

Clones testing positive for isomaltulose production may then be subjected to nucleic acid sequence analysis to identify genes and/or gene products novel in relation to known sucrose isomerases. Enzymatic activities, yields and purities of desired products may then be compared to known reference enzymes under suitable conditions, to identify isolated polynucleotides that encode polypeptides with superior sucrose isomerase activity.

3.2 Polynucleotides Encoding Polypeptides of the Invention

The invention further provides a polynucleotide that encodes a polypeptide, fragment, variant or derivative as defined above. In one embodiment, the polynucleotide comprises the entire sequence of nucleotides set forth in SEQ ID NO: 1. SEQ ID NO: 1 corresponds to the full-length *E. rhapontici* 1899 bp sucrose isomerase coding sequence. This sequence defines: (1) a first region encoding a signal peptide, from nucleotide 1 through about nucleotide 108; and (2) a second region encoding a mature sucrose isomerase enzyme from about nucleotide 109 through nucleotide 1899. Suitably, the polynucleotide comprises the sequence set forth in SEQ ID NO: 3, which defines the region encoding the mature sucrose isomerase polypeptide without the signal sequence. The coding sequence of the present invention comprises an additional 594 bp of sequence at the 3' end relative to the *E. rhapontici* sucrose isomerase-encoding polynucleotide of Mattes et al. (supra).

In another embodiment, the polynucleotide comprises the entire sequence of nucleotides set forth in SEQ ID NO: 8. SEQ ID NO: 8 corresponds to the 1791-bp full-length sucrose isomerase coding sequence of the bacterial isolate 68J. SEQ ID NO: 12 defines: (1) a first region encoding a signal peptide, from nucleotide 1 through about nucleotide 99; and (2) a second region encoding a mature sucrose isomerase enzyme from about nucleotide 100 through nucleotide 1791. Suitably, the polynucleotide comprises the sequence set forth in SEQ ID NO: 10, which defines the region encoding the mature sucrose isomerase polypeptide without the signal sequence.

3.3 Polynucleotide Variants

In general, polynucleotide variants according to the invention comprise regions that show at least 60%, more suitably at least 70%, preferably at least 80%, and more preferably at least 90% sequence identity over a reference polynucleotide sequence of identical size ("comparison window") or when compared to an aligned sequence in which the alignment is performed by a computer homology program known in the art. What constitutes suitable variants may be determined by conventional techniques. For example, a polynucleotide according to any one of SEQ ID NO: 1, 3, 7 and 9 can be mutated using random mutagenesis (e.g., transposon mutagenesis), oligonucleotide-mediated (or site-directed) mutagenesis, PCR mutagenesis and cassette mutagenesis of an earlier prepared variant or non-variant version of an isolated natural promoter according to the invention.

Oligonucleotide-mediated mutagenesis is a preferred method for preparing nucleotide substitution variants of a polynucleotide of the invention. This technique is well known in the art as, for example, described by Adelman et al. (1983, *DNA* 2:183). Briefly, a polynucleotide according to any one of SEQ ID NO: 1, 3, 7 or 9 is altered by hybridising an oligonucleotide encoding the desired mutation to a template DNA, wherein the template is the single-stranded form of a plasmid or bacteriophage containing the unaltered or parent DNA sequence. After hybridisation, a DNA polymerase is used to synthesise an entire second complementary strand of the template that will thus incorporate the oligonucleotide primer, and will code for the selected alteration in said parent DNA sequence.

Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridise properly to the single-stranded DNA template molecule.

The DNA template can be generated by those vectors that are either derived from bacteriophage M13 vectors, or those vectors that contain a single-stranded phage origin of replication as described by Viera et al. (1987, *Methods Enzymol.* 153:3). Thus, the DNA that is to be mutated may be inserted into one of the vectors to generate single-stranded template. Production of single-stranded template is described, for example, in Sections 4.21–4.41 of Sambrook et al. (1989, supra).

Alternatively, the single-stranded template may be generated by denaturing double-stranded plasmid (or other DNA) using standard techniques.

For alteration of the native DNA sequence, the oligonucleotide is hybridised to the single-stranded template under suitable hybridisation conditions. A DNA polymerising enzyme, usually the Klenow fragment of DNA polymerase I, is then added to synthesise the complementary strand of the template using the oligonucleotide as a primer for synthesis. A heteroduplex molecule is thus formed such that one strand of DNA encodes the mutated form of the polypeptide or fragment under test, and the other strand (the original template) encodes the native unaltered sequence of the polypeptide or fragment under test. This heteroduplex molecule is then transformed into a suitable host cell, usually a prokaryote such as *E. coli*. After the cells are grown, they are plated onto agarose plates and screened using the oligonucleotide primer having a detectable label to identify the bacterial colonies having the mutated DNA. The resultant mutated DNA fragments are then cloned into suitable expression hosts such as *E. coli* using conventional technology and clones that retain the desired sucrose isomerase activity are detected. Where the clones have been derived using random mutagenesis techniques, positive clones would have to be sequenced in order to detect the mutation.

Alternatively, linker-scanning mutagenesis of DNA may be used to introduce clusters of point mutations throughout a sequence of interest that has been cloned into a plasmid vector. For example, reference may be made to Ausubel et al., supra, (in particular, Chapter 8.4) which describes a first protocol that uses complementary oligonucleotides and requires a unique restriction site adjacent to the region that is to be mutagenised. A nested series of deletion mutations is first generated in the region. A pair of complementary oligonucleotides is synthesised to fill in the gap in the sequence of interest between the linker at the deletion endpoint and the nearby restriction site. The linker sequence actually provides the desired clusters of point mutations as it is moved or "scanned" across the region by its position at the varied endpoints of the deletion mutation series. An alternate protocol is also described by Ausubel et al., supra, which makes use of site directed mutagenesis procedures to introduce small clusters of point mutations throughout the target region. Briefly, mutations are introduced into a sequence by annealing a synthetic oligonucleotide containing one or more mismatches to the sequence of interest cloned into a single-stranded M13 vector. This template is grown in an *E. coli* dut⁻ ung⁻ strain, which allows the incorporation of uracil into the template strand. The oligonucleotide is annealed to the purified template and extended with T4 DNA polymerase to create a double-stranded heteroduplex. Finally, the heteroduplex is introduced into a wild-type *E. coli* strain, which will prevent replication of the template strand due to the presence of uracil in template strand, thereby resulting in plaques containing only mutated DNA.

Region-specific mutagenesis and directed mutagenesis using PCR may also be employed to construct polynucleotide variants according to the invention. In this regard, reference may be made, for example, to Ausubel et al., supra, in particular Chapters 8.2A and 8.5.

Alternatively, suitable polynucleotide sequence variants of the invention may be prepared according to the following procedure: (i) creating primers which are optionally degenerate wherein each comprises a portion of a reference polynucleotide encoding a reference polypeptide or fragment of the invention, preferably encoding the sequence set forth in any one of SEQ ID NO: 1, 3, 7 or 9; (ii) obtaining a nucleic acid extract from a sucrose-metabolising organism, which is preferably a bacterium, more preferably from a species obtained from a location in which organisms capable of converting sucrose to isomaltulose could obtain a selective advantage as described herein; and (iii) using said primers to amplify, via nucleic acid amplification techniques, at least one amplification product from said nucleic acid extract, wherein said amplification product corresponds to a polynucleotide variant.

Suitable nucleic acid amplification techniques are well known to the skilled addressee, and include polymerase chain reaction (PCR) as for example described in Ausubel et al. (supra); strand displacement amplification (SDA) as for example described in U.S. Pat. No. 5,422,252; rolling circle replication (RCR) as for example described in Liu et al., (1996, *J. Am. Chem. Soc.* 118:1587–1594 and International application WO 92/01813) and Lizardi et al., (International Application WO 97/19193); nucleic acid sequence-based amplification (NASBA) as for example described by Sooknanan et al., (1994, *Biotechniques* 17:1077–1080); and Q-β replicase amplification as for example described by Tyagi et al., (1996, *Proc. Natl. Acad. Sci. USA* 93: 5395-5400).

Typically, polynucleotide variants that are substantially complementary to a reference polynucleotide are identified by blotting techniques that include a step whereby nucleic acids are immobilised on a matrix (preferably a synthetic membrane such as nitrocellulose), followed by a hybridisation step, and a detection step. Southern blotting is used to identify a complementary DNA sequence; northern blotting is used to identify a complementary RNA sequence. Dot blotting and slot blotting can be used to identify complementary DNA/DNA, DNA/RNA or RNA/RNA polynucleotide sequences. Such techniques are well known by those skilled in the art, and have been described in Ausubel et al. (1994–1998, supra) at pages 2.9.1 through 2.9.20.

According to such methods, Southern blotting involves separating DNA molecules according to size by gel electrophoresis, transferring the size-separated DNA to a synthetic membrane, and hybridising the membrane-bound DNA to a complementary nucleotide sequence labelled radioactively, enzymatically or fluorochromatically. In dot blotting and slot blotting, DNA samples are directly applied to a synthetic membrane prior to hybridisation as above.

An alternative blotting step is used when identifying complementary polynucleotides in a cDNA or genomic DNA library, such as through the process of plaque or colony hybridisation. A typical example of this procedure is described in Sambrook et al. ("Molecular Cloning. A Laboratory Manual", Cold Spring Harbour Press, 1989) Chapters 8–12.

Typically, the following general procedure can be used to determine hybridisation conditions. Polynucleotides are blotted/transferred to a synthetic membrane, as described above. A reference polynucleotide such as a polynucleotide of the invention is labelled as described above, and the ability of this labelled polynucleotide to hybridise with an immobilised polynucleotide is analysed.

A skilled addressee will recognise that a number of factors influence hybridisation. The specific activity of radioactively labelled polynucleotide sequence should typically be greater than or equal to about $10^8$ dpm/mg to provide a detectable signal. A radiolabelled nucleotide sequence of specific activity $10^8$ to $10^9$ dpm/mg can detect approximately 0.5 pg of DNA. It is well known in the art that sufficient DNA must be immobilised on the membrane to permit detection. It is desirable to have excess immobilised DNA, usually 10 μg. Adding an inert polymer such as 10% (w/v) dextran sulfate (MW 500,000) or polyethylene glycol 6000 during hybridisation can also increase the sensitivity of hybridisation (see Ausubel supra at 2.10.10).

To achieve meaningful results from hybridisation between a polynucleotide immobilised on a membrane and a labelled polynucleotide, a sufficient amount of the labelled polynucleotide must be hybridised to the immobilised polynucleotide following washing. Washing ensures that the labelled polynucleotide is hybridised only to the immobilised polynucleotide with a desired degree of complementarity to the labelled polynucleotide.

It will be understood that polynucleotide variants according to the invention will hybridise to a reference polynucleotide under at least low stringency conditions. Reference herein to low stringency conditions includes and encompasses from at least about 1% v/v to at least about 15% v/v formamide and from at least about 1 M to at least about 2 M salt for hybridisation at 42° C., and at least about 0.2 M to about 2 M salt for washing at 42° C. Low stringency conditions also may include 1% Bovine Serum Albumin (BSA), 1 mM EDTA, 0.5 M NaHPO₄ (pH 7.2), 7% SDS for hybridisation at 65° C., and (i) 2×SSC, 0.1% SDS; or (ii) 0.5% BSA, 1 mM EDTA, 40 mM NaHPO₄ (pH 7.2), 5% SDS for washing at room temperature.

Suitably, the polynucleotide variants hybridise to a reference polynucleotide under at least medium stringency conditions. Medium stringency conditions include and encompass from at least about 16% v/v to at least about 30% v/v formamide and from at least about 0.5 M to at least about 0.9 M salt for hybridisation at 42° C., and at least about 0.03 M to about 0.2 M salt for washing at 55° C. Medium stringency conditions also may include 1% Bovine Serum Albumin (BSA), 1 mM EDTA, 0.5 M NaHPO₄ (pH 7.2), 7% SDS for hybridisation at 65° C., and (i) 1×SSC, 0.1% SDS; or (ii) 0.5% BSA, 1 mM EDTA, 40 mM NaHPO₄ (pH 7.2), 5% SDS for washing at 60-65° C.

Preferably, the polynucleotide variants hybridise to a reference polynucleotide under high stringency conditions. High stringency conditions include and encompass from at least about 31% v/v to at least about 50% v/v formamide and from about 0.01 M to about 0.15 M salt for hybridisation at 42° C., and about 0.01 M to about 0.02 M salt for washing at a temperature of at least 55° C. High stringency conditions also may include 1% BSA, 1 mM EDTA, 0.5 M NaHPO₄ (pH 7.2), 7% SDS for hybridisation at 65° C., and (i) 0.2×SSC, 0.1% SDS; or (ii) 0.5% BSA, 1 mM EDTA, 40 mM NaHPO₄ (pH 7.2), 1% SDS for washing at a temperature in excess of 65° C.

Other stringent conditions are well known in the art. A skilled addressee will recognise that various factors can be manipulated to optimise the specificity of the hybridisation. Optimisation of the stringency of the final washes can serve to ensure a high degree of hybridisation. For detailed examples, see Ausubel et al., supra at pages 2.10.1 to 2.10.16 and Sambrook et al. (1989, supra) at sections 1.101 to 1.104.

While stringent washes are typically carried out at temperatures from about 42° C. to 68° C., one skilled in the art will appreciate that other temperatures may be suitable for stringent conditions. Maximum hybridisation rate typically occurs at about 20° C. to 25° C. below the $T_m$ for formation of a DNA-DNA hybrid. It is well known in the art that the $T_m$ is the melting temperature, or temperature at which two complementary polynucleotide sequences dissociate. Methods for estimating $T_m$ are well known in the art (see Ausubel et al., supra at page 2.10.8).

In general, the $T_m$ of a perfectly matched duplex of DNA may be predicted as an approximation by the formula:

$$T_m = 81.5 + 16.6 \,(\log_{10} M) + 0.41 \,(\%G+C) - 0.63 \,(\% \text{formamide}) - (600/\text{length})$$

wherein: M is the concentration of Na⁺, preferably in the range of 0.01 molar to 0.4 molar; % G+C is the sum of guanosine and cytosine bases as a percentage of the total number of bases, within the range between 30% and 75% G+C; % formamide is the percent formamide concentration by volume; length is the number of base pairs in the DNA duplex.

The $T_m$ of a duplex DNA decreases by approximately 1° C. to 1.5° C. with every increase of 1% in the number of randomly mismatched base pairs. Washing is generally carried out at $T_m-5$ to 15° C. for high stringency, or $T_m-16$ to 30° C. for moderate stringency.

In a preferred hybridisation procedure, a membrane (e.g., a nitrocellulose membrane or a nylon membrane) containing immobilised DNA is hybridised overnight at 42° C. in a hybridisation buffer (50% deionised formamide, 5×SSC, 5× Denhardt's solution (0.1% ficoll, 0.1% polyvinylpyrollidone and 0.1% bovine serum albumin), 0.1% SDS and 200 mg/mL denatured salmon sperm DNA) containing labelled probe. The membrane is then subjected to two sequential low to medium stringency washes (i.e., 2×SSC, 0.1% SDS for 15 min at 45° C., followed by 2×SSC, 0.1% SDS for 15 min at 50° C.), followed by two sequential higher stringency washes (i.e., 0.2×SSC, 0.1% SDS for 12 min at 55° C. followed by 0.2×SSC and 0.1%SDS solution for 12 min at 65–68° C.).

Methods for detecting a labelled polynucleotide hybridised to an immobilised polynucleotide are well known to practitioners in the art. Such methods include autoradiography, phosphorimaging, and chemiluminescent, fluorescent and colorimetric detection.

4. Antigen-Binding Molecules

The invention also contemplates antigen-binding molecules that bind specifically to the aforementioned polypeptides, fragments, variants and derivatives. Preferably, an antigen-binding molecule according to the invention is immuno-interactive with any one or more of the amino acid sequences set forth in SEQ ID NO: 2, 4, 8, 10, 19, 20, 21, 22, 23 and 24 or variants thereof.

For example, the antigen-binding molecules may comprise whole polyclonal antibodies. Such antibodies may be prepared, for example, by injecting a polypeptide, fragment, variant or derivative of the invention into a production species, which may include mice or rabbits, to obtain polyclonal antisera. Methods of producing polyclonal antibodies are well known to those skilled in the art. Exemplary protocols which may be used are described for example in Coligan et al., CURRENT PROTOCOLS IN IMMUNOLOGY, (John Wiley & Sons, Inc, 1991), and Ausubel et al., (1994–1998, supra), in particular Section III of Chapter 11.

In lieu of the polyclonal antisera obtained in the production species, monoclonal antibodies may be produced using the standard method as described, for example, by Köhler and Milstein (1975, *Nature* 256, 495–497), or by more recent modifications thereof as described, for example, in Coligan et al., (1991, supra) by immortalising spleen or other antibody producing cells derived from a production species which has been inoculated with one or more of the polypeptides, fragments, variants or derivatives of the invention.

The invention also contemplates as antigen-binding molecules Fv, Fab, Fab' and F(ab')$_2$ immunoglobulin fragments.

Alternatively, the antigen-binding molecule may comprise a synthetic stabilised Fv fragment. Exemplary fragments of this type include single chain Fv fragments (sFv, frequently termed scFv) in which a peptide linker is used to bridge the N terminus or C terminus of a $V_H$ domain with the C terminus or N-terminus, respectively, of a $V_L$ domain. ScFv lack all constant parts of whole antibodies and are not able to activate complement. Suitable peptide linkers for joining the $V_H$ and $V_L$ domains are those which allow the $V_H$ and $V_L$ domains to fold into a single polypeptide chain having an antigen binding site with a three dimensional structure similar to that of the antigen binding site of a whole antibody from which the Fv fragment is derived. Linkers having the desired properties may be obtained by the method disclosed in U.S. Pat. No. 4,946,778. However, in some cases a linker is absent. ScFvs may be prepared, for example, in accordance with methods outlined in Kreber et al (Kreber et al. 1997, *J. Immunol. Methods;* 201(1): 35–55). Alternatively, they may be prepared by methods described in U.S. Pat. No. 5,091,513, European Patent No 239,400 or the articles by Winter and Milstein (1991, Nature 349:293) and Plückthun et al (1996, *In Antibody engineering: A practical approach.* 203–252).

Alternatively, the synthetic stabilised Fv fragment comprises a disulphide stabilised Fv (dsFv) in which cysteine residues are introduced into the $V_H$ and $V_L$ domains such that in the fully folded Fv molecule the two residues will form a disulphide bond therebetween. Suitable methods of producing dsFv are described for example in (Glockscuther et al. *Biochem.* 29: 1363–1367; Reiter et al. 1994, *J. Biol. Chem.* 269: 18327–18331; Reiter et al. 1994, *Biochem.* 33: 5451–5459; Reiter et al. 1994. *Cancer Res.* 54: 2714–2718; Webber et al. 1995, *Mol. Immunol.* 32: 249–258).

Also contemplated as antigen-binding molecules are single variable region domains (termed dAbs) as for example disclosed in Ward et al. (1989, *Nature* 341: 544–546); Hamers-Casterman et al. (1993, *Nature.* 363: 446–448); Davies & Riechmann, (1994, *FEBS Lett.* 339: 285–290).

Alternatively, the antigen-binding molecule may comprise a "minibody". In this regard, minibodies are small versions of whole antibodies, which encode in a single chain the essential elements of a whole antibody. Suitably, the minibody is comprised of the $V_H$ and $V_L$ domains of a native antibody fused to the hinge region and CH3 domain of the immunoglobulin molecule as, for example, disclosed in U.S. Pat. No. 5,837,821.

In an alternate embodiment, the antigen binding molecule may comprise non-immunoglobulin derived, protein frameworks. For example, reference may be made to Ku & Schultz, (1995, *Proc. Natl. Acad. Sci. USA,* 92: 652–6556) which discloses a four-helix bundle protein cytochrome b562 having two loops randomised to create complementarity determining regions (CDRs), which have been selected for antigen binding.

The antigen-binding molecule may be multivalent (i.e., having more than one antigen binding site). Such multivalent molecules may be specific for one or more antigens. Multivalent molecules of this type may be prepared by dimerisation of two antibody fragments through a cysteinyl-containing peptide as, for example disclosed by Adams et al., (1993, *Cancer Res.* 53: 4026–4034) and Cumber et al. (1992, *J. Immunol.* 149: 120–126). Alternatively, dimerisation may be facilitated by fusion of the antibody fragments to amphiphilic helices that naturally dimerise (Pack P. Plünckthun, 1992, *Biochem.* 31: 1579–1584), or by use of domains (such as the leucine zippers jun and fos) that preferentially heterodimerise (Kostelny et al., 1992, *J. Immunol.* 148: 1547–1553). In an alternate embodiment, the multivalent molecule may comprise a multivalent single chain antibody (multi-scFv) comprising at least two scFvs linked together by a peptide linker. In this regard, non-covalently or covalently linked scFv dimers termed "diabodies" may be used. Multi-scFvs may be bispecific or greater depending on the number of scFvs employed having different antigen binding specificities. Multi-scFvs may be prepared for example by methods disclosed in U.S. Pat. No. 5,892,020.

The antigen-binding molecules of the invention may be used for affinity chromatography in isolating a natural or recombinant polypeptide or biologically active fragment of the invention. For example reference may be made to immunoaffinity chromatographic procedures described in Chapter 9.5 of Coligan et al., (1995–1997, supra).

The antigen-binding molecules can be used to screen expression libraries for variant polypeptides of the invention as described herein. They can also be used to detect and/or isolate the polypeptides, fragments, variants and derivatives of the invention. Thus, the invention also contemplates the use of antigen-binding molecules to isolate sucrose isomerase enzymes using, for example, any suitable immunoaffinity based method including, but not limited to, immunochromatography and immunoprecipitation. A preferred method utilises solid phase adsorption in which anti-sucrose isomerase antigen-binding molecules are attached to a suitable resin, the resin is contacted with a sample suspected of containing sucrose isomerases, and the sucrose isomerases, if any, are subsequently eluted from the resin. Preferred resins include: Sepharose® (Pharmacia), Poros® resins (Roche Molecular Biochemicals, Indianapolis), Actigel Superflow™ resins (Sterogene Bioseparations Inc., Carlsbad Calif.), and Dynabeads™ (Dynal Inc., Lake Success, N.Y.).

5. Methods of Detection 5.1 Detection of Polypeptides According to the Invention The invention also extends to a method of detecting in a sample a polypeptide, fragment, variant or derivative as broadly described above, comprising contacting the sample with an antigen-binding molecule as described in Section 4 and detecting the presence of a complex comprising the said antigen-binding molecule and the said polypeptide, fragment, variant or derivative in said contacted sample.

Any suitable technique for determining formation of the complex may be used. For example, an antigen-binding molecule according to the invention, having a reporter molecule associated therewith may be utilised in immunoassays. Such immunoassays include, but are not limited to, radioimmunoassays (RIAs), enzyme-linked immunosorbent assays (ELISAs) and immunochromatographic techniques (ICTs), Western blotting which are well known those of skill in the art. For example, reference may be made to "CURRENT PROTOCOLS IN IMMUNOLOGY" (1994, supra) which discloses a variety of immunoassays that may be used in accordance with the present invention. Immunoassays may include competitive assays as understood in the art or as for example described infra. It will be understood that the present invention encompasses qualitative and quantitative immunoassays.

Suitable immunoassay techniques are described for example in U.S. Pat. Nos. 4,016,043, 4,424,279 and 4,018,653. These include both single-site and two-site assays of the non-competitive types, as well as the traditional competitive binding assays. These assays also include direct binding of a labelled antigen-binding molecule to a target antigen.

Two site assays are particularly favoured for use in the present invention. A number of variations of these assays exist, all of which are intended to be encompassed by the present invention. Briefly, in a typical forward assay, an unlabelled antigen-binding molecule such as an unlabelled antibody is immobilised on a solid substrate and the sample to be tested brought into contact with the bound molecule. After a suitable period of incubation, for a period of time sufficient to allow formation of an antibody-antigen complex, another antigen-binding molecule, suitably a second antibody specific to the antigen, labelled with a reporter molecule capable of producing a detectable signal is then added and incubated, allowing time sufficient for the formation of another complex of antibody-antigen-labelled antibody. Any unreacted material is washed away and the presence of the antigen is determined by observation of a signal produced by the reporter molecule. The results may be either qualitative, by simple observation of the visible signal, or may be quantitated by comparing with a control sample containing known amounts of antigen. Variations on the forward assay include a simultaneous assay, in which both sample and labelled antibody are added simultaneously to the bound antibody. These techniques are well known to those skilled in the art, including minor variations as will be readily apparent. In accordance with the present invention, the sample is one that might contain a sucrose isomerase such as from a sucrose-metabolising organism. Preferably, the sucrose-metabolising organism is a bacterium, which is suitably obtained from a location in which organisms that are capable of converting sucrose to isomaltulose have a selective advantage.

In the typical forward assay, a first antibody having specificity for the antigen or antigenic parts thereof is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, discs of microplates, or any other surface suitable for conducting an immunoassay. The binding processes are well known in the art and generally consist of cross-linking, covalently binding or physically adsorbing. The polymer-antibody complex is washed in preparation for the test sample. An aliquot of the sample to be tested is then added to the solid phase complex and incubated for a period of time sufficient and under suitable conditions to allow binding of any antigen present to the antibody. Following the incubation period, the antigen-antibody complex is washed and dried and incubated with a second antibody specific for a portion of the antigen. The second antibody has generally a reporter molecule associated therewith that is used to indicate the binding of the second antibody to the antigen. The amount of labelled antibody that binds, as determined by the associated reporter molecule, is proportional to the amount of antigen bound to the immobilised first antibody.

An alternative method involves immobilising the antigen in the biological sample and then exposing the immobilised antigen to specific antibody that may or may not be labelled with a reporter molecule. Depending on the amount of target and the strength of the reporter molecule signal, a bound antigen may be detectable by direct labelling with the antibody. Alternatively, a second labelled antibody, specific to the first antibody is exposed to the target-first antibody complex to form a target-first antibody-second antibody tertiary complex. The complex is detected by the signal emitted by the reporter molecule.

From the foregoing, it will be appreciated that the reporter molecule associated with the antigen-binding molecule may include the following:

(a) direct attachment of the reporter molecule to the antigen-binding molecule;

(b) indirect attachment of the reporter molecule to the antigen-binding molecule; i.e., attachment of the reporter molecule to another assay reagent which subsequently binds to the antigen-binding molecule; and (c) attachment to a subsequent reaction product of the antigen-binding molecule.

The reporter molecule may be selected from a group including a chromogen, a catalyst, an enzyme, a fluorochrome, a chemiluminescent molecule, a lanthanide ion such as Europium ($Eu^{34}$), a radioisotope and a direct visual label.

In the case of a direct visual label, use may be made of a colloidal metallic or non-metallic particle, a dye particle, an enzyme or a substrate, an organic polymer, a latex particle, a liposome, or other vesicle containing a signal producing substance and the like.

A large number of enzymes suitable for use as reporter molecules is disclosed in United States Patent Specifications U.S. Pat. No. 4,366,241, U.S. Pat. No. 4,843,000, and U.S. Pat. No. 4,849,338. Suitable enzymes useful in the present invention include alkaline phosphatase, horseradish peroxidase, luciferase, β-galactosidase, glucose oxidase, lysozyme, malate dehydrogenase and the like. The enzymes may be used alone or in combination with a second enzyme that is in solution.

Suitable fluorochromes include, but are not limited to, fluorescein isothiocyanate (FITC), tetramethylrhodamine isothiocyanate (TRITC), R-Phycoerythrin (RPE), and Texas Red. Other exemplary fluorochromes include those discussed by Dower et al. (International Publication WO 93/06121). Reference also may be made to the fluorochromes described in U.S. Pat. Nos. 5,573,909 (Singer et al), 5,326,692 (Brinkley et al). Alternatively, reference may be made to the fluorochromes described in U.S. Pat. Nos. 5,227,487, 5,274,113, 5,405,975, 5,433,896, 5,442,045, 5,451,663, 5,453,517, 5,459,276, 5,516,864, 5,648,270 and 5,723,218.

In the case of an enzyme immunoassay, an enzyme is conjugated to the second antibody, generally by means of glutaraldehyde or periodate. As will be readily recognised, however, a wide variety of different conjugation techniques exist which are readily available to the skilled artisan. The substrates to be used with the specific enzymes are generally chosen for the production of, upon hydrolysis by the corresponding enzyme, a detectable colour change. Examples of suitable enzymes include those described supra. It is also possible to employ fluorogenic substrates, which yield a fluorescent product rather than the chromogenic substrates noted above. In all cases, the enzyme-labelled antibody is added to the first antibody-antigen complex. It is then allowed to bind, and excess reagent is washed away. A solution containing the appropriate substrate is then added to the complex of antibody-antigen-antibody. The substrate will react with the enzyme linked to the second antibody, giving a qualitative visual signal, which may be further quantitated, usually spectrophotometrically, to give an indication of the amount of antigen which was present in the sample.

Fluorescent compounds, such as fluorescein, rhodamine and the lanthanide, europium (EU), may be alternately chemically coupled to antibodies without altering their binding capacity. When activated by illumination with light of a particular wavelength, the fluorochrome-labelled antibody adsorbs the light energy, inducing a state to excitability in the molecule, followed by emission of the light at a characteristic colour visually detectable with a light microscope. The fluorescent-labelled antibody is allowed to bind to the first antibody-antigen complex. After washing off the unbound reagent, the remaining tertiary complex is then exposed to light of an appropriate wavelength. The fluorescence observed indicates the presence of the antigen of interest. Immunofluorometric assays (IFMA) are well established in the art. However, other reporter molecules, such as radioisotope, chemiluminescent or bioluminescent molecules may also be employed.

5.2 Detection of Polynucleotides According to the Invention

In another embodiment, the method for detection comprises detecting expression in a cell of a polynucleotide encoding said polypeptide, fragment, variant or derivative. Expression of the said polynucleotide may be determined using any suitable technique. For example, a labelled polynucleotide encoding a said member may be utilised as a probe in a Northern blot of a RNA extract obtained from the muscle cell. Preferably, a nucleic acid extract from the animal is utilised in concert with oligonucleotide primers corresponding to sense and antisense sequences of a polynucleotide encoding a said member, or flanking sequences thereof, in a nucleic acid amplification reaction such as RT PCR. A variety of automated solid-phase detection techniques is also appropriate. For example, very large scale immobilised primer arrays (VLSIPS™) are used for the detection of nucleic acids as for example described by Fodor et al. (1991, *Science* 251:767–777) and Kazal et al. (1996, *Nature Medicine* 2:753–759). The above generic techniques are well known to persons skilled in the art.

6. Chimeric Nucleic Acid Constructs 6.1 Prokaryotic Expression

The present invention further relates to a chimeric nucleic acid construct designed for genetic transformation of prokaryotic cells, comprising a polynucleotide, fragment or variant according to the invention operably linked to a promoter sequence. Preferably, the chimeric construct is operable in a Gram-negative prokaryotic cell. A variety of prokaryotic expression vectors, which may be used as a basis for constructing the chimeric nucleic acid construct, may be utilised to express a polynucleotide, fragment or variant according to the invention. These include but are not limited to a chromosomal vector (e.g., a bacteriophage such as bacteriophage λ), an extrachromosomal vector (e.g., a plasmid or a cosmid expression vector). The expression vector will also typically contain an origin of replication, which allows autonomous replication of the vector, and one or more genes that allow phenotypic selection of the transformed cells. Any of a number of suitable promoter sequences, including constitutive and inducible promoter sequences, may be used in the expression vector (see e.g., Bitter, et al., 1987, *Methods in Enzymology* 153: 516–544). For example, inducible promoters such as pL of bacteriophage γ, plac, ptrp, ptac ptrp-lac hybrid promoter and the like may be used. The chimeric nucleic acid construct may then be used to transform the desired prokaryotic host cell to produce a recombinant prokaryotic host cell for producing a recombinant polypeptide as described above or for producing isomaltulose as described hereinafter.

6.2 Eukaryotic Expression

The invention also contemplates a chimeric nucleic acid construct designed for expressing a polynucleotide, fragment or variant of the invention in a eukaryotic host cell. A variety of eukaryotic host-expression vector systems may be utilised in this regard. These include, but are not limited to, yeast transformed with recombinant yeast expression vectors; insect cell systems infected with recombinant virus expression vectors (e.g., baculovirus); or animal cell systems infected with recombinant virus expression vectors (e.g., retroviruses, adenovirus, Vaccinia virus), or transformed animal cell systems engineered for stable expression. Preferably, the chimeric nucleic acid construct is designed for genetic transformation of plants as described hereinafter.

6.3 Plant Expression

In a preferred embodiment, a polynucleotide, fragment or variant according to the invention is fused to a promoter sequence and a 3' non-translated sequence to create a chimeric DNA construct, designed for genetic transformation of plants.

6.3.1 Plant Promoters

Promoter sequences contemplated by the present invention may be native to the host plant to be transformed or may be derived from an alternative source, where the region is functional in the host plant. Other sources include the *Agrobacterium* T-DNA genes, such as the promoters for the biosynthesis of nopaline, octapine, mannopine, or other opine promoters; promoters from plants, such as the ubiquitin promoter; tissue specific promoters (see, e.g., U.S. Pat. No. 5,459,252 to Conkling et al.; WO 91/13992 to Advanced Technologies); promoters from viruses (including host specific viruses), or partially or wholly synthetic promoters. Numerous promoters that are functional in mono- and dicotyledonous plants are well known in the art (see, for example, Greve, 1983, *J. Mol. Appl. Genet.* 1: 499–511; Salomon et al., 1984, *EMBO J.* 3: 141–146; Garfinkel et al., 1983, *Cell* 27: 143–153; Barker et al., 1983, *Plant Mol. Biol.* 2: 235–350); including various promoters isolated from plants (such as the Ubi promoter from the maize ubi-1 gene, Christensen and Quail, 1996) (see, e.g., U.S. Pat. No. 4,962,028) and viruses (such as the cauliflower mosaic virus promoter, CaMV 35S).

The promoters sequences may include regions which regulate transcription, where the regulation involves, for example, chemical or physical repression or induction (e.g., regulation based on metabolites, light, or other physico-chemical factors; see, e.g., WO 93/06710 disclosing a nematode responsive promoter) or regulation based on cell differentiation (such as associated with leaves, roots, seed, or the like in plants; see, e.g., U.S. Pat. No. 5,459,252 disclosing a root-specific promoter). Thus, the promoter region, or the regulatory portion of such region, is obtained from an appropriate gene that is so regulated. For example, the 1,5-ribulose biphosphate carboxylase gene is light-induced and may be used for transcriptional initiation. Other genes are known which are induced by stress, temperature, wounding, pathogen effects, etc.

The preferred promoter for expression in cultured cells is a strong constitutive promoter, or a promoter that responds to a specific inducer (Gatz and Lenk, 1998, *Trends Plant Science* 3: 352–8). The preferred promoter for expression in intact plants is a promoter expressed in sucrose storage tissues (such as the mature stems of sugarcane and the tubers of sugar beet), or an inducible promoter to drive conversion of sucrose to isomaltulose at a late stage before harvest with minimal disruption to other plant growth and development processes.

6.3.2 3' Non-Translated Region

The chimeric gene construct of the present invention can comprise a 3' non-translated sequence. A 3' non-translated sequence refers to that portion of a gene comprising a DNA segment that contains a polyadenylation signal and any other regulatory signals capable of effecting mRNA processing or gene expression. The polyadenylation signal is characterised by effecting the addition of polyadenylic acid tracts to the 3' end of the mRNA precursor. Polyadenylation signals are commonly recognised by identity with the canonical form 5' AATAAA-3' although variations are not uncommon.

The 3' non-translated regulatory DNA sequence preferably includes from about 50 to 1,000 nucleotide base pairs and may contain plant transcriptional and translational termination sequences in addition to a polyadenylation signal and any other regulatory signals capable of effecting mRNA processing or gene expression. Examples of suitable 3' non-translated sequences are the 3' transcribed non-translated regions containing a polyadenylation signal from the nopaline synthase (nos) gene of *Agrobacterium tumefaciens* (Bevan et al., 1983, *Nucl. Acid Res.,* 11:369) and the terminator for the T7 transcript from the octopine synthase gene of *Agrobacterium tumefaciens*. Alternatively, suitable 3' non-translated sequences may be derived from plant genes such as the 3' end of the protease inhibitor I or II genes from potato or tomato, the soybean storage protein genes and the pea E9 small subunit of the ribulose-1,5-bisphosphate carboxylase (ssRUBISCO) gene, although other 3' elements known to those of skill in the art can also be employed. Alternatively, 3' non-translated regulatory sequences can be obtained de novo as, for example, described by An (1987, *Methods in Enzymology,* 153:292), which is incorporated herein by reference.

6.3.3 Optional Sequences

The chimeric DNA construct of the present invention can further include enhancers, either translation or transcription enhancers, as may be required. These enhancer regions are well known to persons skilled in the art, and can include the ATG initiation codon and adjacent sequences. The initiation codon must be in phase with the reading frame of the coding sequence relating to the foreign or endogenous DNA sequence to ensure translation of the entire sequence. The translation control signals and initiation codons can be of a variety of origins, both natural and synthetic. Translational initiation regions may be provided from the source of the transcriptional initiation region, or from the foreign or endogenous DNA sequence. The sequence can also be derived from the source of the promoter selected to drive transcription, and can be specifically modified so as to increase translation of the mRNA.

Examples of transcriptional enhancers include, but are not restricted to, elements from the CaMV 35S promoter and octopine synthase genes as for example described by Last et al. (U.S. Pat. No. 5,290,924, which is incorporated herein by reference). It is proposed that the use of an enhancer element such as the ocs element, and particularly multiple copies of the element, will act to increase the level of transcription from adjacent promoters when applied in the context of plant transformation. Alternatively, the omega sequence derived from the coat protein gene of the tobacco mosaic virus (Gallie et al., 1987) may be used to enhance translation of the mRNA transcribed from a polynucleotide according to the invention.

As the DNA sequence inserted between the transcription initiation site and the start of the coding sequence, i.e., the untranslated leader sequence, can influence gene expression, one can also employ a particular leader sequence. Preferred leader sequences include those that comprise sequences selected to direct optimum expression of the foreign or endogenous DNA sequence. For example, such leader sequences include a preferred consensus sequence which can increase or maintain mRNA stability and prevent inappropriate initiation of translation as for example described by Joshi (1987, *Nucl. Acid Res.,* 15:6643), which is incorporated herein by reference. However, other leader sequences, e.g., the leader sequence of RTBV, have a high degree of secondary structure that is expected to decrease mRNA stability and/or decrease translation of the mRNA. Thus, leader sequences (i) that do not have a high degree of secondary structure, (ii) that have a high degree of secondary structure where the secondary structure does not inhibit mRNA stability and/or decrease translation, or (iii) that are derived from genes that are highly expressed in plants, will be most preferred.

Regulatory elements such as the sucrose synthase intron as, for example, described by Vasil et al. (1989, *Plant Physiol.,* 91:5175), the Adh intron I as, for example, described by Callis et al (1987, *Genes Develop.,* II), or the TMV omega element as, for example, described by Gallie et al (1989, *The Plant Cell,* 1:301) can also be included where desired. Other such regulatory elements useful in the practice of the invention are known to those of skill in the art.

Additionally, targeting sequences may be employed to target a protein product of the foreign or endogenous DNA sequence to an intracellular compartment within plant cells or to the extracellular environment. For example, a DNA sequence encoding a transit or signal peptide sequence may be operably linked to a sequence encoding a desired protein such that, when translated, the transit or signal peptide can transport the protein to a particular intracellular or extracellular destination, and can then be post-translationally removed. Transit or signal peptides act by facilitating the transport of proteins through intracellular membranes, e.g., endoplasmic reticulum, vacuole, vesicle, plastid, mitochondrial and plasmalemma membranes. For example, the targeting sequence can direct a desired protein to a particular organelle such as a vacuole or a plastid (e.g., a chloroplast), rather than to the cytosol. Thus, the chimeric DNA construct can further comprise a plastid transit peptide encoding DNA sequence operably linked between a promoter region or promoter variant according to the invention and the foreign or endogenous DNA sequence. For example, reference may be made to Heijne et al. (1989, *Eur. J. Biochem.*, 180:535) and Keegstra et al. (1989, *Ann. Rev. Plant Physiol. Plant Mol. Biol.*, 40:471), which are incorporated herein by reference.

A chimeric DNA construct can also be introduced into a vector, such as a plasmid. Plasmid vectors include additional DNA sequences that provide for easy selection, amplification, and transformation of the expression cassette in prokaryotic and eukaryotic cells, e.g., pUC-derived vectors, pSK-derived vectors, pGEM-derived vectors, pSP-derived vectors, or pBS-derived vectors. Additional DNA sequences include origins of replication to provide for autonomous replication of the vector, selectable marker genes, preferably encoding antibiotic or herbicide resistance, unique multiple cloning sites providing for multiple sites to insert DNA sequences or genes encoded in the chimeric DNA construct, and sequences that enhance transformation of prokaryotic and eukaryotic cells.

The vector preferably contains an element(s) that permits either stable integration of the vector into the host cell genome or autonomous replication of the vector in the cell independent of the genome of the cell. The vector may be integrated into the host cell genome when introduced into a host cell. For integration, the vector may rely on a foreign or endogenous DNA sequence present therein or any other element of the vector for stable integration of the vector into the genome by homologous recombination. Alternatively, the vector may contain additional nucleic acid sequences for directing integration by homologous recombination into the genome of the host cell. The additional nucleic acid sequences enable the vector to be integrated into the host cell genome at a precise location in the chromosome. To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences.

For cloning and subcloning purposes, the vector may further comprise an origin of replication enabling the vector to replicate autonomously in a host cell such as a bacterial cell. Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in Bacillus. The origin of replication may be one having a mutation to make its function temperature-sensitive in a Bacillus cell (see, e.g., Ehrlich, 1978, *Proc. Natl. Acad. Sci. USA* 75:1433).

6.3.4 Marker Genes

To facilitate identification of transformants, the chimeric DNA construct desirably comprises a selectable or screenable marker gene as, or in addition to, a polynucleotide sequence according to the invention. The actual choice of a marker is not crucial as long as it is functional (i.e., selective) in combination with the plant cells of choice. The marker gene and the foreign or endogenous DNA sequence of interest do not have to be linked, since co-transformation of unlinked genes as, for example, described in U.S. Pat. No. 4,399,216 is also an efficient process in plant transformation.

Included within the terms selectable or screenable marker genes are genes that encode a "secretable marker" whose secretion can be detected as a means of identifying or selecting for transformed cells. Examples include markers that encode a secretable antigen that can be identified by antibody interaction, or secretable enzymes that can be detected by their catalytic activity. Secretable proteins include, but are not restricted to, proteins that are inserted or trapped in the cell wall (e.g., proteins that include a leader sequence such as that found in the expression unit of extensin or tobacco PR-S); small, diffusible proteins detectable, e.g. by ELISA; and small active enzymes detectable in extracellular solution (e.g., α-amylase, β-lactamase, phosphinothricin acetyltransferase).

6.3.5 Selectable Markers

Examples of bacterial selectable markers are the dal genes from *Bacillus subtilis* or *Bacillus licheniformis*, or markers that confer antibiotic resistance such as ampicillin, kanamycin, erythromycin, chloramphenicol or tetracycline resistance. Exemplary selectable markers for selection of plant transformants include, but are not limited to, a hyg gene which encodes hygromycin B resistance; a neomycin phosphotransferase (neo) gene conferring resistance to kanamycin, paromomycin, G418 and the like as, for example, described by Potrykus et al. (1985, *Mol. Gen. Genet.* 199: 183); a glutathione-S-transferase gene from rat liver conferring resistance to glutathione derived herbicides as, for example, described in EP-A 256 223; a glutamine synthetase gene conferring, upon overexpression, resistance to glutamine synthetase inhibitors such as phosphinothricin as, for example, described WO87/05327, an acetyl transferase gene from *Streptomyces viridochromogenes* conferring resistance to the selective agent phosphinothricin as, for example, described in EP-A 275 957, a gene encoding a 5-enolshikimate-3-phosphate synthase (EPSPS) conferring tolerance to N-phosphonomethylglycine as, for example, described by Hinchee et al. (1988, *Biotech.*, 6:915), a bar gene conferring resistance against bialaphos as, for example, described in WO91/02071; a nitrilase gene such as bxn from *Klebsiella ozaenae* which confers resistance to bromoxynil (Stalker et al., 1988, *Science,* 242:419); a dihydrofolate reductase (DHFR) gene conferring resistance to methotrexate (Thillet et al., 1988, *J. Biol. Chem.,* 263:12500); a mutant acetolactate synthase gene (ALS), which confers resistance to imidazolinone, sulfonylurea or other ALS-inhibiting chemicals (EP-A-154 204); a mutated anthranilate synthase gene that confers resistance to 5-methyl tryptophan; or a dalapon dehalogenase gene that confers resistance to the herbicide.

6.3.6 Screenable Markers

Preferred screenable markers include, but are not limited to, a uidA gene encoding a β-glucuronidase (GUS) enzyme for which various chromogenic substrates are known; a β-galactosidase gene encoding an enzyme for which chromogenic substrates are known; an aequorin gene (Prasher et al., 1985, *Biochem. Biophys. Res. Comm.*, 126:1259), which may be employed in calcium-sensitive bioluminescence detection; a green fluorescent protein gene (Niedz et al., 1995 *Plant Cell Reports,* 14:403); a luciferase (luc) gene (Ow et al., 1986, *Science,* 234:856), which allows for bioluminescence detection; a β-lactamase gene (Sutcliffe, 1978, *Proc. Natl. Acad. Sci. USA* 75:3737), which encodes an enzyme for which various chromogenic substrates are known (e.g., PADAC, a chromogenic cephalosporin); an R-locus gene, encoding a product that regulates the production of anthocyanin pigments (red colour) in plant tissues (Dellaporta et al., 1988, in *Chromosome Structure and Function,* pp. 263–282); an α-amylase gene (Ikuta et al., 1990, *Biotech.,* 8:241); a tyrosinase gene (Katz et al., 1983, *J. Gen. Microbiol.,* 129:2703) which encodes an enzyme capable of oxidising tyrosine to dopa and dopaquinone which in turn condenses to form the easily detectable compound melanin; or a xylE gene (Zukowsky et al., 1983, *Proc. Natl. Acad. Sci. USA* 80:1101), which encodes a catechol dioxygenase that can convert chromogenic catechols.

7. Introduction of Chimeric Construct into Plant Cells

A number of techniques are available for the introduction of DNA into a plant host cell. There are many plant transformation techniques well known to workers in the art, and new techniques are continually becoming known. The particular choice of a transformation technology will be determined by its efficiency to transform certain plant species as well as the experience and preference of the person practising the invention with a particular methodology of choice. It will be apparent to the skilled person that the particular choice of a transformation system to introduce a chimeric DNA construct into plant cells is not essential to or a limitation of the invention, provided it achieves an acceptable level of nucleic acid transfer. Guidance in the practical implementation of transformation systems for plant improvement is provided by Birch (1997, *Annu. Rev. Plant Physiol. Plant Molec. Biol.* 48: 297–326).

In principle both dicotyledonous and monocotyledonous plants that are amenable to transformation, can be modified by introducing a chimeric DNA construct according to the invention into a recipient cell and growing a new plant that harbours and expresses a polynucleotide according to the invention.

Introduction and expression of foreign or chimeric DNA sequences in dicotyledonous (broadleaved) plants such as tobacco, potato and alfalfa has been shown to be possible using the T-DNA of the tumour-inducing (Ti) plasmid of *Agrobacterium tumefaciens* (See, for example, Umbeck, U.S. Pat. No. 5,004,863, and International application PCT/US93/02480). A construct of the invention may be introduced into a plant cell utilising *A. tumefaciens* containing the Ti plasmid. In using an *A. tumefaciens* culture as a transformation vehicle, it is most advantageous to use a non-oncogenic strain of the *Agrobacterium* as the vector carrier so that normal non-oncogenic differentiation of the transformed tissues is possible. It is preferred that the *Agrobacterium* harbours a binary Ti plasmid system. Such a binary system comprises (1) a first Ti plasmid having a virulence region essential for the introduction of transfer DNA (T-DNA) into plants, and (2) a chimeric plasmid. The chimeric plasmid contains at least one border region of the T-DNA region of a wild-type Ti plasmid flanking the nucleic acid to be transferred. Binary Ti plasmid systems have been shown effective to transform plant cells as, for example, described by De Framond (1983, *Biotechnology,* 1:262) and Hoekema et al. (1983, *Nature,* 303:179). Such a binary system is preferred inter alia because it does not require integration into the Ti plasmid in *Agrobacterium*.

Methods involving the use of *Agrobacterium* include, but are not limited to: (a) co-cultivation of *Agrobacterium* with cultured isolated protoplasts; (b) transformation of plant cells or tissues with *Agrobacterium*; or (c) transformation of seeds, apices or meristems with *Agrobacterium*.

Recently, rice and corn, which are monocots, have been shown to be susceptible to transformation by *Agrobacterium* as well. However, many other important monocot crop plants, including oats, sorghum, millet, and rye, have not yet been successfully transformed using *Agrobacterium*-mediated transformation. The Ti plasmid, however, may be manipulated in the future to act as a vector for these other monocot plants. Additionally, using the Ti plasmid as a model system, it may be possible to artificially construct transformation vectors for these plants. Ti plasmids might also be introduced into monocot plants by artificial methods such as microinjection, or fusion between monocot protoplasts and bacterial spheroplasts containing the T-region, which can then be integrated into the plant nuclear DNA.

In addition, gene transfer can be accomplished by in situ transformation by *Agrobacterium*, as described by Bechtold et al. (1993, *C. R. Acad. Sci. Paris,* 316:1194). This approach is based on the vacuum infiltration of a suspension of *Agrobacterium* cells.

Alternatively, the chimeric construct may be introduced using root-inducing (Ri) plasmids of *Agrobacterium* as vectors.

Cauliflower mosaic virus (CaMV) may also be used as a vector for introducing of exogenous nucleic acids into plant cells (U.S. Pat. No. 4,407,956). CaMV DNA genome is inserted into a parent bacterial plasmid creating a recombinant DNA molecule that can be propagated in bacteria. After cloning, the recombinant plasmid again may be cloned and further modified by introduction of the desired nucleic acid sequence. The modified viral portion of the recombinant plasmid is then excised from the parent bacterial plasmid, and used to inoculate the plant cells or plants.

The chimeric nucleic acid construct can also be introduced into plant cells by electroporation as, for example, described by Fromm et al. (1985, *Proc. Natl. Acad. Sci., U.S.A,* 82:5824) and Shimamoto et al. (1989, *Nature* 338: 274–276). In this technique, plant protoplasts are electroporated in the presence of vectors or nucleic acids containing the relevant nucleic acid sequences. Electrical impulses of high field strength reversibly permeabilise membranes allowing the introduction of nucleic acids. Electroporated plant protoplasts reform the cell wall, divide and form a plant callus.

Another method for introducing the chimeric nucleic acid construct into a plant cell is high velocity ballistic penetration by small particles (also known as particle bombardment or microprojectile bombardment) with the nucleic acid to be introduced contained either within the matrix of small beads or particles, or on the surface thereof as, for example described by Klein et al. (1987, *Nature* 327:70). Although typically only a single introduction of a new nucleic acid sequence is required, this method particularly provides for multiple introductions.

Alternatively, the chimeric nucleic acid construct can be introduced into a plant cell by contacting the plant cell using mechanical or chemical means. For example, a nucleic acid can be mechanically transferred by microinjection directly into plant cells by use of micropipettes. Alternatively, a nucleic acid may be transferred into the plant cell by using polyethylene glycol which forms a precipitation complex with genetic material that is taken up by the cell.

There are a variety of methods known currently for transformation of monocotyledonous plants. Presently, preferred methods for transformation of monocots are microprojectile bombardment of explants or suspension cells, and direct DNA uptake or electroporation as, for example, described by Shimamoto et al. (1989, supra). Transgenic maize plants have been obtained by introducing the *Streptomyces hygroscopicus* bar gene into embryogenic cells of a maize suspension culture by microprojectile bombardment (Gordon-Kamm, 1990, *Plant Cell,* 2:603–618). The introduction of genetic material into aleurone protoplasts of other monocotyledonous crops such as wheat and barley has been reported (Lee, 1989, *Plant Mol. Biol.* 13:21–30). Wheat plants have been regenerated from embryogenic suspension culture by selecting only the aged compact and nodular embryogenic callus tissues for the establishment of the embryogenic suspension cultures (Vasil, 1990, *Bio/Technol.* 8:429–434). The combination with transformation systems for these crops enables the application of the present invention to monocots. These methods may also be applied for the transformation and regeneration of dicots. Transgenic sugarcane plants have been regenerated from embryogenic callus as, for example, described by Bower et al. (1996, *Molecular Breeding* 2:239–249).

Alternatively, a combination of different techniques may be employed to enhance the efficiency of the transformation process, e.g., bombardment with *Agrobacterium* coated microparticles (EP-A-486234) or microprojectile bombardment to induce wounding followed by co-cultivation with *Agrobacterium* (EP-A-486233).

8. Production and Characterisation of Differentiated Transgenic Plants 8.1 Regeneration The methods used to regenerate transformed cells into differentiated plants are not critical to this invention, and any method suitable for a target plant can be employed. Normally, a plant cell is regenerated to obtain a whole plant following a transformation process.

Regeneration from protoplasts varies from species to species of plants, but generally a suspension of protoplasts is made first. In certain species, embryo formation can then be induced from the protoplast suspension, to the stage of ripening and germination as natural embryos. The culture media will generally contain various amino acids and hormones, necessary for growth and regeneration. Examples of hormones utilised include auxins and cytokinins. It is sometimes advantageous to add glutamic acid and proline to the medium, especially for such species as corn and alfalfa. Efficient regeneration will depend on the medium, on the genotype, and on the history of the culture. If these variables are controlled, regeneration is reproducible. Regeneration also occurs from plant callus, explants, organs or parts. Transformation can be performed in the context of organ or plant part regeneration as, for example, described in *Methods in Enzymology*, Vol. 118 and Klee et al. (1987, *Annual Review of Plant Physiology,* 38:467), which are incorporated herein by reference. Utilising the leaf disk-transformation-regeneration method of Horsch et al. (1985, *Science,* 227: 1229, incorporated herein by reference), disks are cultured on selective media, followed by shoot formation in about 2–4 weeks. Shoots that develop are excised from calli and transplanted to appropriate root-inducing selective medium. Rooted plantlets are transplanted to soil as soon as possible after roots appear. The plantlets can be repotted as required, until reaching maturity.

In vegetatively propagated crops, the mature transgenic plants are propagated by the taking of cuttings or by tissue culture techniques to produce multiple identical plants. Selection of desirable transgenotes is made and new varieties are obtained and propagated vegetatively for commercial use.

In seed propagated crops, the mature transgenic plants can be self-crossed to produce a homozygous inbred plant. The inbred plant produces seed containing the newly introduced foreign gene(s). These seeds can be grown to produce plants that would produce the selected phenotype, e.g., early flowering.

Parts obtained from the regenerated plant, such as flowers, seeds, leaves, branches, fruit, and the like are included in the invention, provided that these parts comprise cells that have been transformed as described. Progeny and variants, and mutants of the regenerated plants are also included within the scope of the invention, provided that these parts comprise the introduced nucleic acid sequences.

It will be appreciated that the literature describes numerous techniques for regenerating specific plant types and more are continually becoming known. Those of ordinary skill in the art can refer to the literature for details and select suitable techniques without undue experimentation.

8.2 Characterisation

To confirm the presence of the polynucleotide of the invention in the regenerating plants, a variety of assays may be performed. Such assays include, for example, "molecular biological" assays well known to those of skill in the art, such as Southern and Northern blotting and PCR; a protein expressed by the polynucleotide of the invention may be assayed for sucrose isomerase activity as for example described herein.

9. Production of Isomaltulose

The present invention further relates to a process for the production of isomaltulose, using the polynucleotide or polypeptide sequences described herein or using variants or fragments thereof or using cells that produce such polypeptides, variants or fragments. The process involves contacting sucrose or a sucrose-containing medium or substrate with at least one member selected from (a) an isolated cell or organism which contains a DNA sequence encoding a protein with sucrose isomerase activity, for example a genetically modified bacterium or plant or an isolated cell or isolated population of cells that produce the protein naturally; (b) an extracellular product or cellular extract from such a cell or organism; and (c) a protein with sucrose isomerase activity in isolated form, under conditions such that the sucrose is at least partly converted by the sucrose isomerase into isomaltulose. Subsequently, the isomaltulose is obtained from the medium or the organism and purified as is known in the art. Methods for the industrial production of isomaltulose, for example using immobilised cells or sucrose isomerase contacted with a medium-containing sucrose, are well known (Cheetham et al. 1985, *Biotech. Bioeng.* 27: 471–481; Takazoe, 1989, Palatinose—an isomeric alternative to sucrose. In *Progress in Sweeteners* (Grenby, T. H., ed) Barking: Elsevier, pp. 143–167; and references respectively therein). The present invention improves these methods by providing novel sucrose isomerases with beneficial properties including a higher efficiency of isomaltulose production.

Furthermore, the present invention reveals for the first time the capacity to produce isomaltulose directly in plants. This is highly advantageous because it avoids the expense of extracting sucrose from plants and providing this as a substrate for conversion to isomaltulose by other organisms, extracts, or isolated enzymes through industrial fermentation. Instead, the sucrose produced by photosynthesis in plants genetically modified as described herein is converted to isomaltulose by sucrose isomerase activity in the plant tissue. The resulting isomaltulose is then harvested using procedures well established for the harvesting of other sugars, particularly sucrose, from plants. The plant materials with stored isomaltulose are first harvested, then crushed to expel the juice containing isomaltulose and/or passed through diffusion apparatus to extract the soluble isomaltulose from the insoluble plant materials. The isomaltulose is then purified by treatments to remove impurities and concentrated by evaporation and crystallisation stages well known to those skilled in the art (Cooke and Scott, 1993, *The Sugar Beet Crop: science into practice*. London: Chapman & Hall; Meade, 1977, *Cane Sugar Handbook*. New York: Wiley; Schiweck, Munir, Rapp, Schneider, Vogel, 1991, New developments in the use of sucrose as an industrial bulk chemical. In: *Carbohydrates as Organic Raw Materials* (FW Lichtenthaler, ed.) pp 57–94. Weinheim: VCH; and references respectively therein).

In order that the invention may be readily understood and put into practical effect, particular preferred embodiments will now be described by way of the following non-limiting examples.

EXAMPLES

Example 1

Isolation of Sucrose Isomerase-encoding Polynucleotides Using Oligonucleotide Primers Based on Regions Specified by Mattes et al.

This strategy was tested on a known sucrose isomerase expressing bacterium (*Erwinia rhapontici* Accession Number WAC2928), and 30 additional independent bacterial isolates. Degenerate PCR primers were designed based on regions specified by Mattes et al. (supra) as conserved regions from their analysis of sucrose isomerase genes known to them.

Forward primer consisted of the sequence extending from nucleotides 139–155 of SEQ ID NO: 1, 5'-tgg tgg aa(a,g) ga(g,a) gct gt-3' [SEQ ID NO: 38].

Reverse primer consisted of the sequence extending from nucleotides 625–644 of SEQ ID NO: 1, 5'-tcc cag tta g(g,a)t ccg gct g-3' [SEQ ID NO: 39].

Bacterial genomic DNAs were used as templates for PCR. The genomic DNAs were extracted according to Ausubel et al (1989, supra). The PCR reaction was carried out in a final volume of 50 μl comprising 100 ng DNA, 5 μL of 10×PCR buffer (Promega), 2 μL dNTPs (5 mM each NTP), forward primer and reverse primer 250 ng each, Taq polymerase 1 μL (Promega). Three parallel PCRs were run by using three different annealing temperatures: 46° C., 50° C. or 53° C. After an initial 1 min at 94° C., 35 cycles were performed consisting of 1 min at 94° C., 1 min at an annealing temperature and 1 min at 72° C.

After running the PCR products on a 1% agarose gel, the bands within the size range from 0.3 to 1.0 kb were recovered and cloned into pCR®2.1 vector using TOPO™TA Cloning® Kit (Invitrogen) following the instructions from the kit. Plasmid inserts were sequenced at the Australian Genomic Research Facility, using ABI PRISM Big Dye Terminator Cycle Sequencing Ready Reaction Kit, using universal primers of M13 Reverse or M13 Forward available on the vector. The GenBank database was searched by the FASTA program through ANGIS, using the sequenced DNAs as queries.

Using the primers from 'conserved regions' specified by Mattes et al. (supra), PCR products were amplified from *Erwinia rhapontici* and also from bacteria subsequently found to be negative for sucrose isomerase activity. Patterns of PCR products revealed by agarose gel electrophoresis included: no band from 2 isolates, one band from 3 isolates, and multiple bands from all other bacteria including *Erwinia rhapontici*. The DNAs in 12 bands, including six bands amplified from *Erwinia rhapontici*, were cloned and sequenced. None of the sequenced bands showed significant similarity to the sucrose isomerases, including the region of the gene from *Erwinia rhapontici* taught by Mattes et al. Most of the sequenced bands showed high similarities to known glucosidase genes.

Accordingly, it was concluded that the conserved sequences specified by Mattes et al. were not specific to sucrose isomerases, but were common to other classes of enzymes including glucosidases. As a consequence, these conserved sequences are not of direct use for the cloning of sucrose isomerases without onerous experimentation with PCR conditions and screening by other means to distinguish isomerase clones.

Example 2

Functional Screening for Bacteria that Convert Sucrose to Isomaltulose

Bacteria Collection and Isolation

Bacterial samples were collected from a range of environmental sites selected for their potential to yield novel, sucrose metabolising bacteria. In particular, sites were chosen subject to periodic sucrose availability, which might favour organisms able to convert sucrose to storage isomers such as isomaltulose. Around 100 samples from sites in SouthEast Queensland were collected into MIM liquid culture. MIM is 0.2% isomaltulose (6-O-α-D-Glucopyranosyl-D-fructofuranose) plus MM (minimum medium containing 0.5% $Na_2PO_4$, 0.45% $KH_2PO_4$, 0.1% $NH_4Cl$, 0.05% $MgSO_4.7H_2O$, 0.005% Ferric Ammonium Citrate and 0.0005% $CaCl_2$). Following growth on an orbital shaker at 200 rpm for 2 hours at room temperature, 100 μL samples were streaked onto MSM (MM plus 4% sucrose) agar plates and grown overnight at 28° C. Following this two-stage enrichment, morphologically different colonies were isolated onto separate fresh plates of LB or MSM for further growth (578 colonies in total). After streaking to ensure purity of single-colony isolates, they were transferred in duplicate to both a replica patch plate and a 30 mL universal tube containing 5 mL SLB (LB containing 4% sucrose) for further functional screening in an assay that preferentially reveals organisms with higher capacity for isomaltulose production.

Example 3

Sample Preparation for Aniline/Diphenylamine Assay

The cultures grown overnight in 5 mL SLB were centrifuged at a speed of 10,000×g for 10 minutes at room temperature. The supernatant was carefully poured off and 2 mL of a 50% sucrose solution in citrate/phosphate buffer (pH 6) was added. Cells were gently resuspended and incubated at 28° C. in a shaker for 48 hours. Following incubation, 1.5 mL culture was transferred to a fresh Eppendorf tube, boiled for 15 minutes at 100° C. and centrifuged at 16,000×g for 20 minutes at room temperature. Without touching the pellet, the supernatant was saved to a fresh tube for aniline/diphenylamine assay and capillary electrophoresis.

Example 4

Aniline/Diphenylamine Assay

Samples were spotted evenly around the outside edge of a Whatman #1 filter paper with a positive control (from *Erwinia rhapontici*) and a negative control (from *Escherichia coli*) placed in the center. After the samples were spotted onto the filter paper, they were left to dry for 15 minutes while the color-developing reagent was prepared.

The reagent was prepared as follows:
a. 4 mL Aniline made up to 100 mL using A.R. acetone;
b. 4 g Diphenylamine made up to 100 mL using A.R. acetone;
c. 20 mL of 85% Orthophosphoric acid.

Components (a) and (b) were prepared separately in a fume cabinet ensuring complete mixing/dissolving of the aniline/diphenylamine respectively in acetone before they were combined in a glass beaker, after which the acid was added. After initial addition of the acid a cloudy white precipitate forms, which dissolves after vigorous swirling to yield a clear brown solution.

The prepared filters were passed through the "developer", ensuring that each filter received even and equal exposure. The filters were then allowed to dry on paper toweling in the fume-hood for 15 minutes, then heated in an 80° C. drying oven for 10 minutes. The results (color of spots) were recorded or photographed using a digital camera.

If isomaltulose was present, the reaction yielded a yellow to brownish yellow spot due to the 1,6-linked glucosaccharide; whereas glucose yielded a dark grey spot, fructose yielded a silver-grey spot, and sucrose yielded a purple-brown spot due to the 1,2-linkage. The intensity of the color depends on the concentration of the sugars present. Twelve candidates were selected from the 578 colonies as indicated by the aniline/diphenylamine assay test. The identity of the isomaltulose product from the selected isolates was then verified by quantitative analysis using capillary electrophoresis to resolve and identify related metabolites.

Example 5

Sample Preparation for Capillary Electrophoresis

The ionic materials in the supernatant used for aniline/diphenylamine assay need to be removed before loading to the capillary for further analysis. This was done by passing through a Strong Cation Exchange (Bond Elut-SCX, 1210-2013) and a Strong Anion Exchange (Bond Elut-SAX, 1210-2017) column purchased from Varian. The columns were preconditioned by rinsing with one volume of methanol, followed by one volume of water, with the rinses being forced through the columns with the aid of a syringe.

The bacterial supernatant was diluted 150-fold using sterile Milli-Q (SMQ) water before processing first through the SCX and then the SAX column. One mL of the diluted supernatant was placed in the SCX column. The sample was forced through the column with the aid of a 50-mL syringe. The eluate was collected directly into the SAX column. The sample was similarly forced through with the final eluate collected in a 1.5-mL Eppendorf tube.

Example 6

Capillary Electrophoresis

Separation by high performance capillary electrophoresis (HPCE), was performed using a Beckman P/ACE 5000 Series C.E. System utilising a 190 to 380 nm light source from a deuterium lamp along with and a Beckman P/ACE UV Absorbance Detector (254 nm [∀ 10 nm] filter wheel) for sample detection.

Capillaries were bare, fused silica capillaries, I.D. 50 µm, O.D. 363 µm (Supelco Cat. #70550-U). Total capillary length was 77 cm, and length inlet to detector window was 69 cm. The capillary detector window was made by burning the coating off the capillary using a match, and wiping with methanol.

To achieve maximum reproducibility of migration times, the capillary was re-conditioned every morning and evening using the following rinsing procedure: 2 min with SMQ, 10 min 0.1 M HCl, 2 min SMQ, 10 min 0.1 M NaOH, 2 min SMQ, 15 min 0.5 M ammonia and 2 min SMQ. All solutions were dissolved/diluted in SMQ and filtered through a 0.45 µm Micropore filter.

An alkaline copper sulphate electrolyte with direct detection based on UV absorbance was employed to resolve and detect low concentrations of sucrose and its isomer isomaltulose, in addition to other sugars including glucose and fructose that are expected in cell extracts. Using an electrolyte consisting of 6 mM copper (II) sulphate and 500 mM ammonia, pH 11.6, both the separation and the direct UV detection of neutral sugars is achieved based on the chelation reaction of the sugar with copper (II) under alkaline conditions.

The electrolyte buffer (EB) was made fresh at the beginning of each day and degassed for 15 min before use. After conditioning, the capillary was rinsed with EB for 15 min. The capillary was also rinsed with EB for 10 minutes between sample separations. Programmed parameters for batch runs are listed in Table 1. A positive and a negative control as described above were included in each sample. In addition, standards (consisting of sucrose and isomaltulose) were run before the first, and after the last samples, so that differences in migration time due to factors such as EB depletion, capillary heating etc. could be measured and corrected.

TABLE 1

Parameters for batch run of capillary electrophoresis

| Function | Duration | Inlet Vial | Outlet Vial | Comment |
|---|---|---|---|---|
| EB Rinse | 5 min | 11 | 10 | Forward, 20 psi |
| Pressure Inject | 5 sec | Sample Vial | 10 | Forward, 20 psi |
| Separate | 30 min | 12 | 1 | 25 KV, 254 nm |
| EB Rinse | 5 min | 13 | 10 | Forward, 20 psi |

Three isolates named as 349J, 14s and 68J were confirmed as having the ability to convert sucrose into isomaltulose. The diluted supernatants from these three positive isolates were retested after being spiked separately with either 5 mM sucrose, 0.5 mM isomaltulose, 0.5 mM fructose or 0.5 mM glucose to verify the identity of peaks in the sample based on comigration with a known sugar.

Example 7

Bacterial Genomic Library Construction

Cosmid vector SuperCos 1 (Stratagene) was used for genomic library construction from an Australian isolate of *Erwinia rhapontici* (Accession Number WAC2928), and bacterial isolates 14S, 68J and 349J. The vector accommodates genomic DNA fragments ranging from 30 to 45 kb.

Example 8

Preparation of Genomic DNA Insert

Because large fragments are required for cloning in the SuperCos 1 vector, the genomic DNA was extracted essentially by method of Priefer et al. (1984, Cloning with cosmids. In *Advanced Molecular Genetics* (Pühler, A. and Timmis, K. N., eds) Berlin: Springer-Verlag, pp. 190-201) to obtain high molecular weight (~150 kb) DNA before digestion. The hooked DNA was dissolved in TE buffer at 65° C. for 3 hours or at 4° C. for 2 days without shaking. The molecular size was estimated by checking on a 0.4% agarose gel. In order to clone into the BamH I site of the SuperCos 1 vector, the chromosomal DNA was partially digested with restriction endonuclease Sau 3A. A series of test partial digests was conducted to determine the ideal conditions for obtaining the desired insert size range. Ten µg of genomic DNA in a 135 µL volume reaction using 1×Sau 3A buffer was pre-equilibrated at 37° C. for 5 minutes. Then, 0.5 units of Sau 3A was added, and after 0, 5, 10, 15, 20, 25, 30, 40 minutes, aliquots (15 µL) were removed and the reaction was immediately stopped at 68° C. for 20 minutes. The aliquots were loaded on 0.5% agarose gel for electrophoresis. The optimal digestion period was determined for an average fragment size of 50 kb. The reaction was scaled up to 50 µg of genomic DNA in a 675 µL total volume. After digestion, 13 µL of 0.5 M EDTA, pH 8.0 was added to the sample. After a phenol/chloroform extraction, the DNA was precipitated by addition of 1/10 volume of sodium acetate (3M, pH 5.2) and 2.5 volume of ethanol according to Sambrook et al. (1989). The pellet was resuspended in 450 µL 1× CIAP buffer and the DNA was CIAP treated for 60 minutes at 37° C. Another phenol/chloroform extraction was repeated to the CIAP treated DNA. The DNA was finally dissolved in 30 µL TE buffer for ligation.

Example 9

Preparation of Vector DNA

After 20 µg SuperCos 1 vector was digested by XbaI at 37° C. for 3 hours, one unit CIAP per µg DNA was added to the reaction and incubated another hour at 37° C. Phenol/chloroform extraction and ethanol precipitation of the treated DNA using the method described above were performed. The XbaI/CIAP treated SuperCos 1 DNA was resuspended in TE buffer and checked on 0.8% agarose gel to see the single linear band with size of 7.6 kb. The vector DNA was further digested with BamHI, extracted with phenol/chloroform, ethanol precipitated, resuspended in TE buffer at 1 µg/mL for ligation.

Example 10

Ligation and Packaging of DNA

In a 15 µL volume, 2.5 µg Sau 3A partially digested bacterial genomic DNA and 1.0 µg SuperCos 1 vector DNA treated with Xba I/CIAP/BamHI were heated at 70° C. for 5 minutes. Then 2 µL 10 mM ATP, 2 µL 10×ligation buffer and 1 µL T4 DNA ligase (Invitrogen) were added to make up to 20 µL in total volume. After 4 hours incubation at room temperature, the ligation was put at 4° C. overnight. Ligation efficiency was viewed by running 2 µL reaction against unligated mixture of vector and insert DNAs on a 0.8% agarose gel.

One fourth of the ligation was in vitro-packaged according to the manufacturer's instruction (Gigapack III Gold Packaging Extract, Stratagene).

Host cells of *E. coli* NM554 (Stratagene) were grown in LB medium with 0.2% maltose and 10 mM $MgSO_4$ at 37° C. with shaking from a single colony to an $OD_{600}$ value of 1.0. The cells were harvested by centrifugation at 2,000×g at 4° C. for 10 minutes, then gently resuspended in 10 mM $MgSO_4$ to $OD_{600}$ value of 0.5. After 10 µL packaged cosmid library was mixed with 50 µL NM554 cells in a 1.5 mL tube, they were incubated at room temperature for 30 minutes, then 400 µL LB was added to the tube. To allow expression of antibiotic resistance, the cells were incubated at 37° C. for another hour with gentle shaking once every 15 minutes. The cells were centrifuged for 30 seconds and gently resuspend in 100 µL fresh LB broth. Fifty µL was spread on a LB plate with 50 µg/mL ampicillin.

Example 11

Functional Screening of Cosmid Libraries

After functional screening of 600 colonies from each of the four cosmid libraries, aniline/diphenylamine assay and CE as described above, 4 clones from *Erwinia rhapontici*, 4 clones from 14S, 3 clones from 349J and 3 clones from 68J showed ability of conversion from sucrose to isomaltulose.

Example 12

Subcloning and Sequencing

Cosmid DNAs from positive colonies were prepared following the method of Sambrook et al (1989). To find the smallest functional fragment containing sucrose isomerase, the subclone insert of cosmid DNA was prepared through partial digestion by EcoR I, BamH I or Hind III separately. Freshly digested pZerO™-2 vector (Invitrogen) by EcoR I, BamH I or Hind III were used for ligation with the inserts. All cloning procedures such as ligation and transformation into Top 10 *E. coli* strain followed the instructions provided by Invitrogen. Two hundred transformants of each ligation were picked, patched and grown for functional screening by aniline/diphenylamine assay as described above. The functionally positive subclones were further confirmed by CE analysis. Plasmid DNAs were isolated from the CE confirmed positives to check digest pattern on EcoR I, BamH I or Hind III. The digested fragments from cosmid insert were further subcloned into pZerO™-2 vector, assayed and sized as described above to obtain the functional clones with the smallest inserts for sequencing.

Plasmid inserts were sequenced at the Australian Genomic Research Facility, using ABI PRISM Big Dye Terminator Cycle Sequencing Ready Reaction Kit. For the first round sequencing, universal primers (Sp6, T7, M13 Reverse or M13 Forward) starting the sites available on the pZerO™-2 vector were used, then custom primers were used for sequence extension. Sequences were conducted and confirmed from both strands of the DNA.

Example 13

Expression of the Three Sucrose Isomerase Genes in E. coli

Based on the sequences of the genes cloned by functional screening as described above, three pairs of primers were designed for subcloning the three sucrose isomerase genes into expression vector pET 24b. By PCR, non-coding regions and leader sequences were deleted and an artificial start codon was incorporated. Each forward primer: 1) includes a start codon, 2) creates a plant-like context for translation start, 3) incorporates a BamH I restriction site for easily cloning and matching open reading frame of the gene. Each reverse primer incorporates a Kpn I restriction site and includes a stop codon. The primer base pairs are as follows:

```
Erwinia rhapontici forward:  5'-gga tcc aac aat ggc aac cgt tca gca atc aaa tg-3'   [SEQ ID NO: 15]

14S forward:                 5'-gga tcc aac aat ggc aac cgt tca caa gga aag tg-3'   [SEQ ID NO: 17]

68J forward:                 5'-gga tcc aac aat ggc aac gaa tat aca aaa gtc c-3'    [SEQ ID NO: 13]

Erwinia rhapontici reverse:  5'-ata ggt acc tta ctt aaa cgc gtg gat g-3'             [SEQ ID NO: 16]

14S reverse:                 5'-ata ggt acc tta ccg cag ctt ata cac acc-3'           [SEQ ID NO: 18]

68J reverse:                 5'-ata ggt acc tca gtt cag ctt ata gat ccc-3'           [SEQ ID NO: 14]
```

High fidelity DNA polymerase pfu (Stratagene) was used for PCR. The PCR products were directly cloned into pCR®2.1 vector using TOPO™TA Cloning® Kit (Invitrogen) following the instructions from the kit.

The three sucrose isomerase genes in the pCR®2.1 vector were cut and cloned into pGEM®-3Zf(+) then into pET 24b vector (Novagen) for expression in E. coli BL21(DE3) strain. Five mL LB medium with 50 µg/mL kanamycin was used for the BL21(DE3) cell culture. Fifteen cultures per construct were set up initially. Cells were grown at 37° C. at 225 rpm shaking. Six to ten cultures per construct, with $OD_{600}$ 1.000±0.005, were selected for further induction. After 0.5 mL was sampled from each culture, IPTG was added to the culture to a final concentration of 1.0 mM. Incubation of the cultures was continued for another 3 hours. The induced cultures only with $OD_{600}$ 1.750±0.005 were further selected for sucrose conversion analysis and protein measurement, allowing analysis of three replicate cultures per construct. From each of the selected IPTG-induced cultures, 1.5 mL was sampled for protein quantification, 0.5 mL for protein SDS-PAGE, 1.0 mL for quantification of conversion efficiency from sucrose into isomaltulose.

Example 14

Protein Assay

The cells were harvested by centrifugation (3,000×g, 4° C., 10 min). The cell pellet was resuspended in 50 µL of 50 mM Tris-HCl pH 8.0, and 2 mM EDTA, then recentrifuged. The cell pellet was immediately frozen in liquid nitrogen and stored at −70° C. Cells were suspended in 0.5 mL extraction buffer (20 mM Tris-HCl, pH 7.4, 200 mM NaCl, 1 mM EDTA, 1 mM azide, 10 mM β-mercaptoethanol), then lysed by sonication (9×15 s pulse at 50 watts from a Branson Sonifier 450 microprobe), and centrifuged (10,000×g, 4° C., 10 min). The supernatant was filtered through an Acrodisc® 32 Super® 0.45 µm membrane filter unit (GelmanScience).

Protein was assayed according to Bradford (1976, *Anal. Biochem.* 72: 248–254) using bovine serum albumin as a standard. Ten µl protein extraction described above was mixed with 90 µl 0.15 M NaCl and 1 mL Coomassie brilliant blue solution (100 mg Coomassie Brilliant Blue G-250 in 50 mL 95% ethanol+100 mL of 85% phosphoric acid+850 mL SMQ). $A_{595}$ was determined and the protein content was calculated from the standard curve.

Example 15

SDS-Page

SDS polyacrylamide gels were polymerised and run as described by Laemmli (1970, *Nature* 227: 680–685). Protein samples were heated at 100° C. for 5 min in 1×SDS-PAGE sample buffer (25 mM Tris-HCl pH 6.8, 1% (w/v) SDS, 5% (v/v) β-mercaptoethanol, 10% (v/v) glycerol, 0.005% (v/v) bromophenol blue), centrifuged at 12,000×g for 1 min and the supernatants were applied to the gels. Each sample was loaded into two adjacent lanes. After running, one lane from the gel was stained in 0.025% (w/v) Coomassie Blue R-250, destained in 30% (v/v) methanol, 10% (v/v) acetic acid, then expressed sucrose isomerase was cut from the unstained lane corresponding to the relative migration position of the stained gel lane. The sucrose isomerase protein was eluted from the gel slice by immersion into extraction buffer overnight at 4° C. with gentle shaking. The eluted sucrose isomerase was quantified using the protein quantification method described above.

Example 16

Conversion Ratio from Sucrose into Isomaltulose by Sucrose Isomerase Expressed in E. coli The 1.0 mL culture was centrifuged, then resuspended in citrate/phosphate (pH 6.0) buffered 50% sucrose solution and assayed for isomaltulose conversion by CE analysis as described above. Conversion ratio was calculated by sucrose peak area and isomaltulose peak area normalised against standards of known concentration, using the software of Beckman P/ACE 5000 Series C.E. System.

Example 17

Construct DNA Preparation

The sucrose isomerase (SI) gene insert in the pET 24b vector was further cloned between the Ubi promoter from the maize ubi-1 gene (Christensen and Quail, 1996, *Transgen. Res.* 5: 215-218) and the *Agrobacterium* nos terminator (Bevan et al., 1983, *Nature* 304: 183–187) to drive expression in sugarcane cells.

Plasmids with the sucrose isomerase genes (pU3ZErw, pU3Z14s or pU3Z68J) and the aph A construct plasmid pEmuKN (as a selectable marker) were isolated by alkaline extraction (Sambrook et al., 1989, supra), and dissolved in TE buffer. Plasmid intactness and absence of genomic DNA or RNA were checked by gel electrophoresis and concentration was measured by spectrophotometry. The sucrose isomerase (UbiSI) gene construct and selectable marker construct were co-precipitated onto tungsten microprojectiles and introduced into sugarcane callus, followed by selection for transformed callus, and regeneration of transgenic plants, essentially described by Bower et al. (1996, *Molec. Breed.* 2: 239–249).

Example 18

Particle Bombardment

Precipitation reactions were conducted by adding the following at 4° C. in turn to a 1.5 mL microfuge tube: 5 μL pEmuKN plasmid DNA (1 mg/mL), 5 μL UbiSI plasmid DNA (1 μg/μL), 50 μL tungsten (Bio-Rad M10, 100 μg/μL), 50 μL $CaCl_2$ (2.5M), 20 μL spermidine (100 mM free base). The preparation was mixed immediately after addition of each reagent, with minimal delay between addition of $CaCl_2$ and spermidine. The tungsten was then allowed to settle for 5 minutes on ice, before removal of 100 μL of supernatant and resuspension of the tungsten by running the tube base across a tube rack. Suspensions were used within 15 minutes, at a load of 4 μL/bombardment, with resuspension of the particles immediately before removal of each aliquot. Assuming the entire DNA is precipitated during the reaction, this is equivalent to 1.3 μg DNA/bombardment, on 667 μg tungsten/bombardment.

Embryogenic callus from sugarcane cultivar Q117 was used for bombardment. Particles were accelerated by direct entrainment in a helium gas pulse, through the constriction of a syringe filter holder into the target callus in a vacuum chamber as described by Bower et al. (1996, supra). The tissue was osmotically conditioned for four hours before and after bombardment. After 48 hours recovery on solid medium without antibiotics, the bombarded callus was transferred to medium with 45 mg/L Geneticin for selection, callus development and plant regeneration.

Example 19

Functionality of the Transformants in Conversion of Sucrose

Samples were collected from independent transgenic callus and ground under liquid nitrogen. Also, untransformed Q117 callus and callus transformed with Ubi-luc were used as negative controls. The ground tissue was centrifuged at 16,000×g at 4° C. to pellet cell debris. The supernatant was diluted 10 folds in SMQ, then boiled for 20 minutes. After another centrifugation to remove denatured proteins, the supernatant was passed through Bond Elut™ SCX and SAX. CE analysis was performed as described above.

Results and Discussion Relating to Examples 1–19

Three Bacterial Strains with Sucrose Isomerase Activity were Isolated

An Australian isolate of *Erwinia rhapontici* (Accession Number: WAC 2928) was used as a positive control for isomaltulose production, because this species has previously been shown to produce a sucrose isomerase enzyme that converts sucrose to isomaltulose (Cheetham, 1985, supra). From a total of 578 bacteria isolated through the enrichment procedure, three strains yielded yellow colour reaction distinctive for isomaltulose in the aniline/diphenylamine assay, and a novel peak in the CE assay corresponding to the isomaltulose standard and to that of *Erwinia rhapontici* (FIG. 1). These strains, designated 14S, 68J and 349J are all Gram-negative bacteria able to use either sucrose or isomaltulose as sole carbon source. All three strains grow well at 22-30° C., and 68J also grows slowly at 4° C.

Three Sucrose Isomerase Genes were Functionally Cloned and Sequenced

Figure 2:
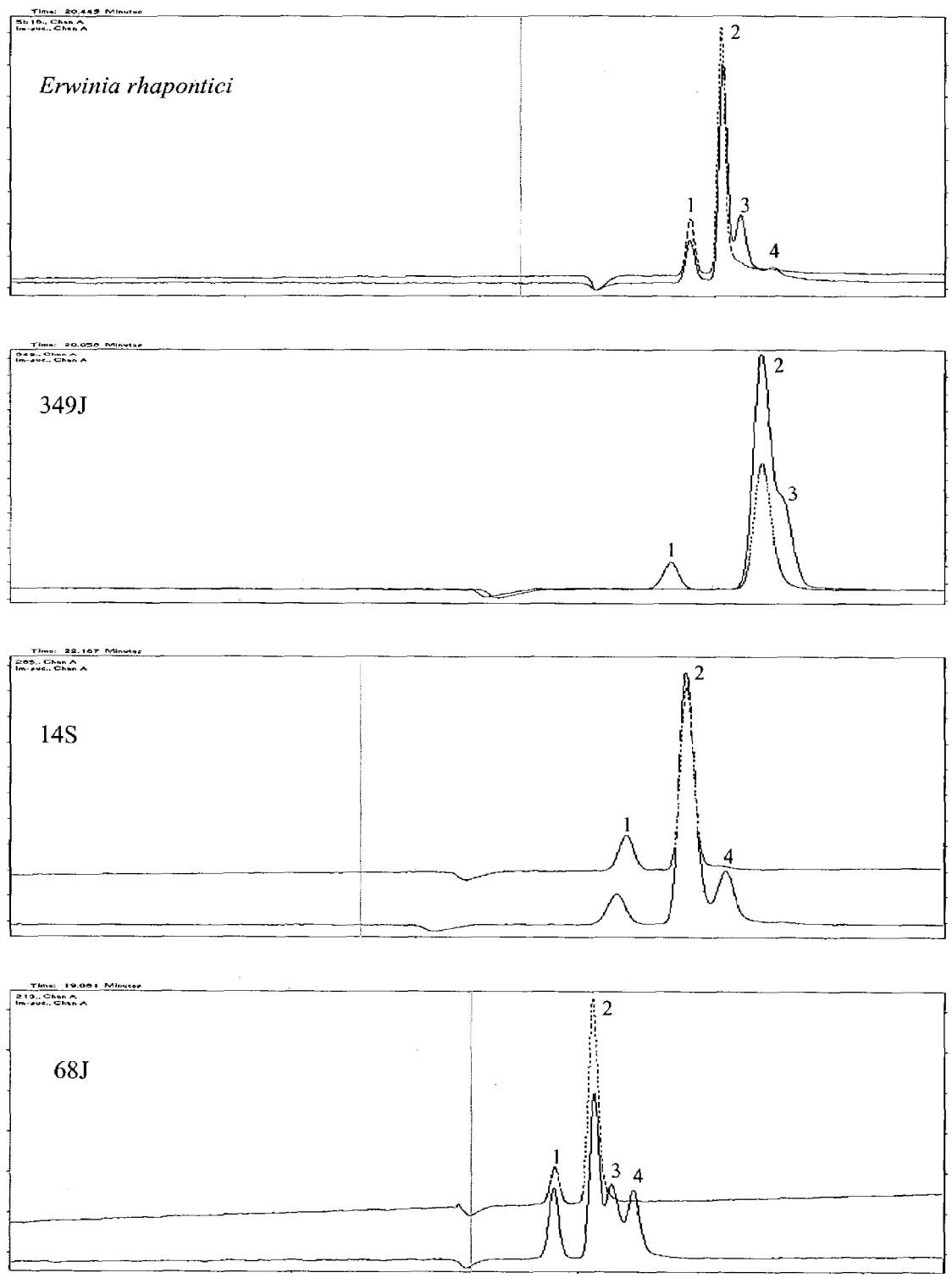
FIG. 2 is a graphical representation showing the conversion of sucrose to isomaltulose in *E. coli* expressing sucrose isomerase genes cloned in SuperCos™ vector. Peaks: 1—sucrose, 2—isomaltulose, 3—fructose, 4—glucose. "Dotted" electrophoretogram is sucrose and isomaltulose standards.

Functional screening of genomic cosmid libraries of *Erwinia rhapontici*, 14S, 349J and 68J in *E. coli* yielded clones able to convert sucrose to isomaltulose (FIG. 2). After several cycles of subcloning into pZerO™-2 vector and functional screening, the smallest functional inserts in pZerO™-2 vector ranged from 3 to 5 kb.

Sequence from *Erwinia rhapontici* (FIG. 3) showed a 1899 bp ORF (SEQ ID NO: 1) encoding 632 amino acids (FIG. 5) (SEQ ID NO: 2). First strand sequencing revealed a gene in the 349J subclone with 99% identity to this *Erwinia rhapontici* ORF, so sequencing of 349J was stopped. Sequence from 14S revealed a 1797 bp ORF (SEQ ID NO: 7) encoding 598 amino acids (SEQ ID NO: 8). Database searching by FASTA showed that 1305 bp of the SI gene from *Erwinia rhapontici*, and the full length of the SI gene from 14S had been disclosed by Mattes et al. (supra). Sequence from 68J (FIG. 4) indicated a novel SI gene with an ORF of 1797 bp (SEQ ID NO: 7). At the nucleotide level, it has less than 70% identity to known sucrose isomerases, either with or without leader fragment (Table 2). At the amino acid level, the identity to other sucrose isomerases is between 63.4% to 70.6% with leader, or 64.6% to 73.7% without leader. The 68J predicated SI gene product is a protein with 598 amino acids (FIG. 6) (SEQ ID NO: 8), Mr of 69291 and isoelectric point 7.5 due to 78 basic and 69 acidic amino acid residues. Phylogenic analysis of amino acid sequences shows the relatedness between 68J SI gene and known genes. All sucrose isomerase genes and glucosidases share conserved products of the domains for sugar binding. As a result the conserved sequences and corresponding primers described by Mattes et al. (supra) are not specific for sucrose isomerases and would yield many non-SI genes from different organisms. The SI gene of 68J shows nearly the same level of nucleotide identity to various glucosidases as it does to known SI genes of *Pseudomonas mesoacidophila*.

TABLE 2

Comparison between characteristics of 68J, other sucrose isomerases, sucrose isomerase fragments, and a glucosidase

| Sequence accession # | Species | Notes | ORF length n.t. (bps) | ORF length Pep. (a.a.) | Peptide with leader Similarity (%) | Peptide with leader Identity (%) | Peptide without leader Similarity (%) | Peptide without leader Identity (%) | Nucleotide identity (%) With leader | Nucleotide identity (%) Without leader |
|---|---|---|---|---|---|---|---|---|---|---|
| UQ 68J | | Full length UQ isolate | 1797 | 598 | | | | | | |
| a45846 Sudz #1 | Protaminobacter rubrum | Full length | 1890 | 629 | 81.1 | 70.3 | 83.0 | 73.3 | 68.2 | 69.4 |
| a45854 Sudz #9 | Protaminobacter rubrum (variant) | Full length | 1803 | 600 | 81.5 | 70.6 | 83.4 | 73.7 | 68.2 | 69.4 |
| a45856 Sudz #11 | Enterobacter species | Full length | 1794 | 597 | 80.7 | 68.5 | 82.6 | 71.4 | 67.3 | 68.5 |
| UQ 281 | Erwinia rhapontici | Full length UQ isolate | 1899 | 632 | 79.6 | 68.8 | 82.1 | 72.0 | 66.4 | 67.7 |
| a45858 Sudz #13 | Pseudomonas mesoacidophila | Full length Isomerase | 1782 | 593 | 75.5 | 63.4 | 76.3 | 64.6 | 60.9 | 62.4 |
| a45860 Sudz #16 | Pseudomnonas mesoacidophila | Full length Hydrolase | 1704 | 567 | No leader sequence | | 70.4 | 52.4 | — | 56.4 |
| a45850 Sudz #3 | Enterobacter species | PCR fragment of Sudz #11 (nonfunctional) | 471 | 157 | — | — | 89.1* | 81.4* | — | 75.4* |
| a45848 Sudz #2 | Erwinia rhapontici | N-terminal region of UQ 281 homolog (nonfunctional) | 1305 | 435 | 84.2* | 74.9* | 87.0* | 78.5* | 67.2* | 72.4* |
| Bcol6gl | Bacillus cereus | Glucosidase | 1677 | 599 | No leader sequence | | 68.2 | 48.8 | — | 53.2 |

*Comparison between 68J and nonfunctional fragments from incomplete sucrose isomerase genes.
Sudz # sequences are disclosed in patent to Sudzucker (Mattes et al.).

Figure 7:
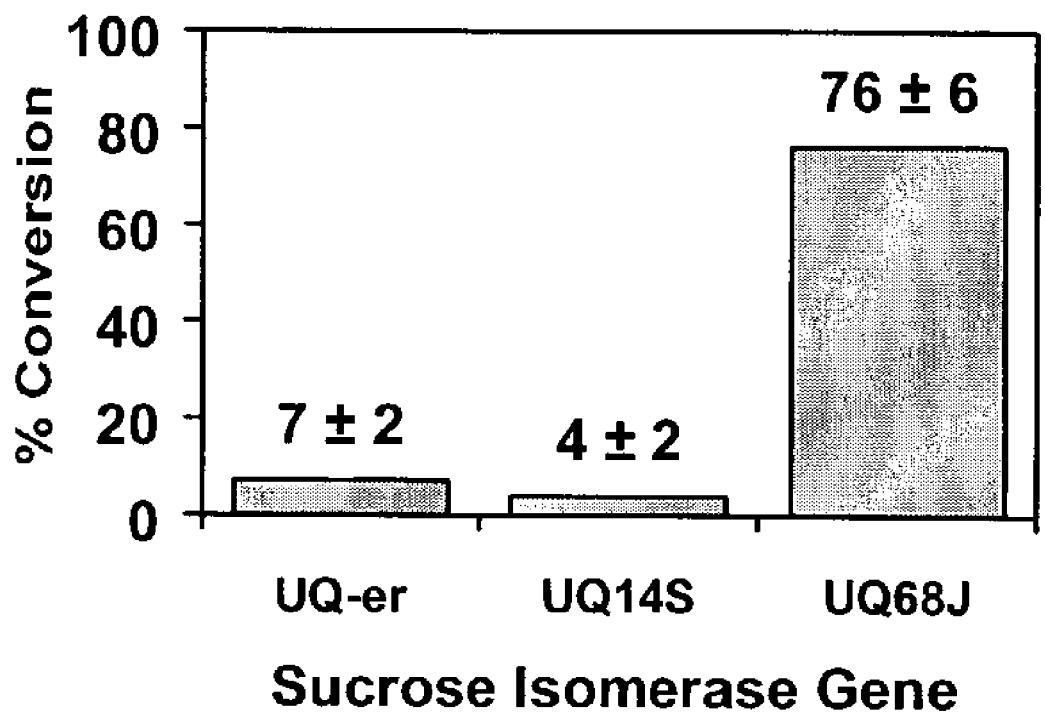
FIG. 7 is a graphical representation showing the efficiency of conversion from sucrose to isomaltulose by *E. coli* expressing cloned sucrose isomerase genes. Results are means±standard errors derived from 3 replications.

Sucrose Isomerase from 68J Showed the Highest Conversion Efficiency Among the Tested Isomerases When the SI genes from *Erwinia rhapontici*, 14S and 68J were arranged for expression using the same vector (same promoter, start codon and termination sequences), there was no significant difference in total protein content or in expression level of sucrose isomerases, at around 10% of total protein (Table 3). However, the conversion efficiency from sucrose to isomaltulose by the cloned 68J gene product is 10 times that of the *Erwinia rhapontici* and 18 times that of the 14S gene products (FIG. 7). In addition, the sucrose isomerase of 68J generated relatively smaller proportions of glucose and fructose than that of 14S and *Erwinia rhapontici*. All other factors during gene expression and enzyme activity quantification were identical: the same ATG start codon context for gene constructs, the same vector pET 24b, the same host cell strain BL21(DE3), the same culture conditions, the same cell density before and after IPTG induction, the same amount of cells used for sucrose conversion, the same amount of total protein loaded on to SDS-PAGE and the same volume of supernatant with the same total protein content loaded on to CE. The experiment was performed three times with the same outcomes.

The experimental results show high potential of the sucrose isomerase from 68J in industrial applications for isomaltulose production.

TABLE 3

Total protein contents and assumed sucrose isomerase protein contents in *E. coli* cells with a SI gene of *Erwinia rhapontici*, 14S or 68J#.

| Sucrose isomerase | Total protein content (% dry weight) | Sucrose isomerase content (% total proteins*) |
|---|---|---|
| *Erwinia rhapontici* | 15.97 ± 1.63 | 12.2 ± 1.5 |
| 14S | 15.75 ± 1.38 | 11.8 ± 0.5 |

TABLE 3-continued

Total protein contents and assumed sucrose isomerase protein contents in *E. coli* cells with a SI gene of *Erwinia rhapontici*, 14S or 68J#.

| Sucrose isomerase | Total protein content (% dry weight) | Sucrose isomerase content (% total proteins*) |
|---|---|---|
| 68J | 16.12 ± 1.79 | 12.4 ± 1.2 |
| Control | 14.36 ± 2.04 | 1.9 ± 0.6 |

Results are means ± standard errors derived from 3 replications.
*Including background of approximately 2% proteins that migrated with the sucrose isomerase.

Figure 8:
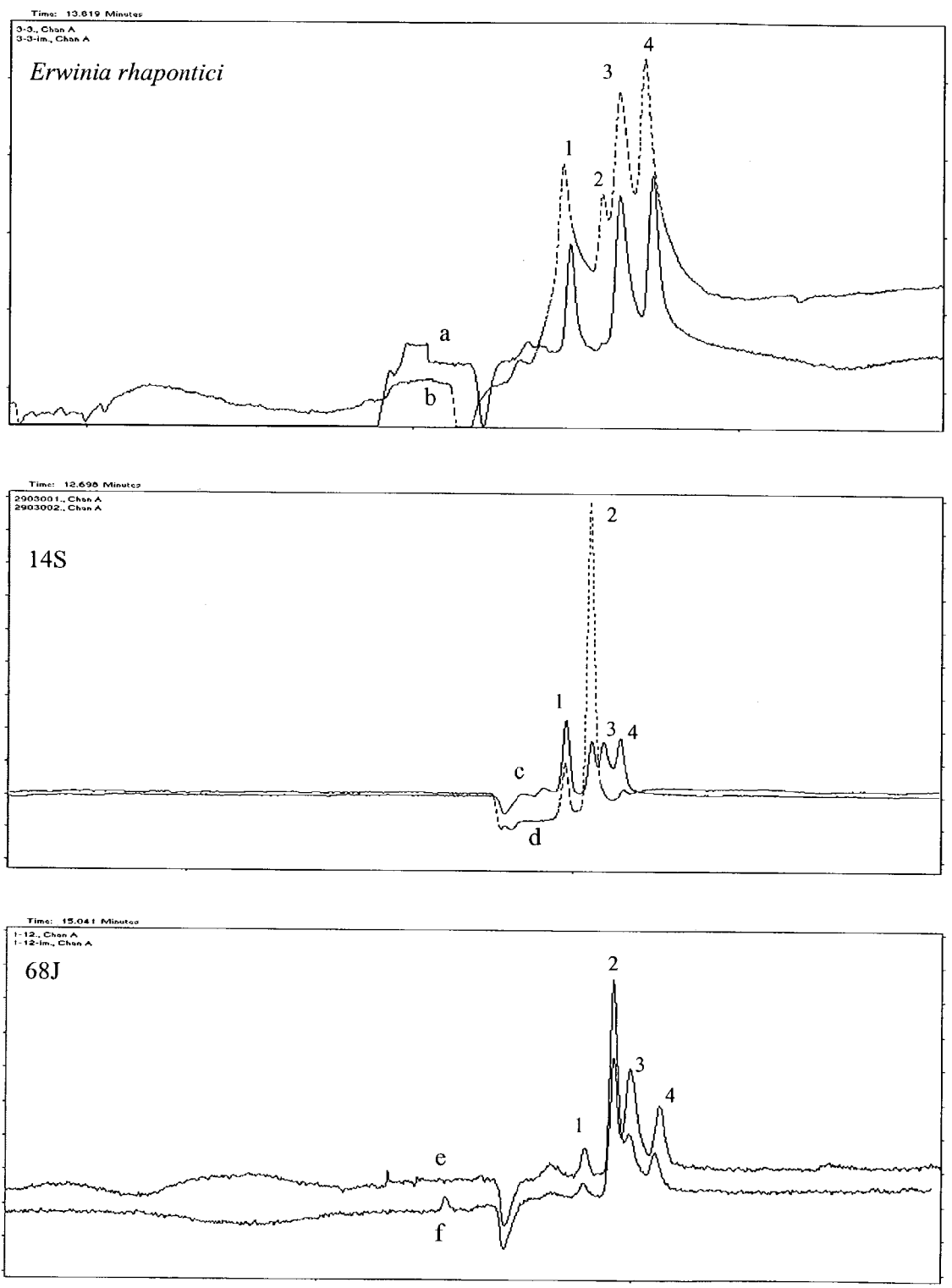
FIG. 8 is a graphical representation showing the conversion of sucrose to isomaltulose in stably transformed sugarcane calli expressing cloned sucrose isomerase genes. Peaks: 1—sucrose, 2—isomaltulose, 3—fructose, 4—glucose. Traces: a—pUbi Er+2.5 mM isomaltulose, b—pUbi Er, c—pUbi 14S, d—2.5 mM sucrose and isomaltulose standards, e—pUbi 68J, f—pUbi 68J+2.5 mM isomaltulose.

Sugarcane Transgenic Callus with 68J Sucrose Isomerase also Showed the Highest Conversion Ratio Among the Tested Sucrose Isomerase Gene Constructs Isomaltulose could be found in the cell extracts of transgenic sugarcane callus expressing the sucrose isomerase genes. Three out of three tested 68J transgenic lines showed the isomaltulose peak higher than the sucrose peak on the CE electrograph (FIG. 8A). In contrast, three out of seven tested 14S transgenic lines showed the isomaltulose peak lower than the sucrose peak (FIG. 8B). Isomaltulose could not be detected in the calli of the other four tested 14S transgenic lines. The transgenic callus with the *Erwinia rhapontici* gene showed even lower isomaltulose levels than the 14S lines (FIG. 8C).

These results show for the first time the feasibility of production of isomaltulose by expression of sucrose isomerase in plants, and the high potential of sucrose isomerase 68J for this purpose.

Example 20

Further Characterisation of Strain 68J

Figure 9:
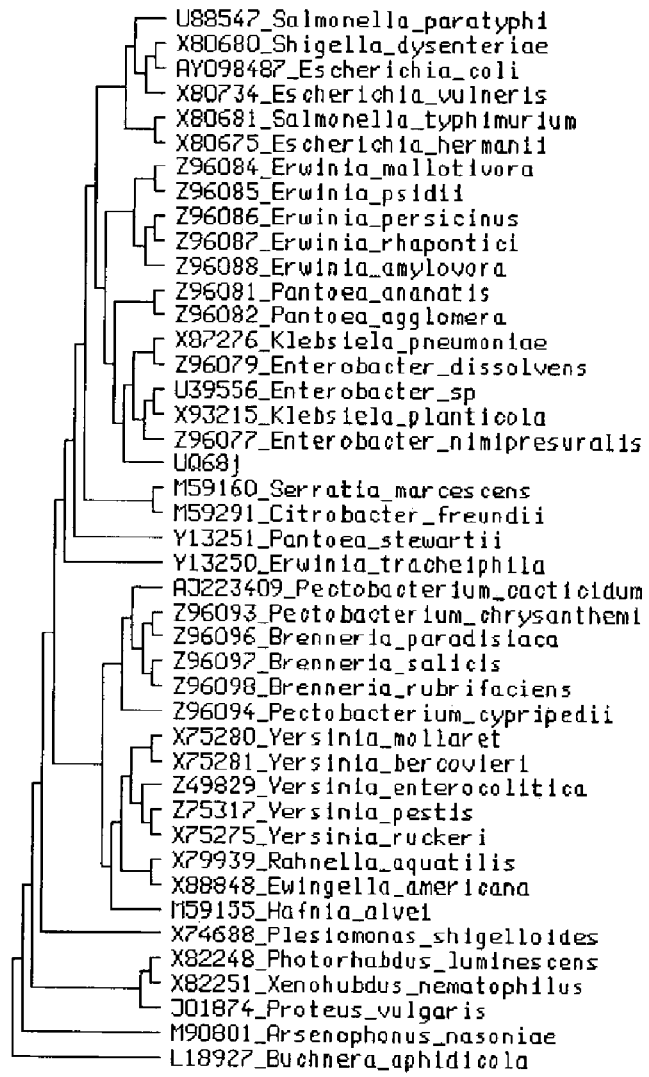
FIG. 9 is a cladogram showing the position of 68J among the Enterobacteriaceae using the unweighted pair group method with arithmetic averages (UPGMA), based on 16S rDNA sequences.

The full length 16S rDNA of 1502 bases from strain 68J was sequenced (GenBank accession AY227805) and found to cluster (at 95.1% to 97.8% identity) with sequences from *Klebsiella, Enterobacter, Erwinia,* and *Pantoea* species (FIG. 9).

68J colonies were unpigmented. Cells grown for 12–18 hour in LB medium at 30° C. were non-capsulate, motile, straight rods with round ends, Gram negative, and 0.60–0.80×1.5–2.5 µm in size. The strain was facultatively anaerobic, produced acid from glucose, and showed optimal growth at 30° C. with poor growth at 10° C. and 37° C. It was positive in catalase and Voges-Proskauer tests; weakly positive in indole, methyl red and Simon's citrate tests; and negative for oxidase, urea hydrolysis, lysine decarboxylase, ornithine decarboxylase, malonate utilisation, and gelatin liquefaction. Based on these results and the pattern of carbon source utilisation (Table 4), 68J most closely matched the characteristics of *Pantoea dispersa* (Holt et al. 1994).

Methods

Sequencing of 16S rDNA and Phylogenetic Analysis

Total genomic DNA was extracted by the method of Priefer et al. (1984). The hooked DNA was dissolved in TE buffer at 4° C. for 2 days without shaking. Primers designed to amplify the complete 16S rDNA based on highly conserved regions are forward: 5'-AGA GTT TGA TCC TGG CTC AG-3' (SEQ ID NO: 50) and reverse: 5'-GGT TAC CTT GTT ACG ACT T-3' (SEQ ID NO: 51). PCR was conducted under routine conditions using pfu DNA polymerase (Strategene). The PCR products were cloned into TA-Cloning vector PCR2.1 (Invitrogen) following the manufacturer's instructions. The cloned 16S rDNA plasmid insert was sequenced at the Australian Genome Research Facility, using the ABI PRISM Big Dye Reaction Kit. For

TABLE 4

Growth of strain 68J with different carbon sources (relative values).

| Carbon source | Growth | Carbon source | Growth | Carbon source | Growth |
|---|---|---|---|---|---|
| Water | 0 | Turanose | 23 | D-alanine | 7 |
| α-cyclodextrin | 9 | Xylitol | −12 | L-alanine | 188 |
| Dextrin | 77 | Methyl pyruvate | 379 | L-alanyl-glycine | 64 |
| Glycogen | 38 | Mono-methyl succinate | 10 | L-asparagine | 423 |
| Tween40 | 25 | Acetic acid | 83 | L-aspartic acid | 201 |
| Tween80 | 37 | cis-aconitic acid | 122 | L-glutamic acid | 405 |
| N-acetyl-D-galactosamine | −4 | Citric acid | 66 | Glycyl-L-aspatic acid | −8 |
| N-acetyl-D-glucosamine | 592 | Formic acid | 155 | Glycyl-L-glutamic acid | 2 |
| Adonitol | −2 | D-galactonic acid lactone | −7 | L-histidine | −6 |
| L-arabinose | 605 | D-galacturonic acid | −1 | Hydroxy L-proline | −9 |
| D-arabitol | −11 | D-gluconic acid | 718 | L-leucine | −9 |
| Cellobiose | −8 | D-glucosaminic acid | 1 | L-ornithine | −8 |
| i-erythritol | 0 | D-glucoronic acid | 6 | L-phenylalanine | −2 |
| D-fructose | 616 | α-hydroxy butyric acid | 36 | L-proline | 200 |
| L-fucose | 3 | β-hydroxy butyric acid | −5 | L-pyroglutamic acid | −2 |
| D-galactose | 85 | γ-hydroxy butyric acid | −4 | D-serine | −3 |
| gentiobiose | 641 | ρ-hydroxy phenylacetic acid | 5 | L-serine | 332 |
| α-D-glucose | 627 | Itaconic acid | −4 | L-theronine | −12 |
| m-inositol | 611 | α-keto butyric acid | 2 | D,L-carnitine | −10 |
| α-lactose | 14 | α-keto glutaric acid | 91 | γ-amino butyric acid | −16 |
| α-D-lactose lactulose | 12 | α-keto valeric acid | −4 | Urocanic acid | −4 |
| Maltose | 127 | D,L-lactic acid | 365 | Inosine | 281 |
| D-mannitol | −1 | Malonic acid | −2 | Uridine | 43 |
| D-mannose | 49 | Propionic acid | 10 | Thymidine | −4 |
| D-melibiose | 6 | Quinic acid | 203 | Phenylethylamine | 6 |
| β-methyl D-glucosidase | 684 | D-saccharic acid | 0 | Putrescine | 2 |
| Psicose | 180 | Sebacic acid | −7 | 2-amino ethanol | −4 |
| D-raffinose | 330 | Succinic acid | 100 | 2,3-butynediol | 1 |
| L-rhamnose | 5 | Bromo succinic acid | −12 | Glycerol | 585 |
| D-sorbitol | −3 | Succinamic acid | −10 | D,L-α-glycerol phosphate | −8 |
| Sucrose | 739 | Glucuronamide | −10 | Glucose-1-phosphate | 356 |
| D-trehalose | 619 | Alaninamide | 30 | Glucose-6-phosphate | 98 | the first round sequencing, universal primers (M13 Reverse and M13 Forward) for PCR2.1 vector were used, then custom primers were used for sequence extension. Sequences were conducted and confirmed from both strands of the DNA.

The EMBL and GenBank database accessions used by Hauben et al. (1998) and by Sutra et al. (2001), were employed to represent the Enterobacteriaceae family. Data analyses were conducted by using software on WebANGIS-GCG. Nucleotide sequences were compared by method GAP, multiple alignments were conducted by method PileUp, sequence distance matrix was generated by the method of Jukes and Cantor, cluster analysis and cladogram tree was conducted using the unweighted pair group method with arithmetic averages (UPGMA).

Phenotypic Tests for Taxonomic Identification of Strain 68J

The morphological, cultural and biochemical features of strain 68J were determined in tests using *E. coli* (Top10), *K. oxytoca* (JMP4505), *E. rhapontici* (WAC2928) as positive/negative controls. Gram stain, fermentation, catalase activity, pigment observation, and Simon's citrate tests were conducted according to Singleton (1999, Bacteria in Biology, Biotechnology and Medicine (5$^{th}$ edition). Wiley, New York). Oxidase activity by Kovac's reagent, indole production by Ehrlich's indole test, methyl red response, Voges-Proskauer reaction in Clark and Lub's medium, urea hydrolysis in Christensen's urea, lysine decarboxylase, ornithine decarboxylase and gelatin liquefaction were tested as described by MacFaddin (1979, Biochemical Tests for Identification of Medical Bacteria. Williams & Wilkins, Baltimore). Morphology, capsules and motility were observed microscopically. Carbon source utilization was tested in 96-well plates (BIOLOG GN).

Example 21

Effects of Culture Conditions on 68J Growth and Isomaltulose Production

68J Cells Grown in Rich Medium Converted Sucrose into Isomaltulose Very Efficiently.

Harvested cells or filtrates from 18 h cultures were normalised for $OD_{600}$ of the sampled culture as a measure of the number of cells, and tested for SI activity. From SLB medium, *P. dispersa* 68J cells showed 35-fold higher rate of isomaltulose production than *E. rhapontici* WAC2928 cells. Conversion of sucrose was complete within 1 h for 68J (FIG. 10A), but reached a plateau with 20% residual sucrose after more than 40 h for WAC2928 (FIG. 10B).

Figure 10:
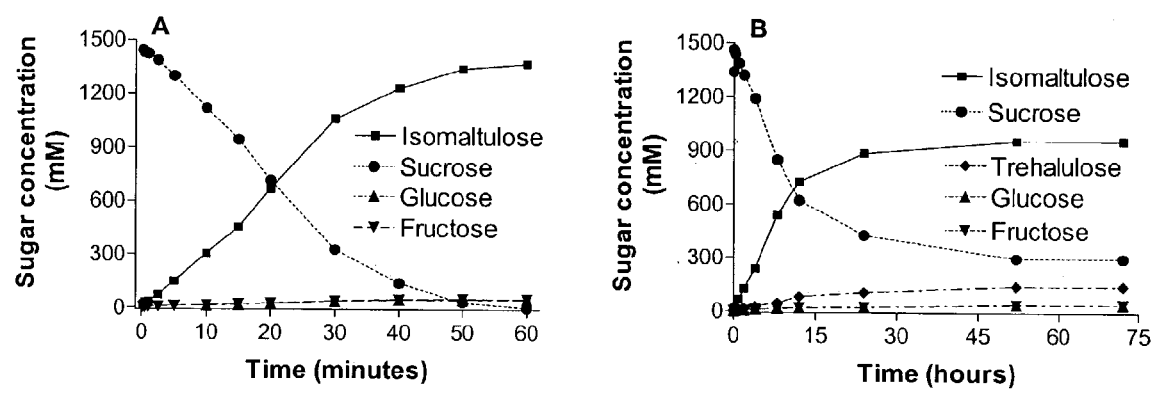
FIG. 10 is a graphical representation showing a time course of sucrose conversion by *P. dispersa* 68J (A) and *E. rhapontici* WAC2928 (B) cells. The cells were grown in LB medium supplemented with 4% sucrose at 30° C. for 18 hours with 225 rpm shaking. Reactions were conducted by suspending cells (harvested from the equivalent of 1.0 mL of culture at $OD_{600}$=1.50) in citrate/phosphate buffered (pH 6.0) 50% (w/v) sucrose at 37° C. Note the different incubation times.

Isomaltulose was the sole isomer detected from 68J, accounting for 94% of the supplied sucrose. In contrast, WAC2928 ultimately produced substantial trehalulose (8–10%) with a reduced yield of isomaltulose (62–65%), and much lower yields within the routine 4 h assay period (FIG. 10, Table 5). For both organisms, SI activity was largely contained in the cells, with less than 3.5% in the culture filtrate. When cells were grown in SBP medium (lacking yeast extract) rather than SLB medium, SI activity dropped by more than 99% for 68J, and by 35% for WAC2928.

TABLE 5

Comparison of SI activity in *P. dispersa* 68J and *E. rhapontici* WAC2928 cells grown in LB or BP media with 4% sucrose.

| Enzyme source | Strain | Initial SI activity U mL$^{-1}$ (OD$_{600}$)$^{-1}$ | Percent sucrose converted within 4 h to | | | | |
|---|---|---|---|---|---|---|---|
| | | | IM | TH | Gluc | Fruc | Suc |
| Cells from SLB culture | 68J | 8.48 | 93.7 | 0 | 3.1 | 3.2 | 0 |
| | WAC2928 | 0.23 | 16.4 | 0.8 | 0.2 | 0.2 | 81.2 |
| Filtrate from SLB culture | 68J | 0.29 | 2.0 | 0 | 1.5 | 1.5 | 94.9 |
| | WAC2928 | 0 | 0 | 0 | 0 | 0 | 100 |
| Cells from SBP culture | 68J | 0.03 | 1.9 | 0 | 2.6 | 0.7 | 94.8 |
| | WAC2928 | 0.15 | 10.6 | 1.1 | 1.0 | 1.1 | 86.1 |

IM: isomaltulose, TH: trehalulose, Suc: sucrose, Gluc: glucose, Fruc: fructose.
Activity of 68J cells in the SI assay was independent of the sugar in the medium used for cell growth.

Figure 11:
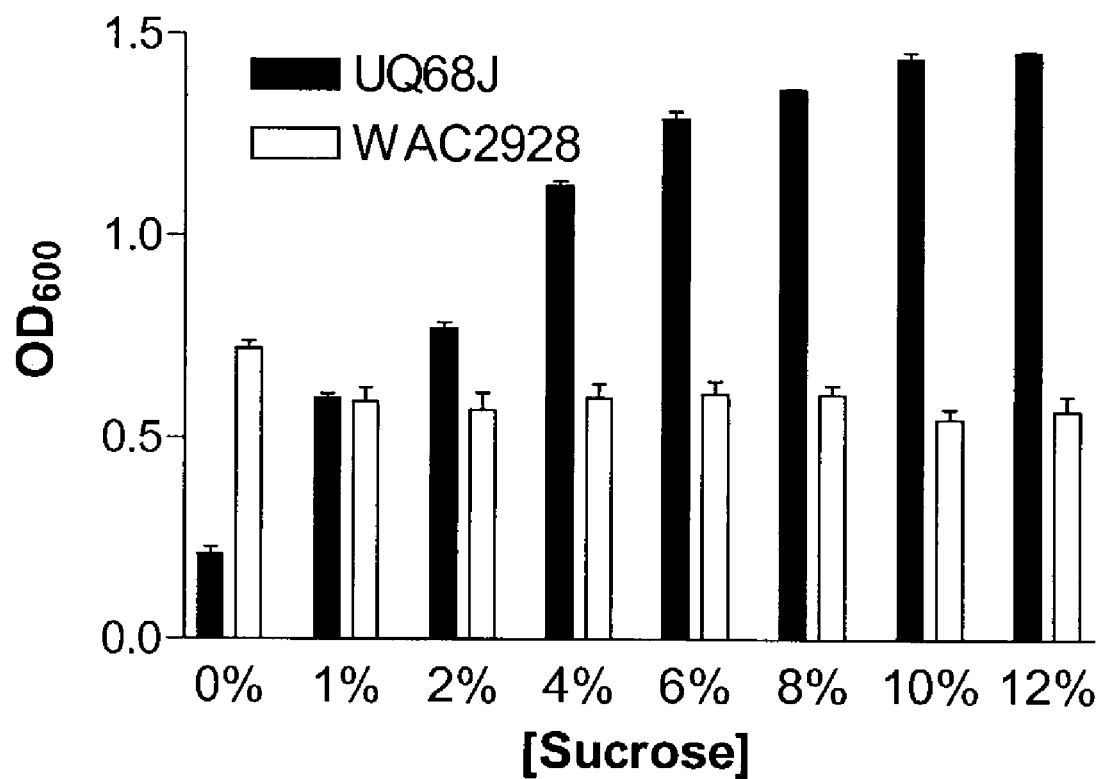
FIG. 11 is a graphical representation showing the effects of sucrose concentration in BP medium on growth of *P. dispersa* 68J and *E. rhapontici* WAC2928. Bars are means with standard errors from three replicates.

SI activity was not significantly different for *P. dispersa* 68J cells grown in BP medium with or without different sugars (Table 6). In contrast, SI activity in *E. rhapontici* WAC2928 cells was highest after growth with fructose, followed by sucrose or isomaltulose; cells grown with glucose, lactose and maltose showed low activity, and cells grown in the medium without sugar showed no detectable activity. There was a positive correlation between SI activity and sucrose concentration in the growth medium for WAC2928, but not for 68J (Table 6). This effect did not parallel the effect on growth rate, which was enhanced by increased sucrose for 68J, but not WAC2928 (FIG. 11). Thus SI activity is inducible by some sugars including sucrose in WAC2928, whereas 68J shows strong constitutive activity. This is likely to be advantageous in allowing a wider choice of growth feedstocks for commercial SI production by 68J.

TABLE 6

Effects of different sugars or sucrose concentrations in BP growth medium on SI activity in harvested cells of *P. dispersa* 68J and *E. rhapontici* WAC2928.

| Sugar | Specific activity mU mL$^{-1}$ (OD$_{600}$)$^{-1}$ | |
|---|---|---|
| (2%, w/v) | 68J | WAC2928 |
| None | 29 ± 3 | 0 |
| Glucose | 28 ± 2 | 8 ± 2 |
| Fructose | 30 ± 3 | 251 ± 17 |
| Sucrose | 28 ± 2 | 125 ± 18 |
| IM | 29 ± 3 | 107 ± 7 |
| Lactose | 27 ± 3 | 11 ± 3 |
| Maltose | 30 ± 3 | 39 ± 5 |

TABLE 6-continued

Effects of different sugars or sucrose concentrations in BP growth medium on SI activity in harvested cells of *P. dispersa* 68J and *E. rhapontici* WAC2928.

| [Sucrose] | Specific activity mU mL$^{-1}$ (OD$_{600}$)$^{-1}$ | |
|---|---|---|
| | 68J | WAC2928 |
| 0% | 29 ± 3 | 0 |
| 1% | 27 ± 3 | 119 ± 13 |
| 2% | 29 ± 3 | 151 ± 23 |
| 4% | 32 ± 3 | 154 ± 25 |
| 6% | 31 ± 3 | 165 ± 27 |
| 8% | 29 ± 3 | 192 ± 32 |
| 10% | 31 ± 2 | 374 ± 31 |
| 12% | 30 ± 2 | 401 ± 36 |

68J did not use isomaltulose for enhanced growth in basal peptone medium.

Figure 12:
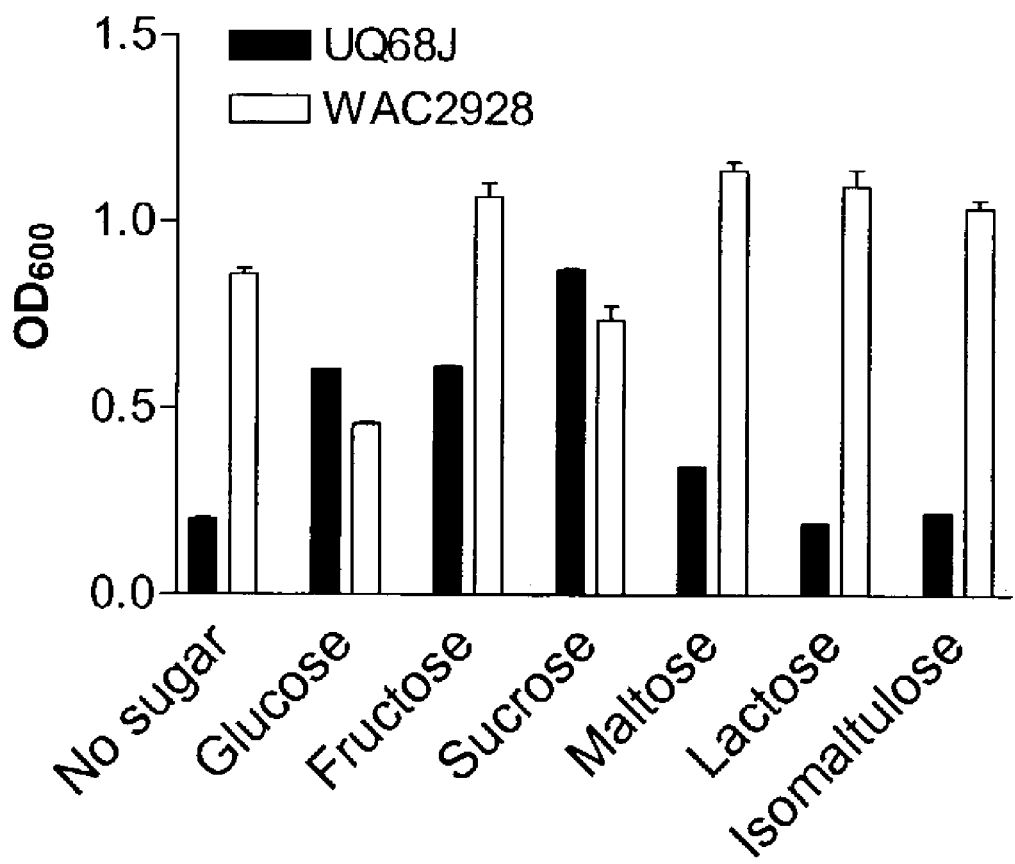
FIG. 12 is a graphical representation showing the effects of different sugars (2% w/v) in BP medium on growth of *P. dispersa* 68J and *E. rhapontici* WAC2928. Bars are means with standard errors from three replicates.

Addition to BP medium of 2% sucrose, fructose or glucose supported faster growth of *P. dispersa* 68J, whereas lactose, maltose and isomaltulose had little effect during 18 h incubation at 30° C. (FIG. 12). In contrast, isomaltulose substantially enhanced growth by *E. rhapontici* WAC2928. Lesser tendency to use isomaltulose for growth may reflect lower isomaltulase activity, and is likely to be advantageous for commercial isomaltulose production by 68J.

Methods

Growth and Isomaltulose-Forming Activity

Isomaltulose production was tested using cells grown in LB and in a basal peptone medium (BP, comprising 1% BBL gelysate peptone and 0.5% NaCl, adjusted to pH 7.0 prior to autoclaving). Glucose, fructose, sucrose, lactose, maltose or isomaltulose was added to the cooled media, from a filter-sterilised stock. The media containing 4% (w/v) sucrose are referred to as SLB and SBP respectively.

Inoculum of 100 μL from a culture grown for 12 h in LB medium was added to 25 mL growth medium in a 250 mL flask. After 18 h at 30° C. on a shaker at 225 rpm, OD$_{600}$ was used to measure growth. Cultures were diluted with growth medium to OD$_{600}$=1.50 (approximately half the cell density of a saturated culture in SLB). Aliquots of 1 mL were harvested by centrifugation at 5000×g for 10 min and washed three times with 0.1 M citrate/phosphate buffer (pH 6.0). The cell pellets were resuspended in 0.4 mL of 0.1 M citrate/phosphate buffer (pH 6.0) containing 50% sucrose (w/v). Culture supernatant was filtered through a 0.2 μm filter (Pall Acrodisc), and 0.1 mL was mixed with 0.4 mL of 0.1 M citrate/phosphate buffer (pH 6.0) containing 50% sucrose (w/v), for parallel testing of culture filtrate and harvested cells in the SI assay.

The reaction mixtures were incubated at 37° C. with slow shaking. Aliquots were removed at specified times, and the reaction was terminated in a 100° C. water bath for 10 min. The reaction mixture was then centrifuged at 15,000×g for 20 min to remove cell debris and denatured proteins. The supernatant was collected for capillary electrophoresis as described above. Peak areas of sucrose, isomaltulose, trehalulose, glucose and fructose were quantified against corresponding standards. Since isomaltulose was the main product of enzyme reaction, the activity unit (U) was defined as the amount of enzyme that can produce 1 μmole of isomaltulose per minute at the initial stage of the reaction. Results were normalised per mL of cell culture at OD$_{600}$=1.00 (approximately 30% of the cell density of a saturated culture in SLB).

Discussion of Examples 20 and 21

Based on 16S rDNA phylogenetic analysis, utilisation of 95 tested carbon sources, and other biochemical characteristics, 68J is a member of the Enterobacteriaceae, and it most closely resembles *Pantoea dispersa* (Holt et al., 1994, Bergey's Manual of Determinative Bacteriology (9$^{th}$ Edition). Williams & Wilkins, Baltimore). Hauben et al. (1998, *Systematic and Applied Microbiology* 21: 385–397) proposed six signature regions involved in secondary structure of the 16S rRNA to differentiate the genera *Brenneria*, *Erwinia*, *Pantoea*, and *Pectobacterium*. The 16S rDNA sequence of strain 68J possessed four of the six proposed signature sequences for the genera *Pantoea* and *Erwinia*, and one for *Brenneria*. The genera *Klebsiella* and *Enterobacter* share some of the signature regions of *Erwinia* and some of *Pantoea*, and it is likely that these signatures can be mixed through horizontal gene transfer and recombination (Yap et al., 1999, *Journal of Bacteriology* 181: 5201–5209).

68J cells harvested from LB medium converted 94% of sucrose into isomaltulose and 6% into glucose and fructose. Other characterised isomaltulose-producing bacteria also produce trehalulose (α-D-glucosyl-1,1-D-fructose) when incubated (as intact, disrupted or immobilized cells) with sucrose (Table 7). *P. rubrum* (Tsuyuki et al., 1992), *E. rhapontici* NCPPB 1578 (Cheetham, 1982, supra), *E. carotovora* var *atroseptica* (Lund and Waytt, 1973, supra), *S. plymuthica* NCIB 8285 (Fujii et al., 1983, *Nippon Shokuhin Kogyo Gakkishi* 30: 339–344), and *K. planticola* CCRC 19112 (Huang et al., 1998, *Journal of Industrial Microbiology & Biotechnology* 21: 22–27) yielded 75–86% isomaltulose and 7–25% trehalulose. Several strains of *Klebsiella* were reported to produce 60–70% isomaltulose and 25–30% trehalulose (Tsuyuki et al., 1992, *Journal of General and Applied Microbiology* 38: 483–490). *P. mesoacidophila* MX-45 (Miyata et al., 1992, supra) and *A. radiobacter* MX232 (Nagai-Miyata et al., 1993, supra) generated more trehalulose (90%) than isomaltulose. Careful analysis of products from immobilized cells or purified SI enzyme from a strain of *S. plymuthica* revealed low yields of glucose, fructose, isomaltose, isomelezitose and trehalulose in addition to isomaltulose (Fujii et al., 1983, supra; Véronèse and Perlot, 1999, supra). Most reports focus on the relative yields of sucrose isomers, and do not quantify the low yields of monosaccharides.

Caution is required in comparisons between published results of cellular sucrose isomerase activities, because they have been obtained under varied conditions including different cell cultivation media, treatments to harvested cells, reaction media, temperatures, assay durations, and analytical procedures (Table 7). Some of these conditions are now known to affect the relative yields of different products (Véronèse et al. 1999, *Biotechnology Techniques* 13: 43–48.; Vér and Perlot, 1999, supra). Nevertheless, the specificity of *P. dispersa* 68J cells for the production of isomaltulose from sucrose appears to be exceptional. Product specificity is a useful feature for industrial production of isomaltulose.

TABLE 7

Sugar compositions of products on molar basis and sucrose isomerase activities of cells from different bacterial strains. A., Agrobacterium; E., Erwinia; K, Klebsiela; P., Protaminobacter; Ps., Pseudomonus; S., Serratia.

| Species | IM (%) | TH (%) | Gluc (%) | Fruc (%) | Suc (%) | Activity (U mL$^{-1}$) | Reference |
|---|---|---|---|---|---|---|---|
| P. dispersa 68J | 93.7 | 0 | 3.1 | 3.2 | 0 | 28.3 | This study[1] |
| E. rhapontici WAC2928 | 62.3 | 8.2 | 5.1 | 4.9 | 20.1 | 0.8 | This study[2] |
| K. planticola MX-10 | 63.9 | 30.2 | — | — | 5.9 | 4.3 | Tsuyuki et al.[3], 1992 |
| K. planticola CCRC19112 | 76–84 | 14–16 | 2–6 | 2–6 | — | 8.4 | Huang et al.[4], 1998 |
| S. plymuthica ATCC15928** | 72.6 | 6.6 | 10.1 | 10.1 | — | — | Véronèse and Perlot, 1999** |
| Ps. mesoacidophila MX-45 | 9.2 | 88.4 | — | — | 2.4 | — | Miyata et al.[5], 1992 |
| A. radiobacter MX-232 | 9.9 | 88.8 | — | — | 1.4 | — | Nagai-Miyata et al.[6], 1993 |
| K. planticola MX-10* | 65.4 | 29.7 | — | — | 2.2 | 40.7* | Tsuyuki et al.[3], 1992 |
| P. rubrum CBS574.77* | 85.7 | 8.7 | — | — | 1.1 | 30.0* | Tsuyuki et al.[3], 1992 |

IM: isomaltulose, TH: trehalulose, Suc: sucrose, Gluc: glucose, Fruc: fructose.
*immobilised cells (cell density not specified); other activities are per mL of saturated bacterial culture.
**purified enzyme.
—not specified.
[1]Cultivation: LB + 4% sucrose, 18 h at 30° C.; Reaction: cells from 1 mL culture, with 0.4 mL 50% sucrose in 0.1 M citrate phosphate buffer pH 6.0 at 37° C. for 1 h.
[2]Cultivation: LB + 4% sucrose, 18 h at 30° C.; Reaction: cells from 1 mL culture, with 0.4 mL 50% sucrose in 0.1 M citrate phosphate buffer pH 6.0 at 37° C. for 48 h.
[3]Cultivation: 1.0% peptone, 0.5% yeast extract, 0.3% meat extract, 0.3% NaCl, 10% sucrose, 0.2% Na$_2$HPO$_4$.12H$_2$O pH 7.0, 24 h at 37° C.; Reaction: cells from 1 mL culture, with 25% sucrose in calcium acetate buffer pH 5.6 at 20° C. for 1 h.
[4]Cultivation: 3.0% soy broth, 2% Bacto-tryptone, 0.5% NaCl, 7% sucrose, pH 7.0, 18 h at 30° C.; Reaction: cells from 1 mL culture, with 60% sucrose in 0.1 M acetate buffer pH 5.0 at 40° C. for 4 h.
[5]Cultivation: 1.0% peptone, 0.5% yeast extract, 0.3% meat extract, 0.3% NaCl, 10% sucrose, 0.2% Na$_2$HPO$_4$.12H$_2$O pH 7.0, 24–48 h at 28° C.; Reaction: cells from 1 mL culture, with 25% sucrose in calcium acetate buffer pH 5.6 at 20° C. for 1 h.
[6]Cultivation: 1.0% peptone, 0.5% yeast extract, 0.3% meat extract, 0.3% NaCl, 10% molasses, 0.2% Na$_2$HPO$_4$.12H$_2$O pH 7.0, 24–48 h at 28° C.; Reaction: cells from 1 mL culture, with 25% sucrose in calcium acetate buffer pH 5.6 at 20° C. for 1 h.

A high rate of conversion of sucrose into isomaltulose, and a low residual sucrose level are also important for industrial conversion, and P. dispersa 68J appears excellent in comparison to published results for other bacteria in these characteristics (Table 7). In other strains, SI activity in harvested cells commonly depends on sugar content of the growth medium (Huang et al., 1998), as shown here for E. rhapontici WAC2928. In contrast, growth of 68J can be stimulated by sugars including sucrose and fructose to increase harvestable cell density, but SI activity per cell is unaffected (Table 6, FIGS. 11-12). This constitutive synthesis of SI is an advantage, as it is likely to allow a greater choice of substrates for cell growth, and to confer greater stability of SI activity during the culture cycle to provide bacterial cells for industry. It will be advantageous to ensure a supply of the growth factors present in yeast extract that are needed for high SI activity in P. dispersa 68J (Table 5).

The evolutionary advantage for SI activity in microbes is believed to be a capacity to convert temporary surpluses of available sucrose into an isomeric form that can subsequently be utilised selectively by the isomer producer (Börnke et al., 2001, Journal of Bacteriology 183: 2425-2430). Consistent with this interpretation, most naturally-occurring strains that synthesise isomaltulose are also able to utilise it as a carbon source, a property that is not advantageous for efficient industrial production of isomaltulose. For example, there has been interest in engineering cells for industrial use with reduced activity of isomaltulase, the hydrolase able to cleave isomaltulose into monosaccharides for cell growth (Mattes et al., 1998, supra). P. dispersa 68J can use isomaltulose as a carbon source, but in contrast with E. rhapontici WAC2928 addition of isomaltulose to the basal growth medium had little effect on growth during 18 h incubation (FIG. 11). This most likely indicates that isomaltulase activity is tightly repressed in 68J, another advantage in an organism grown for use in commercial isomaltulose production.

Example 22

Phylogenetic Analysis of Sucrose Isomerases

Figure 13:
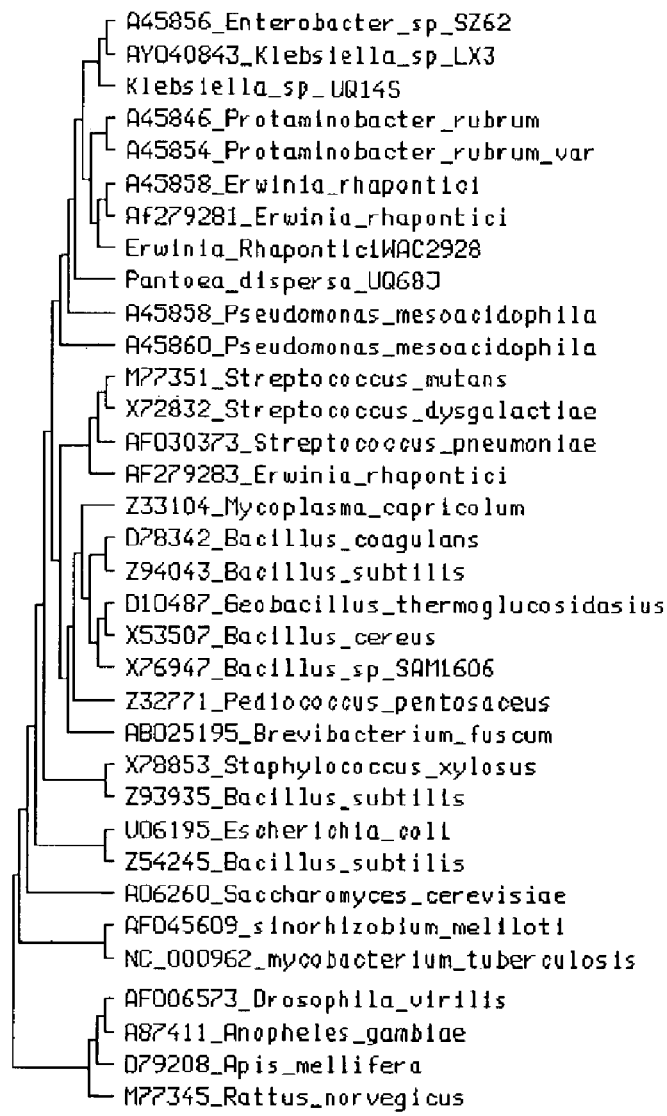
FIG. 13 is a graphical representation showing the relationships among SIs and representative glucosidases revealed using the unweighted pair group method with arithmetic averages and Kimura's method for sequence distance matrix. The dotted line separates SIs (above) from hydrolases.

In phylogenetic analysis of amino acid sequences among representative hydrolases, glucosidases and sucrose isomerases, the cloned SIs from E. rhapontici WAC2928 and Klebsiella sp. 14S fell in a cluster with other known sucrose isomerases. The novel SI from P. dispersa 68J diverged earlier from this cluster, along with the SI and hydrolase genes from trehalulose-producing P. mesoacidophila, and various glucosidases (FIG. 13). SI genes and glucosidases share conserved domains for sugar binding. As a result, conserved sequences and primers described by Mattes et al. (1998, supra) are not specific for SIs. In Table 8, there are provided several sequences conserved among SIs but not present in glucosidases.

TABLE 8

Conserved elements specific for sucrose isomerases.

| Peptide | | Corresponding Oligonucleotide | |
|---|---|---|---|
| Sites | Amino acids | Sites | Nucleotides |
| 321–327 | DLIRLDR [SEQ ID NO:40] | 961–981 | ga(c/t) (c/t)t(g/c/a) at(t/c) (c/a)g(t/a/g) (t/c)(a/t)(t/c) gat cg(c/t/a) [SEQ ID NO:41] |
| 427–436 | EVKGFWXDYV [SEQ ID NO:42] | 1279–1318 | gag gt(c/g/t) aaa gg(t/c) tt(t/c) tgg (c/a)a(g/a/t/c) ga(t/c) ta(t/c) [SEQ ID NO:43] |
| 380–385 | (R/S)PQWRE [SEQ ID NO:44] | 1138–1155 | (a/c)g(g/c/a) cc(g/a) caa tgg (c/g)(c/g)(g/c/t) ga(g/a) [SEQ ID NO:45] |
| 178–191 | PNNYPSFFGGSAW [SEQ ID NO:46] | 532–570 | cc(a/t/c) aa(t/c) aa(t/c) ta(t/c) cc(t/c) tc(a/c/t) tt(t/c) tt(t/c) gg(t/c) gg(t/c) tc(a/g) gc(a/c/g) tgg [SEQ ID NO:47] |
| 198–213 | QYYLHYF(A/G)XQQPDLN W [SEQ ID NO 48] | 592–561 | ca(a/g) ta(t/c) ta(t/c) (t/c)t(a/g) ca(t/c) ta(t/c) tt(t/c) g(g/c)(t/c) (a/c)(a/g/c)(t/a) cag [SEQ ID NO:49] |

Example 23

Figure 14:
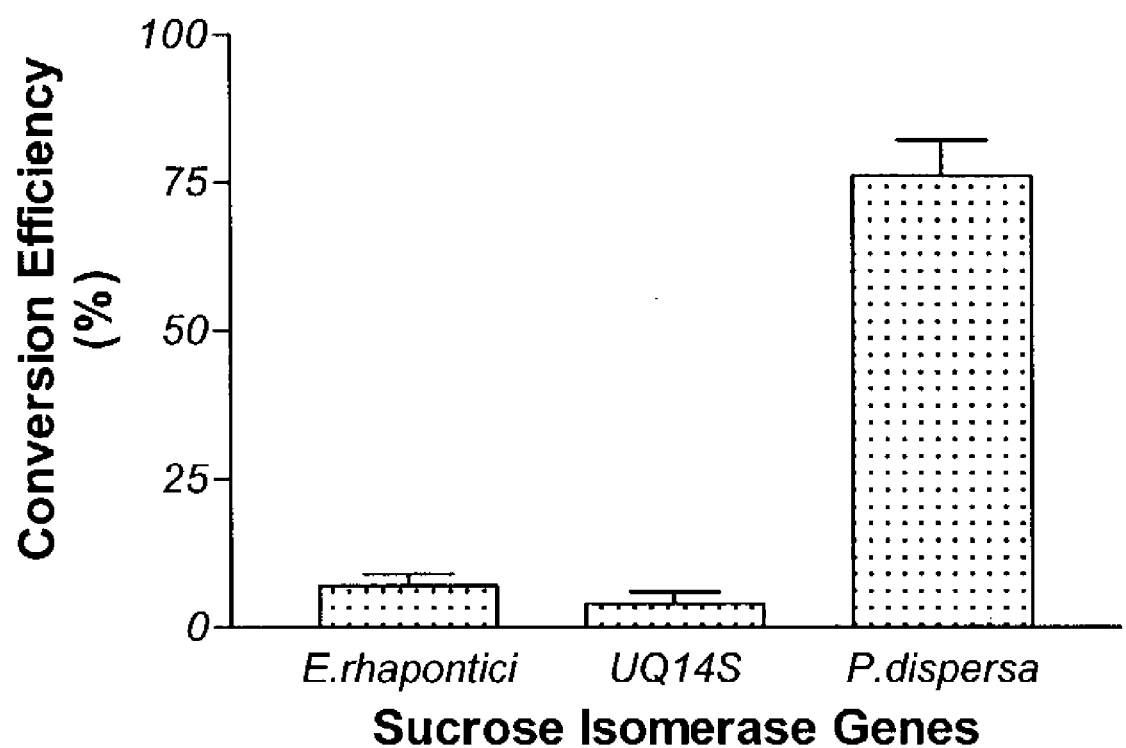
FIG. 14 is a graphical representation showing SI conversion efficiencies of *E. coli* cells expressing different SI genes. Conversion efficiency=[isomaltulose]/[sucrose provided]. Bars show means with standard errors from 3 replicates. The experiment was performed three times with similar outcomes.

SI from *P. dispersa* Showed the Highest Conversion Efficiency Among the Tested Isomerases Expressed in *E. coli* Cells When the SI genes from *E. rhapontici*, *Klebsiella* sp. and *P. dispersa* were arranged for expression using the same promoter, start codon context and termination sequences in vector pET24b, there was no significant difference in total protein content, or in expressed SI content at around 10% of total protein (Table 9). However, the conversion efficiency from sucrose to isomaltulose by *E. coli* expressing the cloned *P. dispersa* gene was 10 times that of the clone from *E. rhapontici* and 18 times that of the clone from *Klebsiella* sp. (FIG. 14). This is explained by substantial differences in soluble SI contents (estimated by recovery of the His-tagged protein), and particularly in apparent SI enzyme efficiencies in the intact cell assay. Under these conditions, the soluble Pantoea enzyme is estimated at 6–38 times the efficiency of the *Erwinia* and *Klebsiella* enzymes (Table 9).

In addition, the cells expressing *P. dispersa* SI generated smaller proportions of glucose and fructose in the SI assay than cells expressing *Klebsiella* sp. or *E. rhapontici* Sis. These results indicate high potential of the cloned SI from *P. dispersa* 68J in industrial applications for isomaltulose production.

The conversion efficiencies by cells of *E. coli* expressing the cloned SI genes, were lower than the efficiencies from cells of the corresponding native SI-producing strains in the same assay. In the current work, the cloned sequences encode the mature SI enzymes, without the leader sequences involved in transport to the periplasmic space. The overexpressed cytosolic recombinant SIs may not be in a fully soluble form or active conformation, and the cytosolic location may impose additional barriers to diffusion of the substrate during the assay. For industrial applications with intact cells, the periplasmic form of the enzyme may be preferable, and for applications with purified enzyme the clones encoding the mature enzyme are likely to be preferable.

TABLE 9

Total protein contents and estimated SI protein contents in *E. coli* cells expressing SI genes cloned from *E. rhapontici*, *Klebsiella* sp. or *P. dispersa*.

| SI gene source | Total protein (% dry wt) | Total SI* (% cellular proteins) | Soluble His-tagged SI | | Isomaltulose produced[†] (µMoles) = B | SI efficiency (Moles IM/g soluble SI) = B/A |
|---|---|---|---|---|---|---|
| | | | % Total SI | µg mL$^{-1}$[#] = A | | |
| *E. rhapontici* WAC2928 | 16.0 ± 1.6 | 10.2 ± 1.5 | 26.5 | 129.3 | 511 ± 65 | 4 |
| *Klebsiella sp.* 14S | 15.8 ± 1.4 | 9.8 ± 0.5 | 2.7 | 12.2 | 292 ± 67 | 24 |
| *P. dispersa* 68J | 16.1 ± 1.8 | 10.4 ± 1.2 | 8.1 | 36.4 | 5552 ± 212 | 152 |
| Control (pET24b) | 14.4 ± 2.0 | 0 | 0 | 0 | 0 | 0 |

Results are means ± standard errors from 3 replicates.
*Corrected for 2% proteins in the PAGE SI zone of the control crude lysates.
[#]SI recovered from batch adsorption to Ni-NTA agarose, per mL of IPTG-induced culture.
[†]Isomaltulose produced in the cellular assay, per mL of IPTG-induced culture.

Methods

Expression of SI Genes in E. coli

Fifteen cultures per construct were set up in 5 mL LB medium (Sambrook and Russell, 2001) with 50 µg/mL kanamycin in a 30 mL universal tube. Cells were grown at 37° C. at 225 rpm shaking. Six to ten cultures per construct, with $OD_{600}$=1.00 were selected for further induction. After 0.5 mL was sampled from each culture, IPTG was added to a final concentration of 0.5 mM and incubation of the cultures was continued for another 3 h at 28° C. This allowed selection of three replicate cultures per construct with the same $OD_{600}$ for sucrose conversion analysis and protein measurement. From each of the selected cultures, 1.5 mL was sampled for protein quantification, 0.5 mL for protein SDS-PAGE, and 1.0 mL for quantification of conversion efficiency from sucrose into isomaltulose. For SI protein purification experiment, the culture volume was scaled up to 25 mL in a 250 mL flask.

Assay for SI in E. coli Cells

The 1.0 mL culture sample was centrifuged at 12,000×g for 1 min, then resuspended in 5 mL of 0.1 M citrate/phosphate (pH 6.0) buffered 50% sucrose solution and incubated for 4 h at 37° C. with 225 rpm shaking. Conversion ratio was calculated from sucrose and isomaltulose peak areas normalised against standards of known concentration, using a Beckman P/ACE 5000 CE as described previously herein.

Preparation of Crude Extracts

Cells were harvested by centrifugation (3,000×g, 4° C., 10 min), resuspended in 50 mM Tris-HCl pH 8.0, and 2 mM EDTA, then re-centrifuged. The cell pellet was immediately frozen in liquid nitrogen and stored at −70° C. Cells were suspended in extraction buffer (20 mM Tris-HCl, pH 7.4, 200 mM NaCl, 1 mM EDTA, 1 mM azide, 10 mM β-mercaptoethanol), then lysed by sonication (9×15 s pulses at 50 watts from a Branson Sonifier 450 microprobe), centrifuged (10,000×g, 4° C., 10 min) and filtered through a 0.45 µm membrane (Gelman Acrodisc® 32 Super®).

Example 24

Purified SI Proteins Varied Greatly in Specific Activity and Stability

A maximum yield of soluble SI was obtained from E. coli strain BL2 1 (DE3) expressing SI genes in vector pET24b under the following conditions: 1) cultures grown at 37° C. to $OD_{600}$=1.0 before IPTG induction, 2) IPTG concentration of 0.5 mM for induction, 3) growth for SI production at 28° C.

After purification of His-tagged proteins on Ni-NTA agarose columns, a single band from each of the three constructs was revealed by Coomassie Blue R-250 stain after SDS-PAGE. The purified fresh enzymes from SDS-PAGE had specific activities for isomaltulose production of: E. rhapontici: 35 U mg$^{-1}$ protein, Klebsiella sp.: 95 U mg$^{-1}$ protein and P. dispersa: 632 U mg$^{-1}$ protein. The purified SI from E. rhapontici lost function during overnight storage at −20° C. in elution buffer diluted with 50% glycerol. In contrast, the purified enzymes from 14S or P. dispersa retained 100% of the fresh enzyme efficiency for isomaltulose production after 6-month storage at -20° C., or 60% after 15-day storage at room temperature in the same buffer. Because of instability, the E. rhapontici SI was not characterised further in purified form. Cheetham et al., (1984) found substantial differences between E. rhapontici strains for SI stability in immobilized cells, and the enzyme from strain NCPPB 1578 was stable in purified form (Cheetham, 1984). The partial sequence of the SI from strain NCPPB 1578 indicates high similarity to WAC2928 (Mattes et al., 1998, supra), and the different stabilities could reflect sequence differences yet to be revealed in the COOH region, use of His-tagged versus native enzyme, or the greater enzyme purity in the present study.

Methods

SI Protein Purification

The pET24b vector introduces a carboxy-terminal 6×His tag on expressed proteins, which were purified by adsorption to Ni-NTA agarose (Qiagen) and elution with 25 mM $NaH_2PO_4$, 150 mM NaCl, 125 mM imidazole buffer (pH 8.0) following the manufacturer's instructions. For storage, the eluted solution was diluted with 50% glycerol. The purity of SI proteins was tested by SDS-PAGE as described below. A batch procedure using Ni-NTA agarose in suspension yielded predominantly (80–95%) SI with a background of several other protein bands. A procedure using Ni-NTA agarose in adsorption columns yielded preparations containing a single protein band. Unless otherwise specified, this is the form of the purified SI enzymes used for biochemical characterisation.

For SDS-PAGE, samples were heated at 100° C. for 5 min in loading buffer (25 mM Tris-HCl, pH 6.8, 1% (w/v) SDS, 5% (v/v) β-mercaptoethanol, 10% (v/v) glycerol, 0.005% (v/v) bromophenol blue), then centrifuged at 12,000×g for 1 min. The supernatants were applied to SDS polyacrylamide gels for separation as described by Laemmli (1970). To estimate SI yield as a proportion of total cellular protein, each sample was loaded into two adjacent lanes. After running, one lane from the gel was stained in 0.025% (w/v) Coomassie Blue R-250, then destained in 30% (v/v) methanol with 10% (v/v) acetic acid. Then SI was cut from the unstained lane corresponding to the migration position in the stained gel lane. Proteins were eluted from gel slices by immersion into phosphate buffered saline (pH 7.4, Sambrook and Russell, 2001, Molecular Cloning (3$^{rd}$ Edition). Cold Spring Harbor Laboratory Press, New York) overnight at 4° C. with gentle shaking, and quantified by the Bradford (1976, *Analytical Biochemistry* 72: 248–254) method using bovine serum albumin as a standard.

Example 25

Comparison of SI Activities

Purified SI from P. dispersa Converted Sucrose Faster than that from Klebsiella sp.

For P. dispersa SI, all sucrose was converted into isomaltulose, fructose and glucose within 45 minutes (FIG. 15A). Isomaltulose accounted for 91% of the consumed sucrose, with the remainder as glucose and fructose.

Sucrose conversion by Klebsiella sp. SI was much slower, with the same enzyme concentration depleting only 76% of sucrose within 5 hours, of which 62% was converted to isomaltulose, and 14% to glucose, fructose and trehalulose.

Both of the Purified SIs Produced Isomaltulose Over a Wide Temperature Range

Figure 16:
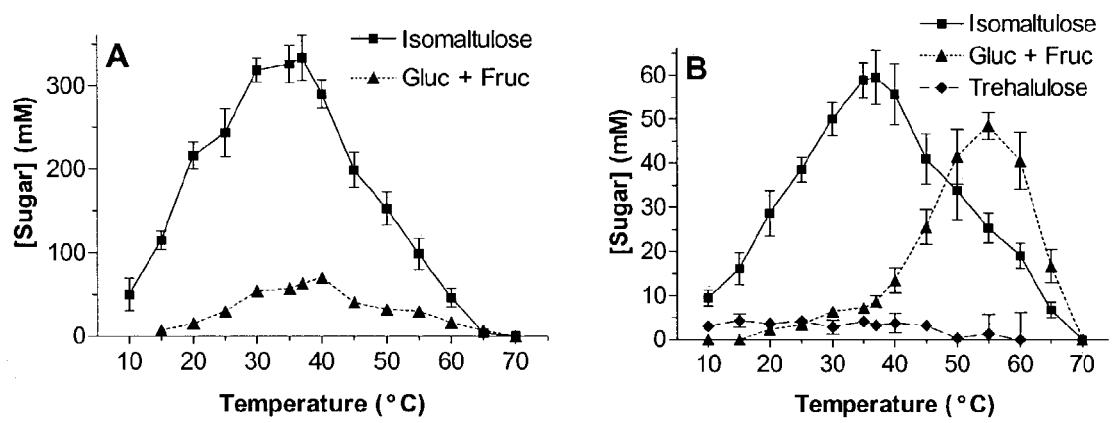
FIG. 16 is a graphical representation showing the effects of temperature on activity and product specificity of the purified SIs from *P. dispersa* 68J and *Klebsiella* sp. 14S. Note the scale difference between activity levels. Values are means±S.E. from 3 replicates.

The optimal temperature for isomaltulose production was 37° C. for the purified SIs from both P. dispersa and Klebsiella sp. (FIG. 16). At 10° C. both enzymes had 15% of their activity at optimal temperature, and both were still active at 60° C. Across the active temperature range, P. dispersa SI maintained a 10:1 molar ratio of isomaltulose to monosaccharides. In contrast, for *Klebsiella* sp. SI the molar ratio of isomaltulose : (glucose+fructose) decreased from 10:1 at 37° C. to 1:2 at 55° C., indicating a substantial shift from isomerase to invertase activity at temperatures above the optimum.

Figure 17:
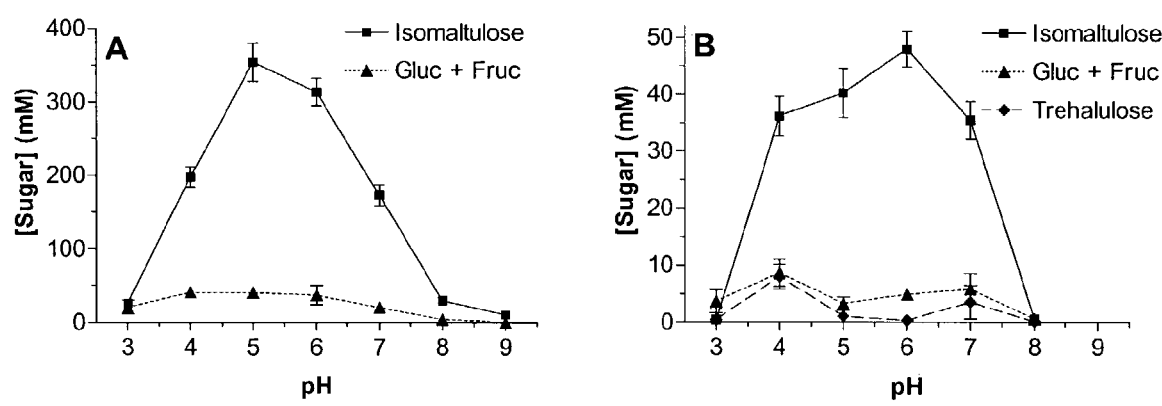
FIG. 17 is a graphical representation showing effects of pH on activity and product specificity of the purified SIs from *P. dispersa* 68J (A) and *Klebsiella* sp. 14S (B). Note the scale difference between activity levels. Values are means±S.E. from 3 replicates.

*Klebsiella* sp. SI Showed Much Higher Invertase Activity at Suboptimal pH than did *P. dispersa* SI For purified *P. dispersa* SI, pH 5 was optimal and some isomaltulose was still produced at pH 3 and 8 (FIG. 17A). Monosaccharides comprised less than 20% of the products from pH 4 to 8. For purified *Klebsiella* sp. SI, pH 6 was optimal for isomaltulose production. At pH 3 and pH 8, isomaltulose production was close to zero, and the enzyme showed predominantly invertase activity. Even at pH 4 and pH 7, the ratio of glucose+fructose to isomaltulose was larger than that for the *P. dispersa* SI (FIG. 17B).

*P. dispersa* SI had Smaller $K_m$ and Larger $V_{max}$

Figure 18:
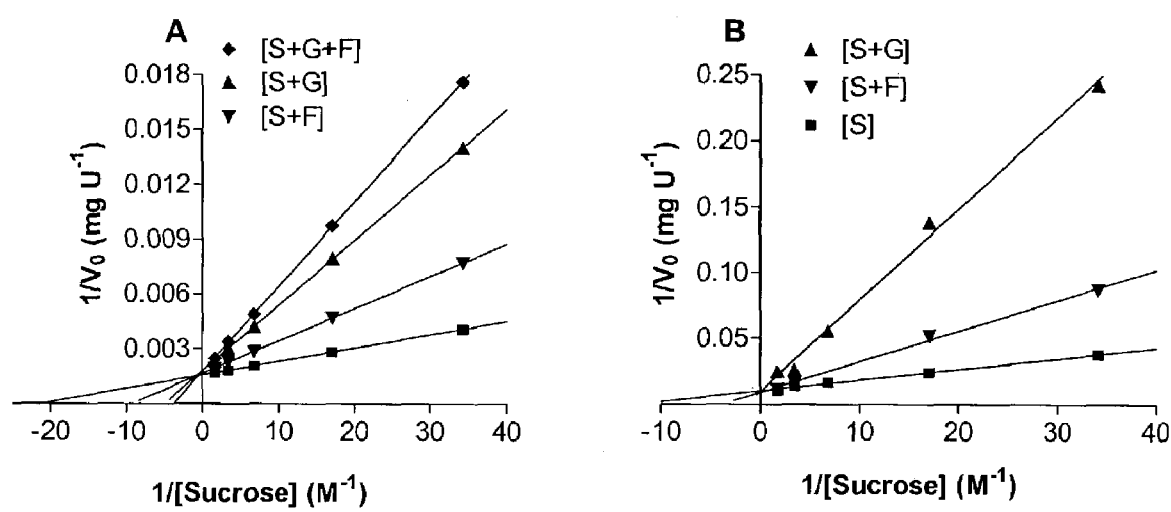
FIG. 18 is a graphical representation showing effects of glucose and fructose on the conversion rate of the purified SIs from *P. dispersa* 68J (A) or from *Klebsiella* sp. 14S (B). Lineweaver and Burk representations with: [S], sucrose only in the reaction; [S+G], designated sucrose concentration plus 277 mM glucose; [S+F], designated sucrose concentration plus 277 mM fructose; [S+G+F]; designated sucrose concentration plus 277 mM glucose and 277 mM fructose; $V_0$, initial rate.
Figure 19:
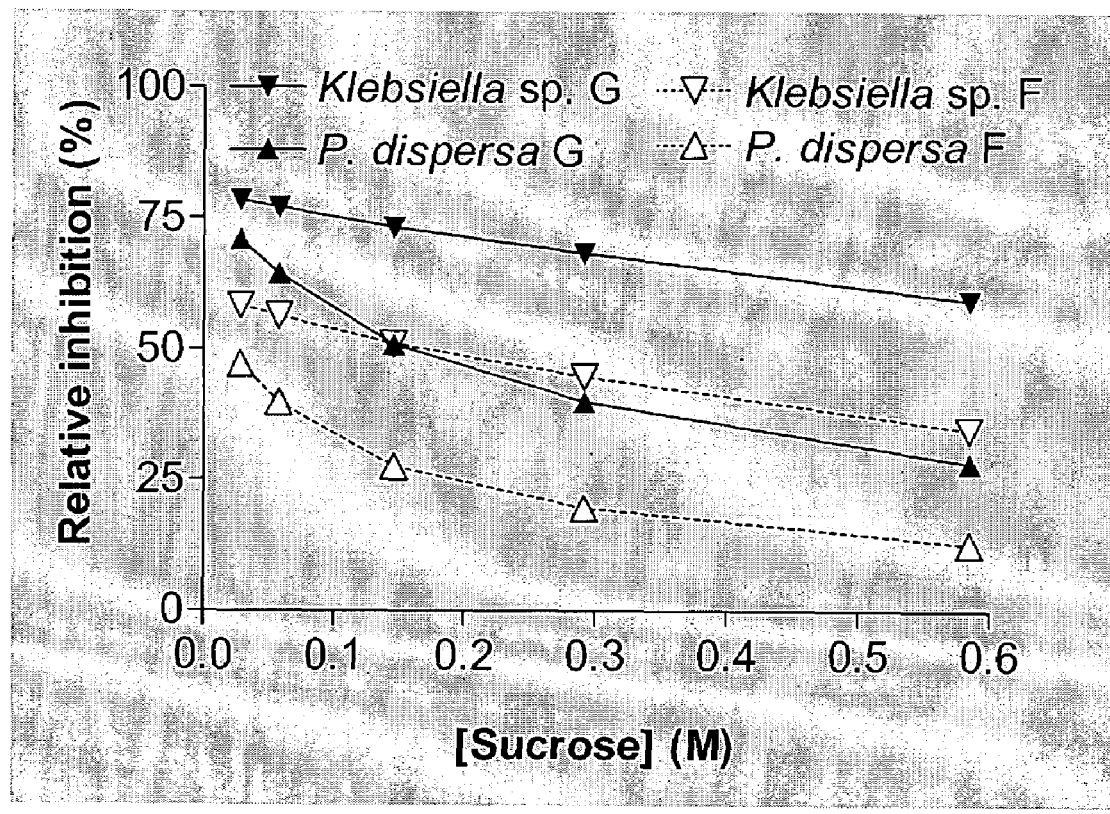
FIG. 19 is a graphical representation showing inhibition of isomaltulose production by glucose (G) and fructose (F) at various sucrose concentrations reacted with purified SI enzymes from *P. dispersa* 68J and *Klebsiella* sp. 14S. Concentration of glucose or fructose was 0.277 M.

The purified SI from *P. dispersa* had a $K_m$ value of 46.6 mM and $V_{max}$ of 636.9 U mg$^{-1}$ for isomaltulose production. In contrast, the purified SI from *Klebsiella* sp. had a $K_m$ value of 81.6 mM and $V_{max}$ of 99.8 U mg$^{-1}$ for isomaltulose production. Glucose and fructose acted as competitive inhibitors of both purified SIs (indicated by lower $K_m$ but similar $V_{max}$ in the presence of the inhibitor, FIG. 18). Glucose caused stronger inhibition than fructose, and *Klebsiella* sp. SI was more inhibited than *P. dispersa* SI, especially at higher sucrose concentrations (FIG. 19).

Glucose, but not fructose, is reported to inhibit activity of purified SIs from *E. rhapontici*, *K. plymuthica*, *P. rubrum*, and *P. mesoacidophila* (Nagai et al., 1994; Véronèse and Perlot, 1998). The different outcome for fructose in our work may arise because addition of fructose typically increases the yield of trehalulose from isomaltulose synthases (Véronèse and Perlot, 1998, supra) so an inhibition of isomaltulose formation may not be noticed if product is monitored as total reducing sugars.

SI from *P. dispersa* Neither Hydrolysed Isomaltulose Nor Produced Isomaltulose from Glucose and Fructose Isomaltulase activity of the purified enzyme was investigated by incubation with 50 mM isomaltulose at 30° C. for 30 minutes at each of pH 3.0, 4.0, 5.0, 6.0 and 7.0. Glucose and fructose were tested as substrates under the same reaction conditions. The purified SI from *P. dispersa* did not hydrolyse isomaltulose, and no product was detected after incubation of the enzyme with these monosaccharides.

Other SIs use isomaltulose as a substrate to produce trehalulose, glucose and fructose (Véronèse and Perlot 1999), and this activity can cause a gradual increase in trehalulose:isomaltulose ratio on prolonged incubation (Cheetham et al., 1982, supra). Thus mechanisms at the active site of *P. dispersa* SI may be different to those proposed by Véronèse and Perlot (1998, supra) for other SIs. Tautomerization of fructofuranose into fructopyranose is necessary for trehalulose synthesis (Kakinuma et al., 1994, *Carbohydrate Research* 264: 237–251; Véronèse and Perlot, 1998, supra). Possibilities include a higher rate constant for the EGFf to E+IM conversion (consistent with the higher $K_m$ observed for the *P. dispersa* enzyme) resulting in less opportunity for tautomerization at the active site; and a higher specificity of the transferase reaction for fructofuranose as the acceptor (consistent with the observed retention of isomaltulose product specificity at low temperatures, and in the presence of added fructose despite inhibition of isomaltulose production). Further comparisons between kinetics of the SIs from *P. dispersa* and other sources in the presence of different monosaccharides should help to elucidate these biochemical mechanisms.

Methods

Assay of Isolated SI Enzyme Activity

Enzyme activities were measured by incubating 5 µl of purified enzyme with 95 µL of sucrose solution at a final concentration of 584 mM in 0.1 M citrate/phosphate buffer (pH 6.0) at 30° C. Sugar profiles in the reaction mix were analysed at intervals by CE as described previously. One unit (U) of SI activity was defined as the amount of enzyme that could release 1 µmol of isomaltulose in one minute at the initial stage of the reaction.

Effects of pH and Temperature on SI Activity

The enzymes were incubated with sucrose at different pH ranging from 2.0 to 10.6. The solution of pH 2.0 was buffered in 0.2 M KCl; pH 3.0 to pH 9.0 were in 0.1 M citrate/phosphate buffer; pH 10.0 to pH 10.6 were in 0.2 M glycine buffer. The effect of temperature from 10° C. to 70° C. was measured at pH 6.0.

Effect of Sucrose Concentration in the Absence or Presence of Glucose and Fructose SI activity was measured by incubating the purified enzyme with different sucrose concentrations (3, 6, 15, 58, 146, 292, 584, 877, 1169 and 1461 mM) under standard assay conditions, and also with addition of glucose, fructose or both to a final concentration of 277 mM. Data were analyzed according to the method of Lineweaver and Burk (Voet and Voet, 1995) to calculate $K_m$ and $V_{max}$ values.

Discussion of Examples 22–25

Of SI genes cloned from three bacteria isolated by functional screening for SI activity, two proved very similar to known SI genes from *E. rhapontici* (Bornke et al., 2001, *Carbohydrate Research* 264: 237-supra) or *Enterobacter* sp. (Mattes et al., 1998, supra). *Pantoea dispersa* 68J, previously shown to have exceptional efficiency and specificity for production of isomaltulose from sucrose, yielded a gene substantially different from previously characterised sucrose isomerases (less than 70% nucleotide identity or 71% amino acid identity including the leader sequence for export to the periplasm).

Phylogenetic analysis of sucrose isomerase and glucosidase amino acid sequences showed the *P. dispersa* 68J SI divergent from both the trehalulose-producing *P. mesoacidophila* SI and the cluster of predominantly isomaltulose-producing enzymes of *P. rubrum*, *E. rhapontici*, *Klebsiella* sp. and *Enterobacter* sp. (FIG. 13). All sucrose isomerase genes and glucosidases share conserved domains for sugar binding. As a result the conserved sequences and corresponding primers described by Mattes et al. (1998, supra) are not specific for sucrose isomerases and they yield many non-SI genes from different organisms in PCR amplifications (WO 02/18603). The present analysis indicates several conserved regions that appear to be more diagnostic of SIs (Table 8).

Figure 15:
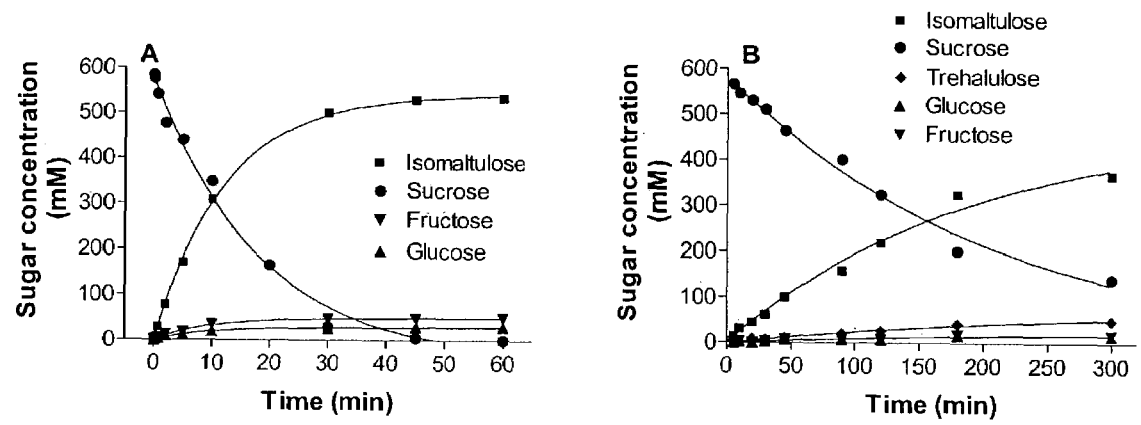
FIG. 15 is a graphical representation showing sucrose conversion by the purified sucrose isomerases cloned from *P. dispersa* 68J (A) or *Klebsiella* sp. 14S (B). Note the time scale difference between panels A and B.

The purified enzyme from expression of the cloned SI gene from *P. dispersa* 68J showed remarkable efficiency and product specificity, rapidly converting 91% of sucrose to isomaltulose, with the remainder as glucose and fructose, and no detectable trehalulose. All isomaltulose synthases previously tested in purified form also produce trehalulose. In the case of the best characterised enzymes from *S. plymuthica* ATCC 15928 and *Klebsiella* sp. LX3, as well as the trehalulose synthase from *P. mesoacidophila* MX-45, the product ratio varies with assay temperature and pH (Véronèse and Perlot, 1999, supra; Zhang et al., 2002, supra; Nagai et al., 1994, supra). These effects were also evident for the purified SI from *Klebsiella* sp. 14S, but the enzyme from *P. dispersa* 68J maintained high product specificity for IM except at the margins of its temperature and pH activity range (FIGS. 15 and 16). High specificity for isomaltulose product over a range of conditions that may develop during a commercial production cycle is an advantage of *P. dispersa* SI for industrial application. The natural high activity and product specificity of *P. dispersa* 68J SI down to pH 4 is another likely advantage for use in plant biofactories.

The cloned *P. dispersa* 68J SI showed the lowest $K_m$ (47 mM) and the highest $V_{max}$ (637 μmoles isomaltulose/mg protein/min) reported for purified isomaltulose synthases (Table 10). It has been speculated that the high $K_m$ values for many SIs has a functional benefit, allowing cells to consume sucrose in limited supply and convert only excess sucrose into isomaltulose reserves (Börnke et al., 2001, supra). Under this hypothesis for SI function and evolution, the highly efficient isomaltulose synthase in *P. dispersa* 68J is initially surprising. However, isomaltulose is an inhibitor of microbial glucosyltransferases and invertase (Takazoe, 1989, supra; Börnke et al., 2001, supra). Production of an efficient isomaltulose synthase could therefore be an advantage under conditions with intense competition for abundant sucrose, where the rapid release of isomaltulose could inhibit development of competing microbial populations. Consistent with this interpretation is the unusual constitutive production of isomaltulose and relatively low propensity to use isomaltulose for growth in *P. dispersa* 68j, and the relatively low sensitivity of the *P. dispersa* SI to inhibition by monosaccharides (FIG. 19).

Whatever the drivers for its evolution, the characteristics of the unusual isomaltulose synthase from *P. dispersa* 68J are incidentally advantageous for use in cell or enzyme based bioreactors, or potentially in engineered plants, for isomaltulose production. Key advantages revealed here are: low $K_m$, high $V_{max}$, high stability in purified form, complete conversion of substrate, high product specificity for isomaltulose across a wide pH and temperature activity range (optimum pH 5, 37° C.), and absence of a reverse reaction converting isomaltulose to glucose, fructose and/or trehalulose. Together, these characteristics result in highly efficient conversion of sucrose into isomaltulose. Further investigation of the unique structural features of the *P. dispersa* SI in comparison with the less efficient and specific isomerases from other species should help to elucidate the mechanisms of isomerase action, and indicate opportunities to further increase stability and activity under conditions for industrial biosynthesis of isomaltulose.

The disclosure of every patent, patent application, and publication cited herein is hereby incorporated herein by reference in its entirety.

The citation of any reference herein should not be construed as an admission that such reference is available as "Prior Art" to the instant application.

Throughout the specification the aim has been to describe the preferred embodiments of the invention without limiting the invention to any one embodiment or specific collection of features. Those of skill in the art will therefore appreciate that, in light of the instant disclosure, various modifications and changes can be made in the particular embodiments exemplified without departing from the scope of the present invention. All such modifications and changes are intended to be included within the scope of the appended claims.

TABLE 10

General characteristics of purified known sucrose isomerases*

| Strains | Maximum yield (%)[#] IM | Maximum yield (%)[#] TH | Optimal temperature (range) | Optimal pH (range) | $K_m$ (mM) | $V_{max}$ | Reference |
|---|---|---|---|---|---|---|---|
| *P. dispersa* 68J | 91 | 0 | 37 (10–60) | 5 (3–8) | 46.6 | 637 U mg$^{-1}$ | This study |
| *Klebsiella sp.* 14S | 62 | 8 | 37 (10–65) | 6 (4–7) | 81.6 | 100 U mg$^{-1}$ | This study |
| *Klebsiella sp.* LX3 | 83 | 21 | 35 (15–50, unstable >40) | 6 (unstable <5, >6.5) | 54.6 | 328 U mg$^{-1}$ (sp. act.) | Zhang et al., (2002, supra) |
| *Klebsiella sp.* | 86 | — | 35 | 6.0–6.5 | 120 | 110 U mg$^{-1}$ | Park et al., (1996, supra) |
| *S. plymuthica* ATCC 15928 | 73 | 9 | 30 | 6.2 | 65 | 120 U mg$^{-1}$ | Véronèse & Perlot, (1999 supra) |
| *E. rhapontici* NCPPB 1578 | 85 | 15 | 30 | 7.0 | 280 | 4.1 U mg$^{-1}$ (sp. act.) | Cheetham, (1984, supra) |
| *P. mesoacidophila* MX-45 | 8 | 91 | 40 (20–60, unstable >40) | 5.8 (4–8) | 19.2 | 13.9 U mg$^{-1}$ (sp. act.) | Nagai et al., (1994, supra) |

*Results for isomaltulose product, except for MX-45 (trehalulose product).
—not specified.
[#]Ultimate percent conversion of sucrose into isomaltulose (IM) or (trehalulose) TH.

The invention claimed is:

1. An isolated polynucleotide comprising a nucleotide sequence selected from the group consisting of SEQ ID NO: 7 or 9, a full-length complement of SEQ ID NO: 7 or 9, and a sequence that is capable of hybridizing to SEQ ID NO: 7 or 9 or to a full-length complement of SEQ ID NO: 7 or 9 under high stringency conditions, wherein the conditions comprise hybridization at 65° C. in 1% BSA, 1 mM EDTA, 0.5 M NaHPO$_4$ (pH 7.2), 7% SDS, and washing at 68° C. in 0.2 x SSC, 0.1% SDS, and wherein the nucleotide sequence encodes an amino acid sequence that has one or more of the following features:
   (a) catalyses the conversion of sucrose into isomaltulose and concomitantly produces trehalulose at a yield of less than 5% of the yield of isomaltulose; or
   (b) catalyses the conversion of sucrose into isomaltulose with a Km of less than 50 mM and with a Vmax of at least 400 μmoles isomaltulose/mg protein/mm; or
   (c) catalyses the conversion of sucrose into isomaltulose but not the hydrolysis of isomaltulose.

2. The polynucleotide of claim 1, wherein the nucleotide sequence comprises a sequence that encodes a consensus sequence selected from the group consisting of SEQ ID NO: 19, 20, 21, 22, 23 and 24.

3. The polynucleotide of claim 2, wherein the sequence that encodes the consensus sequence is selected from the group consisting of SEQ ID NO: 27, 28, 29, 30, 31, 32, 33, 34, 35 or 36 and a sequence that is capable of hybridizing to SEQ ID NO: 27, 28, 29, 30, 31, 32, 33, 34, 35 or 36 under the high stringency conditions.

4. An expression vector comprising the polynucleotide of claim 1 operably linked to a regulatory polynucleotide.

5. An isolated host cell containing the expression vector of claim 4.

6. The host cell of claim 5, which is a bacterium or other prokaryote.

7. The host cell of claim 5, which is a plant cell or other eukaryote.

8. A plant cell containing the expression vector of claim 4, wherein the plant is a species that is capable of synthesizing and/or accumulating sucrose.

9. The plant cell of claim 8, wherein the plant is sugarcane or sugar beet.

10. The plant cell of claim 8, wherein the plant is sugarcane.

11. A method of producing a polypeptide, wherein the method comprises:
   (a) culturing a host cell containing an expression vector comprising the polynucleotide of claim 1, or a fragment of the polynucleotide that encodes an amino acid sequence of at least 20 amino acids having sucrose isomerase activity operably linked to a regulatory polynucleotide, whereby a recombinant polypeptide is expressed from the polynucleotide or the fragment; and
   (b) isolating the polypeptide.

12. A method of producing a polypeptide having sucrose isomerase activity, wherein the method comprising:
   (a) introducing into a cell a polynucleotide encoding a fragment of SEQ ID NO: 8 or 10, wherein the fragment has sucrose isomerase activity and wherein the polynucleotide is operably linked to a regulatory polynucleotide;
   (b) expressing the polynucleotide to produce the fragment; and
   (c) detecting sucrose isomerase activity in the fragment, which indicates production of the polypeptide.

13. An extract of the host cell of claim 5.

14. A transformed plant cell containing the expression vector of claim 4.

15. The plant cell of claim 14, wherein the plant is a species that is capable of synthesizing and/or accumulating sucrose.

16. The plant cell of claim 14, wherein the plant is selected from sugarcane or sugar beet.

17. The plant cell of claim 14, wherein the plant is sugarcane.

18. A polynucleotide according to claim 1, wherein the amino acid sequence displays at least 97% sequence identity to the sequence set forth in SEQ ID NO: 8 or 10.

19. A polynucleotide according to claim 1, wherein the nucleotide sequence displays at least 97% sequence identity to the sequence set forth in SEQ ID NO: 7 or 9, or to a full-length complement of SEQ ID NO: 7 or 9.

20. A method of producing isomaltulose, wherein the method comprises cultivating a plant cell according to claim 8.

21. The method according to claim 20, wherein the plant is sugarcane or sugar beet.

22. The method of claim 21, wherein the plant is sugarcane.

23. A method of producing isomaltulose, wherein the method comprises contacting sucrose or a sucrose-containing substrate with an extract according to claim 13.

* * * * *